United States Patent
Li et al.

(10) Patent No.: US 11,939,307 B2
(45) Date of Patent: Mar. 26, 2024

(54) PHENYLMETHYL-PIPERAZINE DERIVATIVES AND ANTIVIRAL USES THEREOF

(71) Applicant: INSTITUTE OF MEDICINAL BIOTECHNOLOGY, CHINESE ACADEMY OF MEDICAL SCIENCES, Beijing (CN)

(72) Inventors: Yanping Li, Beijing (CN); Zhuorong Li, Beijing (CN); Zonggen Peng, Beijing (CN); Xinbei Jiang, Beijing (CN); Yixuan Wang, Beijing (CN); Jianrui Li, Beijing (CN); Jiali Tan, Beijing (CN)

(73) Assignee: INSTITUTE OF MEDICINAL BIOTECHNOLOGY, CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 17/780,160

(22) PCT Filed: Nov. 29, 2019

(86) PCT No.: PCT/CN2019/000232
§ 371 (c)(1),
(2) Date: May 26, 2022

(87) PCT Pub. No.: WO2021/102600
PCT Pub. Date: Jun. 3, 2021

(65) Prior Publication Data
US 2023/0024612 A1 Jan. 26, 2023

(51) Int. Cl.
*C07D 295/135* (2006.01)
*C07D 205/04* (2006.01)
*C07D 207/14* (2006.01)
*C07D 207/325* (2006.01)
*C07D 211/56* (2006.01)
*C07D 211/58* (2006.01)
*C07D 213/36* (2006.01)
*C07D 233/61* (2006.01)
*C07D 241/04* (2006.01)
*C07D 241/12* (2006.01)
*C07D 401/06* (2006.01)

(52) U.S. Cl.
CPC ....... *C07D 295/135* (2013.01); *C07D 205/04* (2013.01); *C07D 207/14* (2013.01); *C07D 207/325* (2013.01); *C07D 211/56* (2013.01); *C07D 211/58* (2013.01); *C07D 213/36* (2013.01); *C07D 233/61* (2013.01); *C07D 241/04* (2013.01); *C07D 241/12* (2013.01); *C07D 401/06* (2013.01)

(58) Field of Classification Search
None
See application file for complete search history.

(56) References Cited

U.S. PATENT DOCUMENTS 10,252,987 B2 * 4/2019 Li .................... C07D 401/04

FOREIGN PATENT DOCUMENTS

| CN | 104447625 A | 3/2015 | |
|---|---|---|---|
| CN | 106467501 | 3/2017 | |
| CN | 110698432 | 1/2020 | |
| WO | WO2010118367 A2 | 10/2010 | |
| WO | WO-2017028472 A1 * | 2/2017 | .......... A61P 31/16 |

OTHER PUBLICATIONS

International Search Report (English and Chinese) and Written Opinion of PCT/CN2019/000232 dated Aug. 20, 2020, 11 pages.
Romero, D.L. et al., Discovery, Synthesis, and Bioactivity of Bis(heteroaryl)piperazines. 1. A Novel Class of Non-Nucleoside HIV-1 Reverse Transcriptase Inhibitors, Journal of Medicinal Chemistry, 1994, pp. 999-1014, vol. 37, No. 7, Miami, US.

* cited by examiner

*Primary Examiner* — Zinna Northington Davis
(74) *Attorney, Agent, or Firm* — Rankin, Hill & Clark LLP

(57) ABSTRACT

Disclosed are a benzyl piperazine compound, a preparation method there for and an application thereof in an antivirus. The benzyl piperazine compound has a structure represented by the following general formula(I). It is proven by experiments that the benzyl piperazine compound not only has significant antiviral activity, but also has the advantages of low cytotoxicity, a high selectivity index and soon.

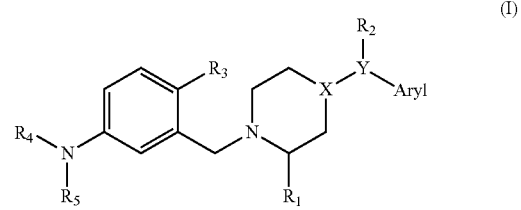

20 Claims, No Drawings

PHENYLMETHYL-PIPERAZINE DERIVATIVES AND ANTIVIRAL USES THEREOF

FIELD OF THE INVENTION

The present invention relates to a genus of novel phenylmethylpiperazines compounds and a method for preparing such compounds; and also relates the use of the compounds in the manufacture of antiviral drugs; in particular, the use of the compounds in the manufacture of drugs against HCV viruses.

BACKGROUND OF THE INVENTION

Viral diseases are the most common infectious diseases, and have become global public health problems due to their features of high infectivity and high variability. Effect targets of the existing antiviral drugs are mostly viral enzymes. Viral enzyme inhibitors drugs have advantages such as explicit targets, high specificity, and strong efficacy, and apparent shortages of narrow antiviral spectrum, and problem of drug resistance leaded by the trends of the high variability of the viruses. The emerging of the new virus variants and unknown viruses make existing antiviral drugs, which have frequent problems of drug resistance, powerless. Therefore, the development of new antiviral drugs is imminent.

The inventors discovered and confirmed that a new genus of substituted phenylmethylpiperazines compounds had strong inhibitory activity on HCV replication, and initial mechanism of action studies showed that it did not act on the replication process of HCV, which is quite different from the mechanism of action of the current direct antiviral drugs. The compounds of the invention and their roles are not reported by relevant literature domestically and abroad to date.

SUMMARY

The main object of the present invention is to screen a new genus of antiviral compounds and pharmaceutically acceptable salts thereof by medicinal chemistry studies of substituted phenylmethylpiperazines, and the compounds not only have significant antiviral activity, but also have the advantages of low cytotoxicity and high selectivity index.

To achieve the above object, the invention employs the following technical means:

At first, the present invention provides compounds having the structure represented by the following general formula I or a pharmaceutically acceptable salt thereof:

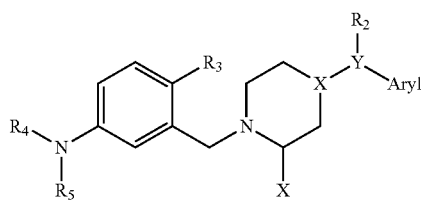

wherein $R_1$ is alkyl containing 1 to 4 carbons or H;
$R_2$ is H, alkyl, cycloalkyl, aryl, heteroaryl, or, aryl or heteroaryl substituted with 1, 2 or 3 substituents, wherein, the substituent is selected from the group consisting of alkyl, cycloalkyl, alkoxy, phenoxy, alkylthio, phenylthio, halogen, cyano, and haloalkyl; when being alkyl or cycloalkyl, $R_2$ is alkyl containing 1 to 6 carbon atoms, or cycloalkyl containing 3 to 6 carbon atoms, or optionally substituted with halogen;
$R_3$ is cyano or trifluoromethyl;
X is N or CH;
Y is CH or single bond connecting X and Aryl; when Y is a single bond, $R_2$ is absent, and $R_3$ is trifluoromethyl;
Aryl is a benzene or aza-aromatic ring, or a benzene or aza-aromatic ring containing 1-3 substituents selected from the group consisting of alkyl, cycloalkyl, alkyloxy, phenoxy or substituted phenoxy, alkylthio, phenylthio or substituted phenylthio, haloalkyl, cyano, and halogen;
$R_4$ is substituted alkyl or substituted heterocycloalkyl, and when $R_4$ is substituted alkyl, the substituent is selected from the group consisting of alkylamino, dialkylamino, and saturated or unsaturated heterocyclyl containing one nitrogen or two nitrogens; when $R_4$ is substituted heterocycloalkyl, the heterocycloalkyl contains at least one nitrogen atom, and the substituent is selected from the group consisting of alkyl, alkylamino and dialkylamino;
$R_5$ is hydrogen or alkyl containing 1-4 carbons;
alternatively, $R_4$, $R_5$, and the nitrogen atom to which they are attached jointly form a cyclic structure containing 1 or 2 nitrogen atoms or cyclic structure substituted with a substituent selected from the group consisting of alkyl containing 1 to 6 carbons, alkylamino, dialkylamino, cycloalkyl, and heterocyclic groups.

Wherein, preferably, the compounds or pharmaceutically acceptable salts thereof have the structure shown in the following general formula II:

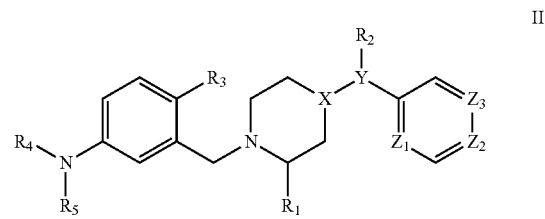

wherein $R_1$ is alkyl containing 1 to 4 carbons or H;
$R_2$ is H, alkyl, cycloalkyl, aryl, heteroaryl, or, aryl or heteroaryl substituted with 1, 2 or 3 substituents, wherein, the substituent is selected from the group consisting of alkyl, cycloalkyl, alkoxy, phenoxy, alkylthio, phenylthio, halogen, cyano, and haloalkyl; when being alkyl or cycloalkyl, $R_2$ is alkyl containing 1 to 6 carbon atoms, or cycloalkyl containing 3 to 6 carbon atoms, or optionally substituted with halogen;
$R_3$ is cyano or trifluoromethyl;
X is N or CH;
Y is CH or a single bond linking X to the aromatic ring containing $Z_1$, $Z_2$, and $Z_3$; when Y is a single bond, $R_2$ is absent, and $R_3$ is trifluoromethyl;
$Z_1$, $Z_2$, $Z_3$ are the same or different, $Z_1$, $Z_2$, $Z_3$ are each $C(R_6)$ or N, respectively, $R_6$ is H, alkyl, cycloalkyl, alkyloxy, phenoxy or substituted phenoxy, alkylthio, phenylthio or substituted phenylthio, haloalkyl, cyano, halogen;

$R_4$ is

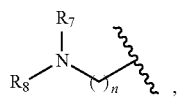

wherein, n=1-3, $R_7$, $R_8$ are each H, alkyl, or substituted alkyl, respectively, or $R_7$ and $R_8$, together with the nitrogen atom to which they are bonded, form a cyclic group or a cyclic group substituted with a substituent selected from the group consisting of alkyl, alkylamino, dialkylamino, and heterocyclyl, such as pyrrolidinyl, the cyclic group is a three-, four-, five-, six-, or seven-membered saturated or unsaturated cyclic group containing 1 or 2 nitrogen atoms, for example, the three-membered cyclic group is selected from aziridinyl, the four-membered cyclic group is selected from azetidinyl, the five membered cyclic group is selected from the group consisting of pyrrolyl, pyrrolidinyl, imidazolyl, and oxazolyl groups, the six-membered cyclic group is selected from the group consisting of morpholine, piperazine, piperidine, pyridine, and pyrimidine groups, and the seven-membered cyclic group is 1,4-diazepanyl;

or $R_4$ is

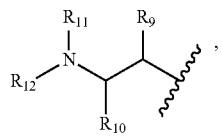

wherein $R_{12}$ is alkyl containing 1-4 carbon atoms, such as methyl, ethyl;

$R_{11}$, the nitrogen to which $R_{11}$ is bound, the carbon to which $R_{10}$ is bound, the carbon to which $R_9$ is bound, and $R_9$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, alkylamino, and dialkylamino, $R_{10}$ is H;

or $R_{11}$ with the nitrogen to which it is bound, the carbon to which $R_{10}$ is bound, and $R_{10}$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, alkylamino, and di-C1-C4 alkylamino, for example, dimethylamino, diethylamino, $R_9$ is H;

alternatively, $R_4$ is alkyl which contains 1-4 carbons and is substituted by amino, alkylamino, dialkylamino, or four-, five-, or six membered saturated heterocycles containing one or two nitrogens;

alternatively, $R_5$, $R_4$ and the nitrogen atom to which they are bonded together form a saturated heterocycle or a saturated heterocycle substituted by a substituent, and the heterocycle is a five-, six- or seven-membered heterocycle containing one or two hetero nitrogen atoms, the substituents are selected from the group consisting of alkyl containing 1 to 6 carbon atoms, alkylamino, di-C1-C4 alkylamino, cycloalkyl containing 3 to 5 carbon atoms or saturated heterocyclic groups containing one nitrogen, such as dimethylamino, diethylamino, cyclopropanyl or pyrrolidinyl.

In the general formula II, preferably, when $R_4$ is

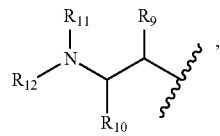

$R_4$ is

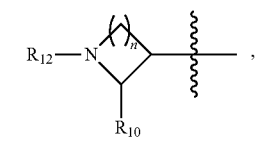

n=2 or 3, $R_{10}$ is H; or $R_4$ is

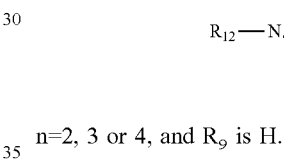

n=2, 3 or 4, and $R_9$ is H.

In the general formula II, preferably, $R_5$, $R_4$ and the nitrogen atom to which they are bonded together form a saturated heterocycle or a saturated heterocycle substituted by a substituent, and the heterocycle is a five-, six- or seven-membered heterocycle containing one or two heteroatoms, the five-membered heterocycle is selected from the group consisting of pyrrolidinyl, pyrrolyl, imidazolyl, imidazolidinyl, and oxazolyl groups, the six-membered heterocycle is selected from the group consisting of morpholine, piperazine, and piperidine, and the seven-membered heterocycle is selected from 1,4-diazepane; the substituents are selected from the group consisting of alkyl containing 1 to 4 carbon atoms, di-C1-C4 alkylamino, cycloalkyl containing 3 to 5 carbon atoms, and heterocyclic groups containing 3 to 5 carbon atoms and one nitrogen, such as methyl, ethyl, methylamino, ethylamino, dimethyl amino, diethylamino, cyclopropyl, or pyrrolidinyl.

In the general formula II, preferably, $R_5$, $R_4$ together with the nitrogen atom to which they are bonded form

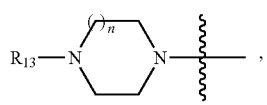

wherein n=1 or 2, $R_{13}$ is alkyl containing 1-4 carbons or cycloalkyl containing 3 to 5 carbons, and the alkyl containing 1-4 carbon is, such as methyl, ethyl;

or $R_5$, $R_4$ together with the nitrogen atom to which they are bonded form

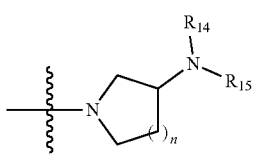

wherein n=1 or 2, $R_{14}$ and $R_{15}$ are alkyl groups containing 1 to 4 carbons; or $R_5$, $R_4$ together with the nitrogen atom to which they are bonded form

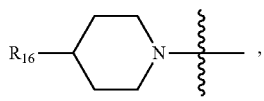

wherein $R_{16}$ is a diC1-C4 alkylamino group, such as dimethylamino, diethylamino, or a saturated five-membered heterocyclic ring containing one nitrogen, such as pyrrolidinyl;

alternatively, $R_5$, $R_4$ together with the nitrogen atom to which they are bonded form

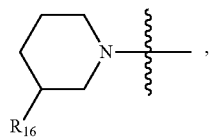

$R_{16}$ is a diC1-C4 alkylamino, e.g., dimethylamino, diethylamino.

Wherein, preferably, the compounds or pharmaceutically acceptable salts thereof have the structure shown in the following general formula III:

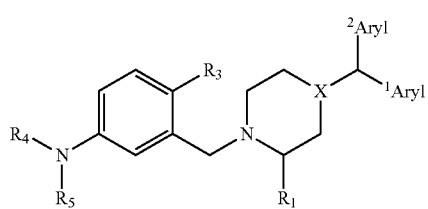

$^1$Aryl is the same as or different from $^2$Aryl, $^1$Aryl and $^2$Aryl are each a benzene ring or aza aromatic ring or a substituted benzene ring or aza aromatic ring, the aza aromatic ring is a heteroaromatic ring containing 1 to 2 nitrogen atoms, preferably pyridine rings and pyrimidine rings, the substitution is that 1 to 2 substituents are at any position on the ring, and the substituents are selected from the group consisting of hydrogen, alkyl, cycloalkyl, alkoxy, phenoxy or substituted phenoxy, alkylthio, phenylthio, phenylthio or substituted phenylthio, haloalkyl, cyano and halogen;

$R_1$ is alkyl containing 1 to 4 carbons or H;
$R_3$ is cyano or trifluoromethyl;
X is N or CH;
$R_4$ is substituted alkyl or substituted heterocycloalkyl, and when $R_4$ is substituted alkyl, the substituent is selected from the group consisting of alkylamino, dialkylamino, and saturated or unsaturated heterocyclyl containing one nitrogen or two nitrogens; when $R_4$ is a substituted heterocycloalkyl, the heterocycloalkyl contains at least one nitrogen atom, and the substituent is selected from the group consisting of alkyl, alkylamino and dialkylamino;

$R_5$ is hydrogen or an alkyl containing 1-4 carbons;

or, $R_5$, $R_4$ and the nitrogen atom to which they are bonded together form a saturated heterocycle or a saturated heterocycle substituted by a substituent, and the heterocycle is a five-, six- or seven-membered heterocycle containing one or two nitrogen atoms, the substituents are selected from the group consisting of alkyl containing 1 to 6 carbon atoms, C1-C4 alkylamino, di-C1-C4 alkylamino, cycloalkyl containing 3 to 5 carbon atoms or saturated heterocyclic groups containing one nitrogen, such as dimethylamino, diethylamino, cyclopropanyl or pyrrolidinyl.

In the general formula III, preferably, $R_4$ is

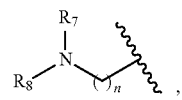

wherein, n=1-3, $R_7$ and $R_8$ are H or alkyl or substituted alkyl, or $R_7$ and $R_8$ together with the nitrogen atom to which they are bonded form a cyclic group or substituted cyclic group, the substituent is selected from the group consisting of alkyl, alkylamino, dialkylamino and heterocyclic group, such as pyrrolidinyl, the cyclic group is three-, four-, five-, six- or seven-membered saturated or unsaturated cyclic group containing 1 or 2 nitrogen atoms, for example, the three-membered cyclic group is selected from aziridinyl, and the four-membered cyclic group is selected from azetidinyl, the five-membered cyclic group is selected from the group consisting of pyrrolyl, pyrrolidinyl, imidazolyl and oxazolyl groups, and the six-membered cyclic group is selected from the group consisting of morpholinyl, piperazinyl, piperidinyl, pyridinyl, and pyrimidinyl groups, the seven-membered cyclic group is 1,4-diazepanyl;

or $R_4$ is

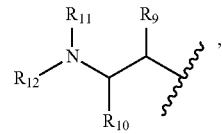

wherein $R_{12}$ is alkyl containing 1-4 carbon atoms, such as methyl, ethyl;

$R_{11}$, the nitrogen to which $R_{11}$ is bound, the carbon to which $R_{10}$ is bound, the carbon to which $R_9$ is bound, and $R_9$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, C1-C4 alkylamino, and di C1-C4 alkylamino, $R_{10}$ is H;

or, $R_4$ is a substituted alkyl, the substituent is selected from the group consisting of amino, alkylamino, dialkylamino, and four-, five-, or six-membered saturated heterocycles containing one or two nitrogens.

In the general formula III, preferably, when R$_4$ is

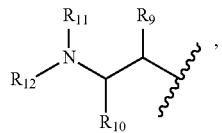

R$_4$ is

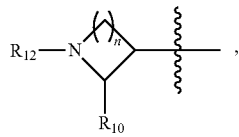

n=2 or 3, R$_{10}$ is H; or R$_4$ is

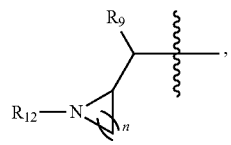

n=2, 3 or 4, and R$_9$ is H.

In the general formula III, preferably, R$_5$, R$_4$ and the nitrogen atom to which they are bonded together form a saturated heterocycle or a saturated heterocycle substituted by a substituent, and the heterocycle is a five-, six- or seven-membered heterocycle containing one or two heteroatoms, the five-membered heterocycle is selected from the group consisting of pyrrolidinyl, pyrrolyl, imidazolyl, imidazolidinyl, and oxazolyl groups, the six-membered heterocycle is selected from the group consisting of morpholine, piperazine, and piperidine, and the seven-membered heterocycle is selected from 1,4-diazepane; the substituents are selected from the group consisting of alkyl containing 1 to 4 carbon atoms, di-C1-C4 alkylamino, cycloalkyl containing 3 to 5 carbon atoms, and heterocyclic groups containing 3 to 5 carbon atoms and one nitrogen, such as methyl, ethyl, alkylamino, dimethylamino, diethyl amino, cyclopropyl, or pyrrolidinyl.

In the general formula III, preferably, R$_5$, R$_4$ together with the nitrogen atom to which they are bonded form

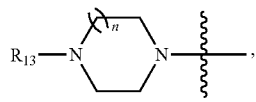

wherein n=1 or 2, R$_{13}$ is alkyl containing 1-4 carbons or cycloalkyl containing 3 to 5 carbons, and the alkyl containing 1-4 carbon is, such as methyl, ethyl;

or R$_5$, R$_4$ together with the nitrogen atom to which they are bonded form

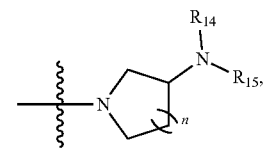

wherein n=1 or 2, R$_{14}$ and R$_{15}$ are alkyl groups containing 1 to 4 carbons;

or R$_5$, R$_4$ together with the nitrogen atom to which they are bonded form

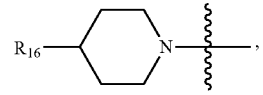

wherein R$_{16}$ is a diC1-C4 alkylamino group, such as dimethylamino, diethylamino, or a saturated five-membered heterocyclic ring containing one nitrogen, such as pyrrolidinyl;

or, R$_5$, R$_4$ together with the nitrogen atom to which they are bonded form

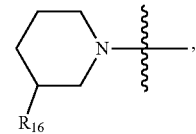

R$_{16}$ is a diC1-C4 alkylamino, e.g., dimethylamino, diethylamino.

Wherein, preferably, the compounds or pharmaceutically acceptable salts thereof have the structure shown in the following general formula IV:

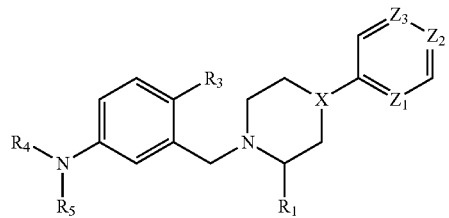

IV

R$_1$ is alkyl containing 1 to 4 carbons or H;
R$_3$ is trifluoromethyl;
X is N or CH;
Z$_1$, Z$_2$, Z$_3$ are the same or different, Z$_1$, Z$_2$, Z$_3$ are each C(R$_6$) or N, respectively, R$_6$ is H, alkyl, cycloalkyl, alkyloxy, phenoxy or substituted phenoxy, alkylthio, phenylthio or substituted phenylthio, haloalkyl, cyano, halogen;
R$_4$ is substituted alkyl or substituted heterocycloalkyl, and when R$_4$ is substituted alkyl, the substituent is selected from the group consisting of alkylamino, dialkylamino, and saturated or unsaturated heterocyclyl containing one nitrogen or two nitrogens; when R$_4$ is a substituted heterocycloalkyl, the heterocycloalkyl contains at least one nitrogen atom, and the substituent is selected from the group consisting of alkyl, alkylamino and dialkylamino;

$R_5$ is hydrogen or an alkyl containing 1-4 carbons;

or, $R_5$, $R_4$ and the nitrogen atom to which they are bonded together form a saturated heterocycle or a saturated heterocycle substituted by a substituent, and the heterocycle is a five-, six- or seven-membered heterocycle containing one or two hetero nitrogen atoms, the substituents are selected from the group consisting of alkyl containing 1 to 6 carbon atoms, alkylamino, di-C1-C4 alkylamino, cycloalkyl containing 3 to 5 carbon atoms or saturated heterocyclic groups containing one nitrogen, such as dimethylamino, diethylamino, cyclopropanyl or pyrrolidinyl.

In the general formula IV, preferably, $R_4$ is

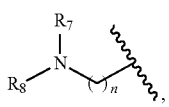

wherein, n=1-3, $R_7$ and $R_8$ are H or alkyl or substituted alkyl, or $R_7$ and $R_8$ together with the nitrogen atom to which they are bonded form a cyclic group or substituted cyclic group, the substituent is selected from the group consisting of alkyl, alkylamino, dialkylamino and heterocyclic group, such as pyrrolidinyl, such as pyrrolidin-1-yl, the cyclic group is three-, four-, five-, six- or seven-membered saturated or unsaturated cyclic group containing 1 or 2 nitrogen atoms, for example, the three-membered cyclic group is selected from aziridinyl, and the four-membered cyclic group is selected from azetidinyl, the five-membered cyclic group is selected from the group consisting of pyrrolyl, pyrrolidinyl, imidazolyl and oxazolyl groups, and the six-membered cyclic group is selected from the group consisting of morpholinyl, piperazinyl, piperidinyl, pyridinyl, and pyrimidinyl groups, the seven-membered cyclic group is 1,4-diazepanyl;

or $R_4$ is

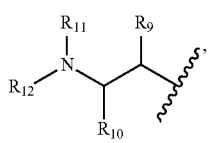

wherein $R_{12}$ is alkyl containing 1-4 carbon atoms, such as methyl, ethyl;

$R_{11}$, the nitrogen to which $R_{11}$ is bound, the carbon to which $R_{10}$ is bound, the carbon to which $R_9$ is bound, and $R_9$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, alkylamino, and dialkylamino, $R_{10}$ is H; or $R_{11}$ with the nitrogen to which it is bound, the carbon to which $R_{10}$ is bound, and $R_{10}$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, alkylamino, and di-C1-C4 alkylamino, for example, dimethylamino, diethylamino, $R_9$ is H;

or, $R_4$ is a substituted alkyl, the substituent is selected from the group consisting of amino, alkylamino, dialkylamino, and four-, five-, or six-membered saturated heterocycles containing one or two nitrogens.

In the general formula IV, preferably, When $R_4$ is

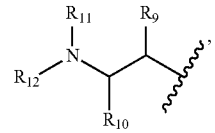

$R_4$ is

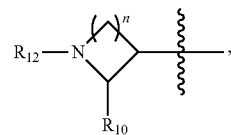

n=2 or 3, $R_{10}$ is H; or $R_4$ is

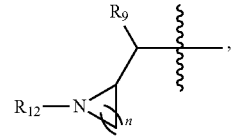

n=2, 3 or 4, and $R_9$ is H.

In the general formula IV, preferably, $R_5$, $R_4$ and the nitrogen atom to which they are bonded together form a saturated heterocycle or a saturated heterocycle substituted by a substituent, and the heterocycle is a five-, six- or seven-membered heterocycle containing one or two heteroatoms, the five-membered heterocycle is selected from the group consisting of pyrrolidinyl, pyrrolyl, imidazolyl, imidazolidinyl, and oxazolyl groups, the six-membered heterocycle is selected from the group consisting of morpholine, piperazine, and piperidine, and the seven-membered heterocycle is selected from 1,4-diazepane; the substituents are selected from the group consisting of alkyl containing 1 to 4 carbon atoms, di-C1-C4 alkylamino, cycloalkyl containing 3 to 5 carbon atoms, and heterocyclic groups containing 3 to 5 carbon atoms and one nitrogen, such as methyl, ethyl, alkylamino, dimethylamino, diethyl amino, cyclopropyl, or pyrrolidinyl.

In the general formula IV, preferably, $R_5$, $R_4$ together with the nitrogen atom to which they are bonded form

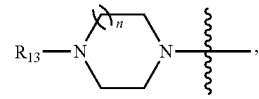

wherein n=1 or 2, $R_{13}$ is alkyl containing 1-4 carbons or cycloalkyl containing 3 to 5 carbons, and the alkyl containing 1-4 carbon is, such as methyl, ethyl;

or $R_5$, $R_4$ together with the nitrogen atom to which they are bonded form

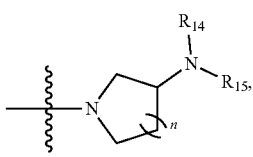

wherein n=1 or 2, $R_{14}$ and $R_{15}$ are alkyl groups containing 1 to 4 carbons;
or $R_5$, $R_4$ together with the nitrogen atom to which they are bonded form

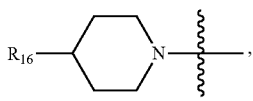

wherein $R_{16}$ is a diC1-C4 alkylamino group, such as dimethylamino, diethylamino, or a saturated five-membered heterocyclic ring containing one nitrogen, such as pyrrolidinyl;
or, $R_5$, $R_4$ together with the nitrogen atom to which they are bonded form

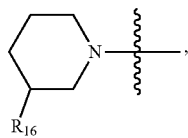

$R_{16}$ is a diC1-C4 alkylamino, e.g., dimethylamino, diethylamino.

In specific embodiments of the present invention, the compounds can be selected from:
1-(3-((4-(1-(4-bromophenyl)ethyl)piperazin-1-yl)methyl)-4-(trifluoromethyl)phenyl)-4-methyl-1,4-diazepane
1-(3-((4-(4-chlorobenzyl)piperazin-1-yl)methyl)-4-(trifluoromethyl)phenyl)-4-methyl-1,4-diazepane
1-(3-((4-(1-(3-chloro-4-fluorophenyl)ethyl)piperazin-1-yl)methyl)-4-(trifluoromethyl)phenyl)-4-methyl-1,4-diazepane
1-(3-((4-(4-chloro-3-methylbenzyl)piperazin-1-yl)methyl)-4-(trifluoromethyl)phenyl)-4-methyl-1,4-diazepane
1-(3-((4-(1-(4-methoxyphenyl)butyl)piperazin-1-yl)methyl)-4-(trifluoromethyl)phenyl)-4-methyl-1,4-diazepane
1-(3,4-dichlorobenzyl)-4-(5-(4-methylpiperazin-1-yl)-2-(trifluoromethyl)benzyl)piperazine
1-(3-((4-(4-chlorobenzyl)piperidin-1-yl)methyl)-4-(trifluoromethyl)phenyl)-4-methyl-1,4-diazepane
$N^1$-(3-((4-(1-(4-bromophenyl)propyl)piperazin-1-yl)methyl)-4-(trifluoromethyl)phenyl)-$N^1,N^2,N^2$-trimethylethan-1,2-diamine
$N^1$-(3-((4-(1-(4-chlorophenyl)ethyl)piperazin-1-yl)methyl)-4-(trifluoromethyl)phenyl)-$N^1,N^2,N^2$-trimethylethan-1,2-diamine
$N^1,N^1,N^2$-trimethyl-$N^2$-(3-((4-(4-methylbenzyl)piperazin-1-yl)methyl)-4-(trifluoromethyl)phenyl)ethan-1,2-diamine
2-((4-(4-chloro-3-methylbenzyl)piperazin-1-yl)methyl)-4-(4-ethylpiperazin-1-yl)benzonitrile
2-((4-(4-chlorobenzyl)piperazin-1-yl)methyl)-4-(4-cyclopropylpiperazin-1-yl)benzonitrile
2-((4-(1-(4-chlorophenyl)ethyl)piperazin-1-yl)methyl)-4-((2-(ethyl(methylamino)ethyl)(methylamino)benzonitrile
4-(3-(dimethylamino)piperidin-1-yl)-2-((4-(1-phenylethyl)piperazin-1-yl)methyl)benzonitrile
4-((2-(dimethylamino)ethyl)(methyl)amino)-2-((4-(1-(4-(trifluoromethyl)phenyl)ethyl)piperazin-1-yl)methyl)benzonitrile
2-((4-(1-(4-chlorophenyl)-2-methylpropyl)piperazin-1-yl)methyl)-4-(methyl(2-(pyrrolidin-1-yl)ethyl)amino)benzonitrile
2-((4-(3-chloro-4-fluorobenzyl)piperazin-1-yl)methyl)-4-((2-(diethylamino)ethyl)(methyl)amino)benzonitrile
4-((3-(1H-imidazol-1-yl)propyl)amino)-2-((4-(3,4-dichlorobenzyl)piperazin-1-yl)methyl)benzonitrile
$N^1$-(3-((4-(4-chlorophenyl)piperazin-1-yl)methyl)-4-(trifluoromethyl)phenyl)-$N^1,N^2,N^2$-trimethylethan-1,2-diamine
$N^1$-(3-((4-(4-bromophenyl)piperazin-1-yl)methyl)-4-(trifluoromethyl)phenyl)-$N^1,N^2,N^2$-trimethylethan-1,2-diamine
3-((4-(4-chlorophenyl)piperazin-1-yl)methyl)-N-methyl-N-((1-methylpiperidin-2-yl)methyl)-4-(trifluoromethyl)aniline
1-(3-((4-(4-chlorophenyl)-2-methylpiperazin-1-yl)methyl)-4-(trifluoromethyl)phenyl)-4-methyl-1,4-diazepane
1-(3-((4-(4-chlorophenyl)piperazin-1-yl)methyl)-4-(trifluoromethyl)phenyl)-4-methyl-1,4-diazepane
3-((4-(4-bromophenyl)piperazin-1-yl)methyl)-N-methyl-N-((1-methylpyrrolidin-2-yl)methyl)-4-(trifluoromethyl)aniline
3-((4-(4-chlorophenyl)piperazin-1-yl)methyl)-N-((1-ethylpyrrolidin-2-yl)methyl)-N-methyl-4-(trifluoromethyl)aniline
$N^1$-(3-((4-(4-bromo-3-chlorophenyl)piperazin-1-yl)methyl)-4-(trifluoromethyl)phenyl)-$N^1,N^2,N^2$-trimethylethan-1,2-diamine
1-(3-((4-(4-chlorophenyl)piperazin-1-yl)methyl)-4-(trifluoromethyl)phenyl)-N,N-dimethylpiperidin-4-amine
1-(4-chlorophenyl)-4-(5-(4-(pyrrolidin-1-yl)piperidin-1-yl)-2-(trifluoromethyl)benzyl)piperazine
1-(3-((4-(4-chlorophenyl)piperazin-1-yl)methyl)-4-(trifluoromethyl)phenyl)-N,N-dimethylpyrrolidin-3-amine
1-(4-chlorophenyl)-4-(5-(4-methylpiperazin-1-yl)-2-(trifluoromethyl)benzyl)piperazine 3-((4-(4-chlorophenyl)-2-methylpiperazin-1-yl)methyl)-N-methyl-N-(piperidin-1-ylmethyl)-4-(trifluoromethyl)aniline
1-(3-((4-(4-chloro-3-(trifluoromethyl)phenyl)-2-methylpiperazin-1-yl)methyl)-4-(trifluoromethyl)phenyl)-4-methyl-1,4-diazepane
$N^1$-(3-((4-(4-bromo-3-(trifluoromethyl)phenyl)-2-methylpiperazin-1-yl)methyl)-4-(trifluoromethyl)phenyl)-$N^1,N^2,N^2$-trimethyl ethan-1,2-diamine
1-methyl-4-(3-((2-propyl-4-(4-(trifluoromethyl)phenyl)piperazin-1-yl)methyl)-4-(trifluoromethyl)phenyl)-1,4-diazepane
1-(3-((4-(3-chloro-4-methylphenyl)piperazin-1-yl)methyl)-4-(trifluoromethyl)phenyl)-4-ethyl-1,4-diazepane
1-(3-((4-(4-fluorophenyl)piperazin-1-yl)methyl)-4-(trifluoromethyl)phenyl)-4-methyl-1,4-diazepane
1-(3-((4-(3-chloro-4-fluorophenyl)piperazin-1-yl)methyl)-4-(trifluoromethyl)phenyl)-4-methyl-1,4-diazepane
$N^1$-(3-((4-(4-bromo-3-chlorophenyl)piperazin-1-yl)methyl)-4-(trifluoromethyl)phenyl)-$N^1,N^2,N^2$-trimethyl ethan-1,2-diamine
3-((4-(4-chlorophenyl)piperidin-1-yl)methyl)-N-methyl-N-(2-(pyrrolidin-1)ethyl)-4-(trifluoromethyl)aniline 1-(3-((4-(4-chloro-3-methylphenyl)piperazin-1-yl)methyl)-4-(trifluoromethyl)phenyl)-4-methyl-1,4-diazepane $N^1$-(3-((4-(4-chloro-3-fluorophenyl)piperazin-1-yl)methyl)-4-(trifluoromethyl)phenyl)-$N^1$,$N^2$,$N^2$-trimethyl ethan-1,2-diamine $N^1$-(3-((4-(3,4-dichlorophenyl)piperidin-1-yl)methyl)-4-(trifluoromethyl)phenyl)-$N^1$,$N^2$,$N^2$-trimethyl ethan-1,2-diamine 1-(3-((4-(4-chloro-3-methylphenyl)piperidin-1-yl)methyl)-4-(trifluoromethyl)phenyl)-4-methyl-1,4-diazepane 1-(3-((4-(bis(4-fluorophenyl)methyl)piperazin-1-yl)methyl)-4-(trifluoromethyl)phenyl)-4-methyl-1,4-diazepane 1-(3-((4-(bis(4-methylphenyl)methyl)piperazin-1-yl)methyl)-4-(trifluoromethyl)phenyl)-4-methyl-1,4-diazepane 1-(3-((4-(bis(4-chlorophenyl)methyl)piperazin-1-yl)methyl)-4-(trifluoromethyl)phenyl)-4-methyl-1,4-diazepane 1-(3-((4-(bis(4-bromophenyl)methyl)piperazin-1-yl)methyl)-4-(trifluoromethyl)phenyl)-4-methyl-1,4-diazepane 1-(3-((4-(bis(4-isopropylphenyl)methyl)piperazin-1-yl)methyl)-4-(trifluoromethyl)phenyl)-4-methyl-1,4-diazepane $N^1$-(3-((4-(bis(4-cyclopropylphenyl)methyl)piperazin-1-yl)methyl)-4-(trifluoropropyl)phenyl)-$N^1$,$N^2$,$N^2$-trimethylethan-1,2-diamine N-(2-(azetidin-1-yl)ethyl)-3-((4-(bis(4-chlorophenyl)methyl)piperazin-1-yl)methyl)-N-methyl-4-(trifluoromethyl)aniline 1-(3-(4-(4-fluorophenyl)(phenyl)methyl)piperazin-1-yl)methyl)-4-(trifluoromethyl)phenyl)-4-methyl-1,4-diazepane $N^1$-(3-((4-(bis(4-chlorophenyl)methyl)piperazin-1-yl)methyl)-4-(trifluoromethyl)phenyl)-$N^1$,$N^2$,$N^2$-trimethyl ethan-1,2-diamine $N^1$-(3-((4-(bis(4-(trifluoromethyl)phenyl)methyl)piperazin-1-yl)methyl)-4-(trifluoromethyl)phenyl)-$N^1$,$N^2$,$N^2$-trimethyl ethan-1,2-diamine $N^1$-(3-((4-((4-chlorophenyl)(phenyl)methyl)piperazin-1-yl)methyl)-4-(trifluoromethyl)phenyl)-$N^1$,$N^2$,$N^2$-trimethyl ethan-1,2-diamine 1-(bis(4-chlorophenyl)methyl)-4-(5-(4-methylpiperazin-1-yl)-2-(trifluoromethyl)benzyl)piperazine 1-(3-((4-((4-chlorophenyl)(pyridin-2-yl)methyl)piperazin-1-yl)methyl)-4-(trifluoromethyl)phenyl)-4-methyl-1,4-diazepane 1-methyl-4-(3-((4-(phenyl(pyridin-2-yl)methyl)piperazin-1-yl)methyl)-4-(trifluoromethyl)phenyl)-1,4-diazepane $N^1$-(3-((4-(bis(4-methoxyphenyl)methyl)piperazin-1-yl)methyl)-4-(trifluoromethyl)phenyl)-$N^1$,$N^2$,$N^2$-trimethylethan-1,2-diamine $N^1$-(3-((4-(bis(4-chlorophenyl)methyl)piperazin-1-yl)methyl)-4-(trifluoromethyl)phenyl)-$N^2$,$N^2$-dimethyl-$N^1$-propylethan-1,2-diamine 1-(3-((4-(bis(4-fluorophenyl)methyl)-2-methylpiperazin-1-yl)methyl)-4-(trifluoromethyl)phenyl)-4-methyl-1,4-diazepane 1-(3-((4-(bis(4-chlorophenyl)methyl)-2-methylpiperazin-1-yl)methyl)-4-(trifluoromethyl)phenyl)-4-methyl-1,4-diazepane 3-((4-(bis(4-chlorophenyl)methyl)piperazin-1-yl)methyl)-N-methyl-N-((1-methylpyrrolidin-2-yl)methyl)-4-(trifluoromethyl)aniline 3-((4-(bis(4-chlorophenyl)methyl)piperazin-1-yl)methyl)-N-methyl-N-(2-(pyrrolidin-1-yl)ethyl)-4-(trifluoromethyl)aniline N-(2-(aziridin-1-yl)ethyl)-3-((4-(bis(4-chlorophenyl)methyl)piperazin-1-yl)methyl)-N-methyl-4-(trifluoromethyl)aniline 1-(3-((4-(di(pyridin-2-yl)methyl)piperazin-1-yl)methyl)-4-(trifluoromethyl)phenyl)-4-ethyl-1,4-diazepane $N^1$-(3-((4-(bis(4-fluorophenyl)methyl)piperazin-1-yl)methyl)-4-(trifluoromethyl)phenyl)-$N^1$,$N^2$,$N^2$-trimethyl ethan-1,2-diamine 1-(3-((4-(bis(4-chlorophenyl)methyl)piperazin-1-yl)methyl)-4-(trifluoromethyl)phenyl)-N,N-dimethylpiperidin-3-amine 1-(bis(4-bromophenyl)methyl)-4-(5-(4-methylpiperazin-1-yl)-2-(trifluoromethyl)benzyl)piperazine 1-(3-((4-(bis(4-fluorophenyl)methyl)piperazin-1-yl)methyl)-4-(trifluoromethyl)phenyl)-N,N-dimethylpiperidin-4-amine $N^1$-(3-((4-(bis(4-chlorophenyl)methyl)piperazin-1-yl)methyl)-4-(trifluoromethyl)phenyl)-$N^1$,$N^2$-dimethyl-$N^2$-propylethan-1,2-diamine $N^1$-(3-((4-(bis(4-fluorophenyl)methyl)piperazin-1-yl)methyl)-4-(trifluoromethyl)phenyl)-$N^2$-(2-(dimethylamino)ethyl)-$N^1$,$N^2$-dimethylethan-1,2-diamine $N^1$-(3-((4-(bis(4-chlorophenyl)methyl)piperidin-1-yl)methyl)-4-(trifluoromethyl)phenyl)-$N^1$,$N^2$,$N^2$-trimethyl-ethan-1,2-diamine $N^1$-(3-((4-(bis(4-bromophenyl)methyl)piperidin-1-yl)methyl)-4-(trifluoromethyl)phenyl)-$N^1$,$N^2$,$N^2$-trimethyl-ethan-1,2-diamine 2-((4-(bis(4-chlorophenyl)methyl)piperazin-1-yl)methyl)-4-((2-(dimethylamino)ethyl)(methyl)amino)benzonitrile 2-((4-(bis(4-methoxyphenyl)methyl)piperazin-1-yl)methyl)-4-(4-methyl-1,4-diazepan-1-yl)benzonitrile 2-((4-(bis(4-fluorophenyl)methyl)piperazin-1-yl)methyl)-4-(4-methyl-1,4-diazepan-1-yl)benzonitrile 2-((4-(bis(4-chlorophenyl)methyl)piperazin-1-yl)methyl)-4-(4-methyl-1,4-diazepan-1-yl)benzonitrile 4-((2-(1H-imidazol-1-yl)ethyl)(methyl)amino)-2-((4-(bis(4-chlorophenyl)methyl)piperazin-1-yl)methyl)benzonitrile 2-((4-(di(pyridin-4-yl)methyl)piperazin-1-yl)methyl)-4-((2-(dimethylamino)ethyl)(methyl)amino)benzonitrile 2-((4-(bis(4-chlorophenyl)methyl)piperazin-1-yl)methyl)-4-(4-methylpiperazin-1-yl)benzonitrile 2-((4-(bis(4-isopropylphenyl)methyl)piperazin-1-yl)methyl)-4-((2-(dimethylamino)ethyl)(methyl)amino)benzonitrile 2-((4-(bis(4-tert-butylphenyl)methyl)piperazin-1-yl)methyl)-4-((2-(dimethylamino)ethyl)(methyl)amino)benzonitrile 2-((4-(bis(4-bromophenyl)methyl)piperazin-1-yl)methyl)-4-((2-(dimethylamino)ethyl)(methyl)amino)benzonitrile 2-((4-(bis(4-cyclopropylphenyl)methyl)piperazin-1-yl)methyl)-4-((2-(dimethylamino)ethyl)(methyl)amino)benzonitrile 2-((4-(bis(4-chlorophenyl)methyl)piperazin-1-yl)methyl)-4-(3-(dimethylamino)pyrrolidin-1-yl)benzonitrile 2-((4-(bis(4-chlorophenyl)methyl)piperazin-1-yl)methyl)-4-(methyl(2-(pyrrolidin-1-yl)ethyl)amino)benzonitrile 4-((2-(aziridin-1-yl)ethyl)(methyl)amino)-2-((4-(bis(4-chlorophenyl)methyl)piperazin-1-yl)methyl)benzonitrile 2-((4-((4-chlorophenyl)(phenyl)methyl)piperazin-1-yl)methyl)-4-(4-methyl-1,4-diazepan-1-yl)benzonitrile 2-((4-((4-chlorophenyl)(pyridin-4-yl)methyl)piperazin-1-yl)methyl)-4-(4-methyl-1,4-diazepan-1-yl)benzonitrile 2-((4-(bis(4-chlorophenyl)methyl)piperidin-1-yl)methyl)-4-((2-(dimethyl amino)ethyl)(methyl)amino)benzonitrile 2-((4-(bis(4-fluorophenyl)methyl)piperidin-1-yl)methyl)-4-(4-methyl-1,4-diazepan-1-yl)benzonitrile N-{3-[4-(4-chlorophenyl)piperazin-1-yl]methyl-4-(trifluoromethyl)phenyl}-N, 1-dimethylpyrrolidin-3-amine 4-[{2-[ethyl(methyl)amino]ethyl}(methyl)amino]-2-({4-[1-(pyrazin-2-yl)ethyl]piperazin-1-yl}methyl)benzonitrile N1-(3-[{4-[bis(3,4-dichlorophenyl)methyl]piperazin-1-yl}methyl]-4-(trifluoromethyl)phenyl)-N2,N2-diethyl-N1-methylethan-1,2-diamine 2-({4-[bis(4-chloro-3-methylphenyl)methyl]piperazin-1-yl}methyl)-4-{[2-(dimethylamino)ethyl](methyl)amino}benzonitrile 1-[3-({4-[cyclohexyl(3,4-dichlorophenyl)methyl]piperazin-1-yl}methyl)-4-(trifluoromethyl)phenyl]-4-methyl-1,4-diazepane 2-({4-[(4-chlorophenyl)(cyclobutyl)methyl]piperazin-1-yl}methyl)-4-(4-methyl-1,4-diazepan-1-yl)benzonitrile 2-[(4-chlorophenyl) {4-(5-(4-methylpiperazin-1-yl)-2-(trifluoromethyl)benzyl]piperazin-1-yl}methyl]pyrazine 4-(4-methylpiperazin-1-yl)-2-[(4-{(pyrazin-2-yl)[(4-(trifluoromethyl)phenyl]methyl}piperazin-1-yl)methyl]benzonitrile 1-methyl-4-[3-({4-[(4-phenoxyphenyl)(pyridin-2-yl)methyl]piperazin-1-yl}methyl)-4-(trifluoromethyl)phenyl]-1,4-diazepane N-{3-([4-{bis[4-(phenylthio)phenyl]methyl}piperazin-1-yl]methyl)-4-(trifluoromethyl)phenyl}-1-ethyl-N-methylpyrrolidin-3-amine 2-({4-(bis(4-(methylthio)phenyl]methyl}piperazin-1-yl)methyl)-4-{[2-(dimethylamino)ethyl](methyl)amino}benzonitrile 3-([4-{bis[4-(trifluoromethyl)phenyl]methyl}piperazin-1-yl]methyl)-N-methyl-N-[2-(pyrrolidin-1-yl)ethyl]-4-(trifluoromethyl)aniline 2-({4-[(4-cyanophenyl)(cyclopentyl)methyl]piperazin-1-yl}methyl)-4-{[2-(dimethylamino)ethyl](methyl)amino}benzonitrile 4-{1-(4-[5-{[2-(dimethylamino)ethyl](methyl)amino}-2-(trifluoromethyl)benzyl]piperazin-1-yl)ethyl}benzonitrile 4-([3-(1H-imidazol-1-yl)propyl]amino)-2-({4-[bis(4-chlorophenyl)methyl]piperazin-1-yl}methyl)benzonitrile $N^1$-(3-((4-(3,4-dichlorophenyl)piperazin-1-yl)methyl)-4-(trifluoromethyl)phenyl)-$N^1,N^2,N^2$-trimethylethan-1,2-diamine $N^1$-(3-((4-(3-methyl-4-chlorophenyl)piperazin-1-yl)methyl)-4-(trifluoromethyl)phenyl)-$N^1,N^2,N^2$-trimethylethan-1,2-diamine, or 1-(3-((4-(3,4-dichlorophenyl)piperazin-1-yl)methyl)-4-(trifluoromethyl)phenyl)-4-methyl-1,4-diazepane.

Further, the invention also provides a method for preparing the compounds or pharmaceutically acceptable salts thereof, comprising the steps of:

step 1: reacting 2-(bromomethyl)-4-fluorobenzonitrile or 2-(bromomethyl)-4-fluoro-1-(trifluoromethyl) benzene (A) as raw material with the corresponding substituted piperazine or piperidine (C) in polar solvents such as acetone or DMSO, employing sodium ethoxide or potassium carbonate as an deacid reagent, to obtain the corresponding intermediate (B);

step 2: in the presence of bases such as potassium carbonate or triethylamine, in polar solvents such as DMF or DMSO, condensing B with corresponding amine (d) and removing HF to obtain compounds of general formula I;

wherein $R_1$ to $R_2$, $R_4$ to $R_5$, X, Y, $Z_1$ to $Z_3$ are as defined in any of the above;

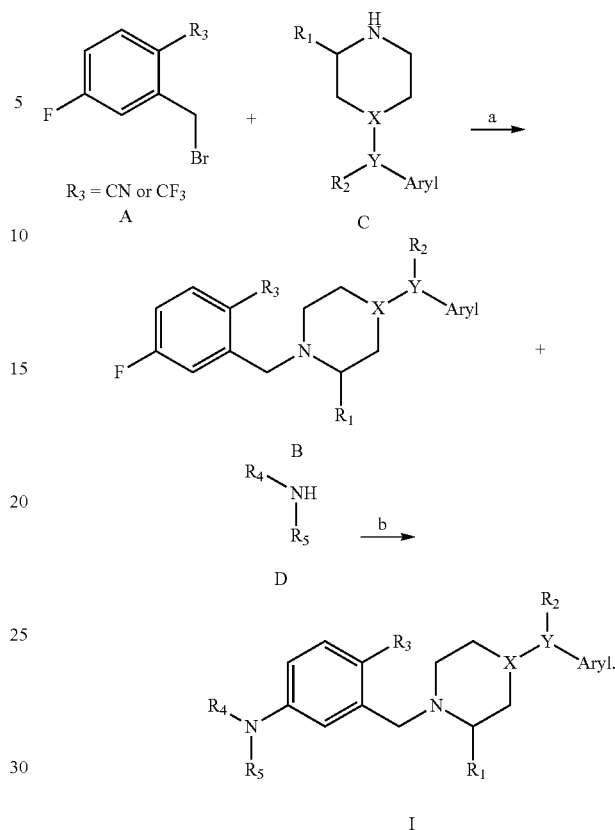

Further, the present invention also provides a pharmaceutical composition comprising a therapeutically effective amount of one or more compounds as mentioned in the present invention or a pharmaceutically acceptable salt thereof, and comprising one or more pharmaceutically acceptable excipients.

Wherein, preferably, the pharmaceutically acceptable salts refer to the product from salt forming reaction of a compound of the present invention with an acid, including inorganic acid salts such as hydrochloride, hydrobromide or sulfate and the like; organic acid salts such as acetate, lactate, succinate, fumarate, maleate, citrate, benzoate, methanesulfonate, or 4-methylbenzoate salt.

Wherein, preferably, the compounds of the present invention or a pharmaceutically acceptable salt thereof is used as an active ingredient, and present in an amount of 0.1% to 99.5% by weight of the pharmaceutical composition. Preferably, the pharmaceutical composition contains 0.5%-99.5% by weight of the active ingredient.

Further, the present invention also provides the use of the compounds or pharmaceutically acceptable salt thereof or the pharmaceutical composition in the manufacture of a medicament against virus, wherein the virus is a DNA virus and/or a RNA virus, or a hepatitis virus.

Wherein, preferably, the DNA viruses are herpes viruses, hepatotropic viruses, adenoviruses, or papilloma viruses; and the RNA viruses are mumps viruses, influenza viruses, coronaviruses, retroviruses, enterovirus or flaviviruses, or, the viruses are hepatitis C viruses.

Further, the present invention also provides the method for treating viral infections, which comprises administering to the patient a therapeutically effective amount of the compounds of the present invention or pharmaceutically acceptable salt thereof or the pharmaceutical composition, wherein the virus is a DNA virus and/or a RNA virus, or a hepatitis virus.

Wherein, preferably, the DNA viruses are herpes viruses, hepatotropic viruses, adenoviruses, or papilloma viruses; and the RNA viruses are mumps viruses, influenza viruses, coronaviruses, retroviruses, enterovirus or flaviviruses, or, the viruses are hepatitis C viruses.

The terms involved in this paper have the following meanings without specific definitions:

"Substituted" means, but is not limited to, being substituted with one or more substituents selected from the group consisting of halogen, alkoxy, hydroxy, alkyl, amino, alkylamino, aminoalkyl, alkenyl and phenyl. For example, "substituted piperazine" may be, but is not limited to, piperazine substituted at each substitutable position with a substituent selected from the group consisting of halogen, alkoxy, hydroxy, alkyl, amino, alkenyl, phenyl and substituted amino. As another example, "substituted benzene ring" can be, but is not limited to, benzene rings substituted by one substituent, such as alkyl, alkoxy, hydroxyl, amino, phenoxy, phenylthio, halogen, or polysubstituted benzene rings with these substituents in different positions thereof.

"Alkyl" may be, but not limited to straight or branched chain alkyl with number of carbon atoms of 1-6, more preferably C1-C4 lower alkyl, for example, methyl, ethyl, isopropyl, n-propyl, n-butyl, isobutyl, sec-butyl, tert-butyl, n-pentyl, isopentyl, n-hexyl, isohexyl and the like.

"Alkoxy" may be, but not limited to alkoxy with number of carbon atoms of 1 to 6, more preferably C1-C4 lower alkoxy, for example, methoxy, ethoxy, isopropoxy, n-propoxy, n-butoxy, isobutoxy, sec-butoxy, tert-butoxy, n-pentoxy, isopentyloxy, n-hexyloxy, iso-hexyloxy and the like.

"Alkenyl" may be, but not limited to alkenyl with number of carbon atoms of 2 to 4, e.g., vinyl, propenyl, allyl, 1-butenyl, 2-butenyl, isobutenyl. Allyl is more preferable.

"Halo" or "halogen" may be fluoro, chloro, bromo or iodo. Fluoro, chloro or bromo is more preferable.

"Aminoalkyl" may be, but not limited to alkyl with number of carbon atoms of 1-6 substituted by amino, e.g., amino methyl, amino ethyl, amino isopropyl, amino n-propyl, amino n-butyl, amino isobutyl, amino sec-butyl, amino tert-butyl, amino n-pentyl, amino isopentyl, amino n-hexyl, amino isohexyl and the like. Amino (C1-C4) alkyl is more preferable.

"Amino", "Aminoalkyl" and "dialkylamino" respectively refer to —NH$_2$, —NHR and —NR$_2$, and R is alkyl as defined above. Two alkyls connected to the nitrogen atom in dialkyl moiety may be the same or different.

DETAILED DESCRIPTION

The present invention will be described in further detail by reference to the following specific examples, but the present invention is not limited to the following specific examples.

Example 1: Synthesis of 1-(3-((4-(bis(4-fluorophenyl)methyl)piperazin-1-yl) methyl)-4-(trifluoromethyl)phenyl)-4-methyl-1,4-diazepane (44)

305 µL 5-fluoro-2-(trifluoromethyl)benzyl bromide was dissolved in 6 mL acetone, added 617 mg 1-(bis(4-fluorophenyl)methyl)piperazine and 805 mg anhydrous potassium carbonate under stirring, and reacted at room temperature for 2.5 hours. After the reaction was completed, the reaction system was filtered by suction, the solvent of the filtrate was removed by rotary distillation, and 6 mL ethyl acetate and 3 mL distilled water were added for extraction, the organic phase was washed with saturated sodium chloride solution, then anhydrous magnesium sulfate was added for drying, and then filtered, concentrated, purified by column chromatography (petroleum ether:ethyl acetate=10:1) to obtain intermediate1-(bis(4-fluorophenyl)methyl)-4-(5-fluoro-2-(trifluoromethyl)benzyl)piperazine (80% yield). 232 mg of 1-(bis(4-fluorophenyl)methyl)-4-(5-fluoro-2-(trifluoromethyl)benzyl)piperazine was dispersed in 4 mL of anhydrous DMSO, the mixture was placed in a 15 mL pressure-resistant tube, and 187 µL N-methylhomopiperazine and 207 mg anhydrous potassium carbonate were added, the reaction was conducted at 120° C. for 96 hours under airtight conditions, and the raw materials monitored by TLC had completely disappeared. The reaction system was filtered, the filtrate was extracted with ethyl acetate and water, and the organic layer was washed with water and saturated sodium chloride solution, added anhydrous magnesium sulfate to dry and then filtered, purified by column chromatography (dichloromethane:methanol=10:1) to obtain product 1-(3-((4-(bis(4-fluorophenyl)methyl)piperazin-1-yl) methyl)-4-(trifluoromethyl) phenyl)-4-methyl-1,4-diazepane (58% yield), mass spectrum (ESI$^+$): m/z=559.3 (M+H)$^+$.

The following compounds were obtained by the methods similar to that in Example 1:

(1) 1-(3-((4-(1-(4-bromophenyl)ethyl)piperazin-1-yl) methyl)-4-(trifluoromethyl)phenyl)-4-methyl-1,4-diazepane mass spectrum (ESI$^+$): m/z=539.2 (M+H)$^+$ (2) 1-(3-((4-(4-chlorobenzyl)piperazin-1-yl)methyl)-4-(trifluoromethyl)phenyl)-4-methyl-1,4-diazepane mass spectrum (ESI$^+$): m/z=481.2 (M+H)$^+$ (3) 1-(3-((4-(1-(3-chloro-4-fluorophenyl)ethyl)piperazin-1-yl)methyl)-4-(trifluoromethyl)phenyl)-4-methyl-1,4-diazepane mass spectrum (ESI$^+$): m/z=513.2 (M+H)$^+$ (4) 1-(3-((4-(4-chloro-3-methylbenzyl)piperazin-1-yl) methyl)-4-(trifluoromethyl)phenyl)-4-methyl-1,4-diazepane mass spectrum (ESI$^+$): m/z=495.2 (M+H)$^+$ (5) 1-(3-((4-(1-(4-methoxyphenyl)butyl)piperazin-1-yl) methyl)-4-(trifluoromethyl)phenyl)-4-methyl-1,4-diazepane mass spectrum (ESI$^+$): m/z=519.3 (M+H)$^+$ (6) 1-(3,4-dichlorobenzyl)-4-(5-(4-methylpiperazin-1-yl)-2-(trifluoromethyl)benzyl)piperazine mass spectrum (ESI$^+$): m/z=501.2 (M+H)$^+$ (7) 1-(3-((4-(4-chlorobenzyl)piperidin-1-yl)methyl)-4-(trifluoromethyl)phenyl)-4-methyl-1,4-diazepane mass spectrum (ESI$^+$): m/z=480.2 (M+H)$^+$ (8) N$^1$-(3-((4-(1-(4-bromophenyl)propyl)piperazin-1-yl) methyl)-4-(trifluoromethyl)phenyl)-N$^1$,N$^2$,N$^2$-trimethylethan-1,2-diamine mass spectrum (ESI$^+$): m/z=541.2 (M+H)$^+$ (9) N$^1$-(3-((4-(1-(4-chlorophenyl)ethyl)piperazin-1-yl) methyl)-4-(trifluoromethyl)phenyl)-N$^1$,N$^2$,N$^2$-trimethylethan-1,2-diamine mass spectrum (ESI$^+$): m/z=483.2 (M+H)$^+$

(10) N$^1$,N$^1$,N$^2$-trimethyl-N$^2$-(3-((4-(4-methylbenzyl)piperazin-1-yl)methyl)-4-(trifluoromethyl)phenyl)ethan-1,2-diamine mass spectrum (ESI$^+$): m/z=449.3 (M+H)$^+$

(19) N¹-(3-((4-(4-chlorophenyl)piperazin-1-yl)methyl)-4-(trifluoromethyl)phenyl)-N¹,N²,N²-trimethylethan-1,2-diamine
mass spectrum (ESI⁺): m/z=455.2 (M+H)⁺

(20) N¹-(3-((4-(4-bromophenyl)piperazin-1-yl)methyl)-4-(trifluoromethyl)phenyl)-N¹,N²,N²-trimethylethan-1,2-diamine
mass spectrum (ESI⁺): m/z=499.2 (M+H)⁺

(21) 3-((4-(4-chlorophenyl)piperazin-1-yl)methyl)-N-methyl-N-((1-methylpiperidin-2-yl)methyl)-4-(trifluoromethyl)aniline
mass spectrum (ESI⁺): m/z=495.2 (M+H)⁺

(22) 1-(3-((4-(4-chlorophenyl)-2-methylpiperazin-1-yl)methyl)-4-(trifluoromethyl)phenyl)-4-methyl-1,4-diazepane
mass spectrum (ESI⁺): m/z=481.2 (M+H)⁺

(23) 1-(3-((4-(4-chlorophenyl)piperazin-1-yl)methyl)-4-(trifluoromethyl)phenyl)-4-methyl-1,4-diazepane
mass spectrum (ESI⁺): m/z=467.2 (M+H)⁺

(24) 3-((4-(4-bromophenyl)piperazin-1-yl)methyl)-N-methyl-N-((1-methylpyrrolidin-2-yl)methyl)-4-(trifluoromethyl)aniline
mass spectrum (ESI⁺): m/z=525.2 (M+H)⁺

(25) 3-((4-(4-chlorophenyl)piperazin-1-yl)methyl)-N-((1-ethylpyrrolidin-2-yl)methyl)-N-methyl-4-(trifluoromethyl)aniline
mass spectrum (ESI⁺): m/z=495.2 (M+H)⁺

(26) N¹-(3-((4-(4-bromo-3-chlorophenyl)piperazin-1-yl)methyl)-4-(trifluoromethyl)phenyl)-N¹,N²,N²-trimethylethan-1,2-diamine
mass spectrum (ESI⁺): m/z=533.1 (M+H)⁺

(27) 1-(3-((4-(4-chlorophenyl)piperazin-1-yl)methyl)-4-(trifluoromethyl)phenyl)-N,N-dimethylpiperidin-4-amine
mass spectrum (ESI⁺): m/z=481.2 (M+H)⁺

(28) 1-(4-chlorophenyl)-4-(5-(4-(pyrrolidin-1-yl)piperidin-1-yl)-2-(trifluoromethyl)benzyl)piperazine
mass spectrum (ESI⁺): m/z=507.2 (M+H)⁺

(29) 1-(3-((4-(4-chlorophenyl)piperazin-1-yl)methyl)-4-(trifluoromethyl)phenyl)-N,N-dimethylpyrrolidin-3-amine
mass spectrum (ESI⁺): m/z=467.2 (M+H)⁺

(30) 1-(4-chlorophenyl)-4-(5-(4-methylpiperazin-1-yl)-2-(trifluoromethyl)benzyl)piperazine
mass spectrum (ESI⁺): m/z=453.2 (M+H)⁺

(31) 3-((4-(4-chlorophenyl)-2-methylpiperazin-1-yl)methyl)-N-methyl-N-(piperidin-1-ylmethyl)-4-(trifluoromethyl)aniline
mass spectrum (ESI⁺): m/z=495.2 (M+H)⁺

(32) 1-(3-((4-(4-chloro-3-(trifluoromethyl)phenyl)-2-methylpiperazin-1-yl)methyl)-4-(trifluoromethyl)phenyl)-4-methyl-1,4-diazepane
mass spectrum (ESI⁺): m/z=549.2 (M+H)⁺

(33) N¹-(3-((4-(4-bromo-3-(trifluoromethyl)phenyl)-2-methylpiperazin-1-yl)methyl)-4-(trifluoromethyl)phenyl)-N¹,N²,N²-trimethylethan-1,2-diamine
mass spectrum (ESI⁺): m/z=581.2 (M+H)⁺

(34) 1-methyl-4-(3-((2-propyl-4-(4-(trifluoromethyl)phenyl)piperazin-1-yl)methyl)-4-(trifluoromethyl)phenyl)-1,4-diazepane
mass spectrum (ESI⁺): m/z=543.3. (M+H)⁺

(35) 1-(3-((4-(3-chloro-4-methylphenyl)piperazin-1-yl)methyl)-4-(trifluoromethyl)phenyl)-4-ethyl-1,4-diazepane
mass spectrum (ESI⁺): m/z=495.2 (M+H)⁺

(36) 1-(3-((4-(4-fluorophenyl)piperazin-1-yl)methyl)-4-(trifluoromethyl)phenyl)-4-methyl-1,4-diazepane
mass spectrum (ESI⁺): m/z=451.2 (M+H)⁺

(37) 1-(3-((4-(3-chloro-4-fluorophenyl)piperazin-1-yl)methyl)-4-(trifluoromethyl)phenyl)-4-methyl-1,4-diazepane
mass spectrum (ESI⁺): m/z=485.2 (M+H)⁺

(38) N¹-(3-((4-(4-bromo-3-chlorophenyl)piperazin-1-yl)methyl)-4-(trifluoromethyl)phenyl)-N¹,N²,N²-trimethylethan-1,2-diamine
mass spectrum (ESI⁺): m/z=533.1 (M+H)⁺

(39) 3-((4-(4-chlorophenyl) piperidin-1-yl)methyl)-N-methyl-N-(2-pyrrolidin-1-yl) ethyl-4-(trifluoromethyl)aniline
mass spectrum (ESI⁺): m/z=480.2 (M+H)⁺

(40) 1-(3-((4-(4-chloro-3-methylphenyl)piperazin-1-yl)methyl)-4-(trifluoromethyl)phenyl)-4-methyl-1,4-diazepane
mass spectrum (ESI⁺): m/z=481.2 (M+H)⁺

(41) N¹-(3-((4-(4-chloro-3-fluorophenyl)piperazin-1-yl)methyl)-4-(trifluoromethyl)phenyl)-N¹,N²,N²-trimethylethan-1,2-diamine
mass spectrum (ESI⁺): m/z=473.2 (M+H)⁺

(42) N¹-(3-((4-(3,4-dichlorophenyl)piperidin-1-yl)methyl)-4-(trifluoromethyl)phenyl)-N¹,N²,N²-trimethylethan-1,2-diamine
mass spectrum (ESI⁺): m/z=488.2 (M+H)⁺

(43) 1-(3-((4-(4-chloro-3-methylphenyl)piperidin-1-yl)methyl)-4-(trifluoromethyl)phenyl)-4-methyl-1,4-diazepane
mass spectrum (ESI⁺): m/z=480.2 (M+H)⁺

(45) 1-(3-((4-(bis(4-methylphenyl)methyl)piperazin-1-yl)methyl)-4-(trifluoromethyl)phenyl)-4-methyl-1,4-diazepane
mass spectrum (ESI⁺): m/z=551.3 (M+H)⁺

(46) 1-(3-((4-(bis(4-chlorophenyl)methyl)piperazin-1-yl)methyl)-4-(trifluoromethyl)phenyl)-4-methyl-1,4-diazepane
mass spectrum (ESI⁺): m/z=591.2 (M+H)⁺

(47) 1-(3-((4-(bis(4-bromophenyl)methyl)piperazin-1-yl)methyl)-4-(trifluoromethyl)phenyl)-4-methyl-1,4-diazepane
mass spectrum (ESI⁺): m/z=679.1 (M+H)⁺

(48) 1-(3-((4-(bis(4-isopropylphenyl)methyl)piperazin-1-yl)methyl)-4-(trifluoromethyl)phenyl)-4-methyl-1,4-diazepane
mass spectrum (ESI⁺): m/z=607.4 (M+H)⁺

(49) N¹-(3-((4-(bis(4-cyclopropylphenyl)methyl)piperazin-1-yl)methyl)-4-(trifluoromethyl)phenyl)-N¹,N²,N²-trimethylethan-1,2-diamine
mass spectrum (ESI⁺): m/z=591.4 (M+H)⁺

(50) N¹-(2-(azetidin-1-yl)ethyl)-3-((4-(bis(4-chlorophenyl)methyl)piperazin-1-yl)methyl)-N-methyl-4-(trifluoromethyl)aniline
mass spectrum (ESI⁺): m/z=591.2 (M+H)⁺

(51) 1-(3-((4-((4-fluorophenyl)(phenyl)methyl)piperazin-1-yl)methyl)-4-(trifluoromethyl)phenyl)-4-methyl-1,4-diazepane
mass spectrum (ESI⁺): m/z=541.3 (M+H)⁺

(52) N¹-(3-((4-(bis(4-chlorophenyl)methyl)piperazin-1-yl)methyl)-4-(trifluoromethyl)phenyl)-N¹,N²,N²-trimethylethan-1,2-diamine
mass spectrum (ESI⁺): m/z=579.2 (M+H)⁺

(53) N¹-(3-((4-(bis(4-(trifluoromethyl)phenyl)methyl)piperazin-1-yl)methyl)-4-(trifluoromethyl)phenyl)-N¹,N²,N²-trimethylethan-1,2-diamine
mass spectrum (ESI⁺): m/z=647.3 (M+H)⁺

(54) N¹-(3-((4-((4-chlorophenyl)(phenyl)methyl)piperazin-1-yl)methyl)-4-(trifluoromethyl)phenyl)-N¹,N²,N²-trimethylethan-1,2-diamine mass spectrum (ESI⁺): m/z=545.3 (M+H)⁺

(55) 1-(bis(4-chlorophenyl)methyl)-4-(5-(4-methylpiperazin-1-yl)-2-(trifluoromethyl)benzyl)piperazine mass spectrum (ESI⁺): m/z=577.2 (M+H)⁺

(56) 1-(3-((4-((4-chlorophenyl)(pyridin-2-yl)methyl)piperazin-1-yl)methyl)-4-(trifluoromethyl)phenyl)-4-methyl-1,4-diazepane mass spectrum (ESI⁺): m/z=558.3 (M+H)⁺

(57) 1-methyl-4-(3-((4-(phenyl(pyridin-2-yl)methyl)piperazin-1-yl)methyl)-4-(trifluoromethyl)phenyl)-1,4-diazepane mass spectrum (ESI⁺): m/z=524.3 (M+H)⁺

(58) N¹-(3-((4-(bis(4-methoxyphenyl)methyl)piperazin-1-yl)methyl)-4-(trifluoromethyl)phenyl)-N¹,N²,N²-trimethylethan-1,2-diamine mass spectrum (ESI⁺): m/z=571.3 (M+H)⁺

(59) N¹-(3-((4-(bis(4-chlorophenyl)methyl)piperazin-1-yl)methyl)-4-(trifluoromethyl)phenyl)-N²,N²-dimethyl-N¹-propylethan-1,2-diamine mass spectrum (ESI⁺): m/z=607.2 (M+H)⁺

(60) 1-(3-((4-(bis(4-fluorophenyl)methyl)-2-methylpiperazin-1-yl)methyl)-4-(trifluoromethyl)phenyl)-4-methyl-1,4-diazepane mass spectrum (ESI⁺): m/z=573.3 (M+H)⁺

(61) 1-(3-((4-(bis(4-chlorophenyl)methyl)-2-methylpiperazin-1-yl)methyl)-4-(trifluoromethyl)phenyl)-4-methyl-1,4-diazepane mass spectrum (ESI⁺): m/z=605.2 (M+H)⁺

(62) 3-((4-(bis(4-chlorophenyl)methyl)piperazin-1-yl)methyl)-N-methyl-N-((1-methylpyrrolidin-2-yl)methyl)-4-(trifluoromethyl)aniline mass spectrum (ESI⁺): m/z=605.2 (M+H)⁺

(63) 3-((4-(bis(4-chlorophenyl)methyl)piperazin-1-yl)methyl)-N-methyl-N-(2-(pyrrolidin-1-yl)ethyl)-4-(trifluoromethyl)aniline mass spectrum (ESI⁺): m/z=605.2 (M+H)⁺

(64) N-(2-(aziridin-1-yl)ethyl)-3-((4-(bis(4-chlorophenyl)methyl)piperazin-1-yl)methyl)-N-methyl-4-(trifluoromethyl)aniline mass spectrum (ESI⁺): m/z=577.2 (M+H)⁺

(65) 1-(3-((4-(di(pyridin-2-yl)methyl)piperazin-1-yl)methyl)-4-(trifluoromethyl)phenyl)-4-ethyl-1,4-diazepane mass spectrum (ESI⁺): m/z=539.3 (M+H)⁺

(66) N¹-(3-((4-(bis(4-fluorophenyl)methyl)piperazin-1-yl)methyl)-4-(trifluoromethyl)phenyl)-N¹,N²,N²-trimethylethan-1,2-diamine mass spectrum (ESI⁺): m/z=547.3 (M+H)⁺

(67) 1-(3-((4-(bis(4-chlorophenyl)methyl)piperazin-1-yl)methyl)-4-(trifluoromethyl)phenyl)-N,N-dimethylpiperidin-3-amine mass spectrum (ESI⁺): m/z=605.2 (M+H)⁺

(68) 1-(bis(4-bromophenyl)methyl)-4-(5-(4-methylpiperazin-1-yl)-2-(trifluoromethyl)benzyl)piperazine mass spectrum (ESI⁺): m/z=665.1 (M+H)⁺

(69) 1-(3-((4-(bis(4-fluorophenyl)methyl)piperazin-1-yl)methyl)-4-(trifluoromethyl)phenyl)-N,N-dimethylpiperidin-4-amine mass spectrum (ESI⁺): m/z=573.3 (M+H)⁺

(70) N¹-(3-((4-(bis(4-chlorophenyl)methyl)piperazin-1-yl)methyl)-4-(trifluoromethyl)phenyl)-N¹,N²-dimethyl-N²-propylethan-1,2-diamine mass spectrum (ESI⁺): m/z=607.2 (M+H)⁺

(71) N¹-(3-((4-(bis(4-fluorophenyl)methyl)piperazin-1-yl)methyl)-4-(trifluoromethyl)phenyl)-N²-(2-(dimethylamino)ethyl)-N¹,N²-dimethylethan-1,2-diamine mass spectrum (ESI⁺): m/z=604.3 (M+H)⁺

(72) N¹-(3-((4-(bis(4-chlorophenyl)methyl)piperidin-1-yl)methyl)-4-(trifluoromethyl)phenyl)-N¹,N²,N²-trimethylethan-1,2-diamine mass spectrum (ESI⁺): m/z=578.2 (M+H)⁺

(73) N¹-(3-((4-(bis(4-bromophenyl)methyl)piperidin-1-yl)methyl)-4-(trifluoromethyl)phenyl)-N¹,N²,N²-trimethylethan-1,2-diamine mass spectrum (ESI⁺): m/z=666.1 (M+H)⁺

(92) N-{3-[4-(4-chlorophenyl)piperazin-1-yl]methyl-4-(trifluoromethyl)phenyl}-N,1-dimethylpyrrolidin-3-amine mass spectrum (ESI⁺): m/z=467.2 (M+H)⁺

(94) N1-(3-[{4-[bis(3,4-dichlorophenyl)methyl]piperazin-1-yl}methyl]-4-(trifluoromethyl)phenyl)-N2,N2-diethyl-N1-methylethan-1,2-diamine mass spectrum (ESI⁺): m/z=675.2 (M+H)⁺

(96) 1-[3-({4-[cyclohexyl(3,4-dichlorophenyl)methyl]piperazin-1-yl}methyl)-4-(trifluoromethyl)phenyl]-4-methyl-1,4-diazepane mass spectrum (ESI⁺): m/z=597.3 (M+H)⁺

(98) 2-[(4-chlorophenyl){4-(5-(4-methylpiperazin-1-yl)-2-(trifluoromethyl)benzyl]piperazin-1-yl}methyl]pyrazine mass spectrum (ESI⁺): m/z=545.2 (M+H)⁺

(100) 1-methyl-4-[3-({4-[(4-phenoxyphenyl)(pyridin-2-yl)methyl]piperazin-1-yl}methyl)-4-(trifluoromethyl)phenyl]-1,4-diazepane mass spectrum (ESI⁺): m/z=616.3 (M+H)⁺

(101) N-{3-([4-{bis[4-(phenylthio)phenyl]methyl}piperazin-1-yl]methyl)-4-(trifluoromethyl)phenyl}-1-ethyl-N-methylpyrrolidin-3-amine mass spectrum (ESI⁺): m/z=753.3 (M+H)⁺

(103) 3-([4-{bis[4-(trifluoromethyl)phenyl]methyl}piperazin-1-yl]methyl)-N-methyl-N-[2-(pyrrolidin-1-yl)ethyl]-4-(trifluoromethyl)aniline mass spectrum (ESI⁺): m/z=673.3 (M+H)⁺

(105) 4-{1-(4-[5-{[2-(dimethylamino)ethyl](methyl)amino}-2-(trifluoromethyl)benzyl]piperazin-1-yl)ethyl}benzonitrile mass spectrum (ESI⁺): m/z=474.3 (M+H)⁺

(107) N¹-(3-((4-(3,4-dichlorophenyl)piperazin-1-yl)methyl)-4-(trifluoromethyl)phenyl)-N¹,N²,N²-trimethylethan-1,2-diamine mass spectrum (ESI⁺): m/z=489.2 (M+H)⁺

(108) N¹-(3-((4-(3-methyl-4-chlorophenyl)piperazin-1-yl)methyl)-4-(trifluoromethyl)phenyl)-N¹,N²,N²-trimethylethan-1,2-diamine mass spectrum (ESI⁺): m/z=469.2 (M+H)⁺

(109) 1-(3-((4-(3,4-dichlorophenyl)piperazin-1-yl)methyl)-4-(trifluoromethyl)phenyl)-4-methyl-1,4-diazepane mass spectrum (ESI⁺): m/z=501.1 (M+H)⁺

Example 2: Synthesis of 4-((3-(1H-pyrrol-1-yl)propyl)amino)-2-((4-(3,4-dichlorobenzyl)piperazin-1-yl)methyl)benzonitrile (18)

642 mg 5-fluoro-2-cyanobenzyl bromide (3.0 mmol) was dissolved in 10 mL acetone, added 808 mg 1-(3,4-dichlorobenzyl)piperazine (3.3 mmol) and 1242 mg anhydrous potassium carbonate (9.0 mmol) under stirring, and reacted at room temperature for 3 hours. After the reaction was completed, the reaction system was filtered by suction, the solvent of the filtrate was removed by rotary distillation, after 6 mL ethyl acetate was added to dissolve, 3 mL distilled water was added and stirred fully before standing and stratifying, the organic phase was washed again with saturated sodium chloride solution, an appropriate amount of anhydrous magnesium sulfate was added for drying, and then filtered, purified by column chromatography (petroleum ether:ethyl acetate=10:1) to obtain intermediate 2-((4-(3,4-dichlorobenzyl)piperazin-1-yl)methyl)-4-fluoro-benzonitrile (75% yield). 378 mg of 2-((4-(3,4-dichlorobenzyl) piperazin-1-yl) methyl)-4-fluoro-benzonitrile was dissolved ultrasonically in 3.0 mL anhydrous DMSO, the mixture was placed in a 15 mL pressure-resistant tube, 354 μL 3-(1H-pyrrol-1-yl)propan-1-amine (3.0 mmol) and 414 mg anhydrous potassium carbonate (3.0 mmol) were added under stirring, the reaction was conducted at 120° C. for 8 hours under airtight conditions, and the raw materials monitored by TLC had completely disappeared. The reaction system was filtered, the filtrate was dried to remove the solvent, and the remaining was dissolved by adding 6 mL ethyl acetate, then washed with water and saturated sodium chloride solution successively, added anhydrous magnesium sulfate to dry and then filtered, purified by column chromatography (dichloromethane:methanol=8:1) to obtain product 4-((3-(1H-pyrrol-1-yl)propyl)amino)-2-((4-(3,4-dichlorobenzyl) piperazin-1-yl)methyl)benzonitrile (47% yield), mass spectrum (ESI$^+$): m/z=482.2 (M+H)$^+$.

The following compounds were obtained by the methods similar to that in Example 2:

(11) 2-((4-(4-chloro-3-methylbenzyl)piperazin-1-yl) methyl)-4-(4-ethylpiperazin-1-yl)benzonitrile
mass spectrum (ESI$^+$): m/z=452.2 (M+H)$^+$
(12) 2-((4-(4-chlorobenzyl)piperazin-1-yl)methyl)-4-(4-cyclopropylpiperazin-1-yl)benzonitrile
mass spectrum (ESI$^+$): m/z=450.2 (M+H)$^+$
(13) 2-((4-(1-(4-chlorophenyl)ethyl)piperazin-1-yl) methyl)-4-((2-(ethyl(methyl)amino)ethyl)(methyl) amino)benzonitrile
mass spectrum (ESI$^+$): m/z=454.3 (M+H)$^+$
(14) 4-(3-(dimethylamino)piperidin-1-yl)-2-((4-(1-phenylethyl)piperazin-1-yl)methyl)benzonitrile
mass spectrum (ESI$^+$): m/z=432.3 (M+H)$^+$
(15) 4-((2-(dimethylamino)ethyl)(methyl)amino)-2-((4-(1-(4-(trifluoromethyl)phenyl)ethyl)piperazin-1-yl) methyl)benzonitrile
mass spectrum (ESI$^+$): m/z=474.3 (M+H)$^+$
(16) 2-((4-(1-(4-chlorophenyl)-2-methylpropyl)piperazin-1-yl)methyl)-4-(methyl(2-(pyrrolidin-1-yl)ethyl) amino)benzonitrile
mass spectrum (ESI$^+$): m/z=494.3 (M+H)$^+$
(17) 2-((4-(3-chloro-4-fluorobenzyl)piperazin-1-yl) methyl)-4-((2-(diethylamino)ethyl)(methyl)amino) benzonitrile
mass spectrum (ESI$^+$): m/z=472.3 (M+H)$^+$
(74) 2-((4-(bis(4-chlorophenyl)methyl)piperazin-1-yl) methyl)-4-((2-(dimethylamino)ethyl)(methyl)amino) benzonitrile
mass spectrum (ESI$^+$): m/z=536.2 (M+H)$^+$
(75) 2-((4-(bis(4-methoxyphenyl)methyl)piperazin-1-yl) methyl)-4-(4-methyl-1,4-diazepan-1-yl)benzonitrile
mass spectrum (ESI$^+$): m/z=540.3 (M+H)$^+$
(76) 2-((4-(bis(4-fluorophenyl)methyl)piperazin-1-yl) methyl)-4-(4-methyl-1,4-diazepan-1-yl)benzonitrile
mass spectrum (ESI$^+$): m/z=516.3 (M+H)$^+$
(77) 2-((4-(bis(4-chlorophenyl)methyl)piperazin-1-yl) methyl)-4-(4-methyl-1,4-diazepan-1-yl)benzonitrile
mass spectrum (ESI$^+$): m/z=548.2 (M+H)$^+$
(78) 4-((2-(1H-imidazol-1-yl)ethyl)(methyl)amino)-2-((4-(bis(4-chlorophenyl)methyl)piperazin-1-yl)methyl) benzonitrile
mass spectrum (ESI$^+$): m/z=559.2 (M+H)$^+$
(79) 2-((4-(di(pyridin-4-yl)methyl)piperazin-1-yl) methyl)-4-((2-(dimethylamino)ethyl)(methyl)amino) benzonitrile
mass spectrum (ESI$^+$): m/z=470.3 (M+H)$^+$
(80) 2-((4-(bis(4-chlorophenyl)methyl)piperazin-1-yl) methyl)-4-(4-methylpiperazin-1-yl)benzonitrile
mass spectrum (ESI$^+$): m/z=534.2 (M+H)$^+$
(81) 2-((4-(bis(4-isopropylphenyl)methyl)piperazin-1-yl) methyl)-4-((2-(dimethylamino)ethyl)(methyl)amino) benzonitrile
mass spectrum (ESI$^+$): m/z=552.4 (M+H)$^+$
(82) 2-((4-(bis(4-tert-butylphenyl)methyl)piperazin-1-yl) methyl)-4-((2-(dimethylamino)ethyl)(methyl)amino) benzonitrile
mass spectrum (ESI$^+$): m/z=580.4 (M+H)$^+$
(83) 2-((4-(bis(4-bromophenyl)methyl)piperazin-1-yl) methyl)-4-((2-(dimethylamino)ethyl)(methyl)amino) benzonitrile
mass spectrum (ESI$^+$): m/z=624.1 (M+H)$^+$
(84) 2-((4-(bis(4-cyclopropylphenyl)methyl)piperazin-1-yl)methyl)-4-((2-(dimethylamino)ethyl)(methyl) amino)benzonitrile
mass spectrum (ESI$^+$): m/z=548.4 (M+H)$^+$
(85) 2-((4-(bis(4-chlorophenyl)methyl)piperazin-1-yl) methyl)-4-(3-(dimethylamino)pyrrolidin-1-yl)benzonitrile
mass spectrum (ESI$^+$): m/z=548.2 (M+H)$^+$
(86) 2-((4-(bis(4-chlorophenyl)methyl)piperazin-1-yl) methyl)-4-(methyl(2-(pyrrolidin-1-yl)ethyl)amino) benzonitrile
mass spectrum (ESI$^+$): m/z=562.2 (M+H)$^+$
(87) 4-((2-(aziridin-1-yl)ethyl)(methyl)amino)-2-((4-(bis (4-chlorophenyl)methyl)piperazin-1-yl)methyl)benzonitrile
mass spectrum (ESI$^+$): m/z=534.2 (M+H)$^+$
(88) 2-((4-((4-chlorophenyl)(phenyl)methyl)piperazin-1-yl)methyl)-4-(4-methyl-1,4-diazepan-1-yl)benzonitrile
mass spectrum (ESI$^+$): m/z=514.3 (M+H)$^+$
(89) 2-((4-((4-chlorophenyl)(pyridin-4-yl)methyl)piperazin-1-yl)methyl)-4-(4-methyl-1,4-diazepan-1-yl)benzonitrile
mass spectrum (ESI$^+$): m/z=515.3 (M+H)$^+$
(90) 2-((4-(bis(4-chlorophenyl)methyl)piperidin-1-yl) methyl)-4-((2-(dimethylamino)ethyl)(methyl)amino) benzonitrile
mass spectrum (ESI$^+$): m/z=535.2 (M+H)$^+$
(91) 2-((4-(bis(4-fluorophenyl)methyl)piperidin-1-yl) methyl)-4-(4-methyl-1,4-diazepan-1-yl)benzonitrile
mass spectrum (ESI$^+$): m/z=515.3 (M+H)$^+$
(93) 4-[{2-[ethyl(methyl)amino]ethyl}(methyl)amino)-2-({4-[1-(pyrazin-2-yl)ethyl]piperazin-1-yl}methyl)benzonitrile
mass spectrum (ESI$^+$): m/z=422.3 (M+H)$^+$
(95) 2-({4-[bis(4-chloro-3-methylphenyl)methyl]piperazin-1-yl}methyl)-4-{[2-(dimethylamino)ethyl] (methyl)amino}benzonitrile
mass spectrum (ESI$^+$): m/z=564.3 (M+H)$^+$
(97) 2-({4-[(4-chlorophenyl)(cyclobutyl)methyl]piperazin-1-yl}methyl)-4-(4-methyl-1,4-diazepan-1-yl)benzonitrile
mass spectrum (ESI$^+$): m/z=492.3 (M+H)$^+$

(99) 4-(4-methylpiperazin-1-yl)-2-[(4-{(pyrazin-2-yl)[(4-(trifluoromethyl)phenyl]methyl}piperazin-1-yl)methyl]benzonitrile mass spectrum (ESI$^+$): m/z=536.3 (M+H)$^+$ (102) 2-({4-(bis(4-(methylthio)phenyl]methyl}piperazin-1-yl)methyl)-4-{[2-(dimethylamino)ethyl](methyl)amino}benzonitrile mass spectrum (ESI$^+$): m/z=560.3 (M+H)$^+$ (104) 2-({4-[(4-cyanophenyl)(cyclopentyl)methyl]piperazin-1-yl}methyl)-4-{[2-(dimethylamino)ethyl](methyl)amino}benzonitrile mass spectrum (ESI$^+$): m/z=485.3 (M+H)$^+$ (106) 4-([3-(1H-imidazol-1-yl)propyl]amino)-2-({4-[bis(4-chlorophenyl)methyl]piperazin-1-yl}methyl)benzonitrile mass spectrum (ESI$^+$): m/z=559.2 (M+H)$^+$

Example 3: Assay of the Anti-HCV Activity of the Compounds of the Present Invention 100 μL Huh7.5 cells were seeded at a density of $1\times10^5$/mL in a 96-well cell culture plate and incubated in an incubator at 37° C., 5% $CO_2$ and saturated humidity for 6 hrs. Then, while infecting Huh7.5 cells with viral solution containing HCV virus particles, the compounds of the present invention (including all specific compounds listed herein) were added at a concentration of 1 μM, respectively. After continuing incubation for 96 hrs, the total intracellular RNA was extracted separately, and the content of intracellular HCV RNA was measured by one-step quantitative RT-PCR, compared with the RNA level of the viral control, and the inhibition rate of the compounds against HCV was calculated. The results of some compounds are shown in Table 1.

The results of the anti-HCV activity assay of the compounds of the present invention and synthesized in cell culture are shown in Table 1

TABLE 1

Activity of compounds against HCV

| Number | chemical name | structures | inhibitory activities* | molecular weight# |
|---|---|---|---|---|
| 1 | 1-(3-((4-(1-(4-bromophenyl)ethyl)piperazin-1-yl)methyl)-4-(trifluoromethyl)phenyl)-4-methyl-1,4-diazepane | 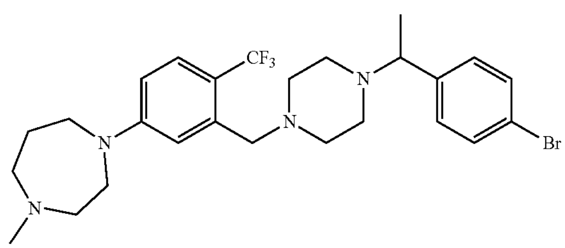 [SMILES: CC(c1ccc(Br)cc1)N1CCN(Cc2cc(N3CCCN(C)CC3)ccc2C(F)(F)F)CC1] | +++ | 539 |
| 2 | 1-(3-((4-(4-chlorobenzyl)piperazin-1-yl)methyl)-4-(trifluoromethyl)phenyl)-4-methyl-1,4-diazepane | 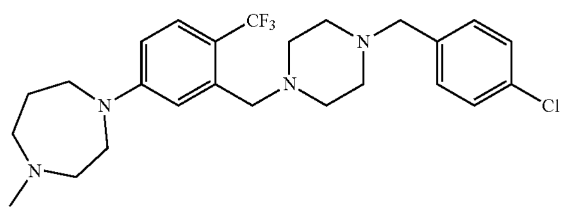 [SMILES: CN1CCCN(c2ccc(C(F)(F)F)c(CN3CCN(Cc4ccc(Cl)cc4)CC3)c2)CC1] | +++ | 481 |
| 3 | 1-(3-((4-(1-(3-chloro-4-fluorophenyl)ethyl)piperazin-1-yl)methyl)-4-(trifluoromethyl)phenyl)-4-methyl-1,4-diazepane | 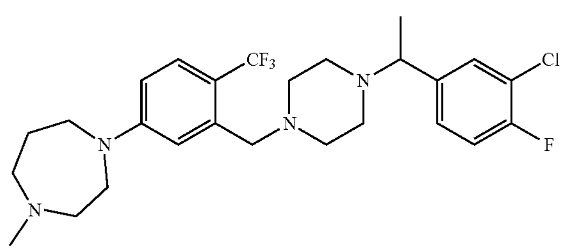 [SMILES: CC(c1ccc(F)c(Cl)c1)N1CCN(Cc2cc(N3CCCN(C)CC3)ccc2C(F)(F)F)CC1] | +++ | 513 |
| 4 | 1-(3-((4-(4-chloro-3-methylbenzyl)piperazin-1-yl)methyl)-4-(trifluoromethyl)phenyl)-4-methyl-1,4-diazepane | 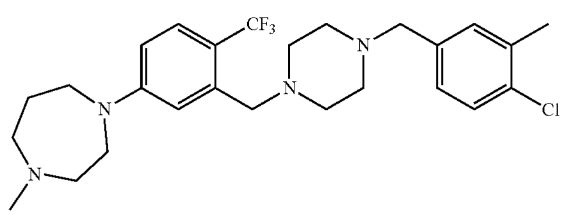 | +++ | 495 |

TABLE 1-continued

Activity of compounds against HCV

| Number | chemical name | structures | inhibitory activities* | molecular weight# |
|---|---|---|---|---|
| 5 | 1-(3-((4-(1-(4-methoxyphenyl)butyl)piperazin-1-yl)methyl)-4-(trifluoromethyl)phenyl)-4-methyl-1,4-diazepane | 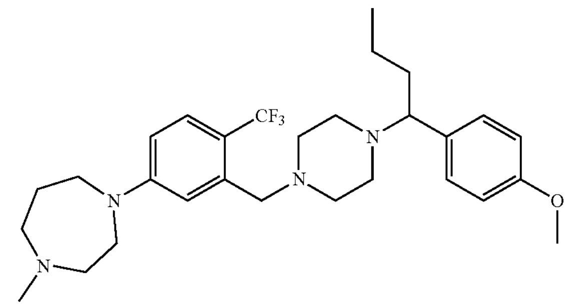 | +++ | 519 |
| 6 | 1-(3,4-dichlorobenzyl)-4-(5-(4-methylpiperazin-1-yl)-2-(trifluoromethyl)benzyl)piperazine | 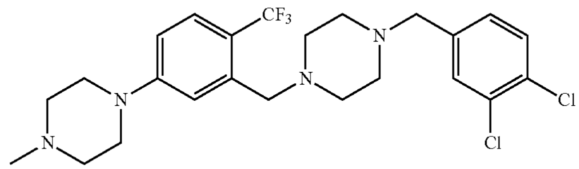 [SMILES: CN1CCN(c2ccc(C(F)(F)F)c(CN3CCN(Cc4ccc(Cl)c(Cl)c4)CC3)c2)CC1] | +++ | 501 |
| 7 | 1-(3-((4-(4-chlorobenzyl)piperidin-1-yl)methyl)-4-(trifluoromethyl)phenyl)-4-methyl-1,4-diazepane | 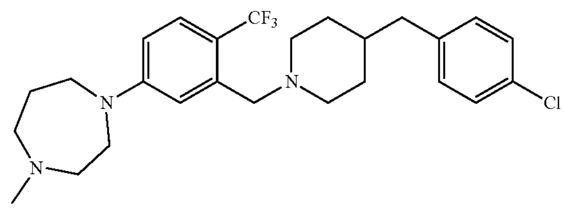 [SMILES: CN1CCCN(c2ccc(C(F)(F)F)c(CN3CCC(Cc4ccc(Cl)cc4)CC3)c2)CC1] | ++ | 480 |
| 8 | $N^1$-(3-((4-(1-(4-bromophenyl)propyl)piperazin-1-yl)methyl)-4-(trifluoromethyl)phenyl)-$N^1,N^2,N^2$-trimethylethan-1,2-diamine | 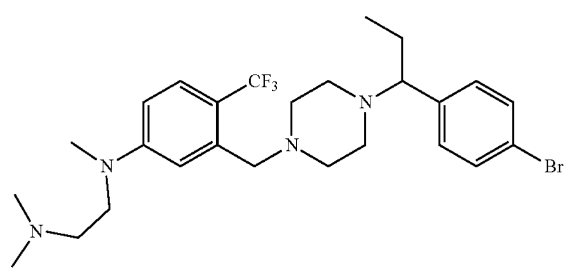 [SMILES: CCC(c1ccc(Br)cc1)N1CCN(Cc2cc(N(C)CCN(C)C)ccc2C(F)(F)F)CC1] | +++ | 542 |
| 9 | $N^1$-(3-((4-(1-(4-chlorophenyl)ethyl)piperazin-1-yl)methyl)-4-(trifluoromethyl)phenyl)-$N^1,N^2,N^2$-trimethylethan-1,2-diamine | 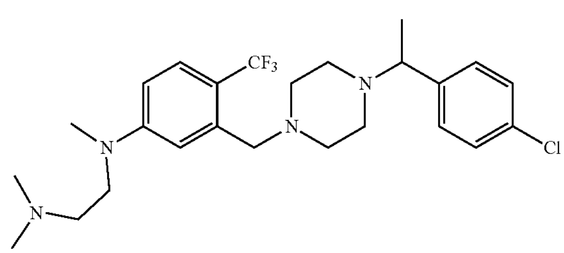 [SMILES: CC(c1ccc(Cl)cc1)N1CCN(Cc2cc(N(C)CCN(C)C)ccc2C(F)(F)F)CC1] | +++ | 483 |
| 10 | $N^1,N^1,N^2$-trimethyl-$N^2$-(3-((4-(4-methylbenzyl)piperazin-1-yl)methyl)-4-(trifluoromethyl)phenyl)ethan-1,2-diamine | 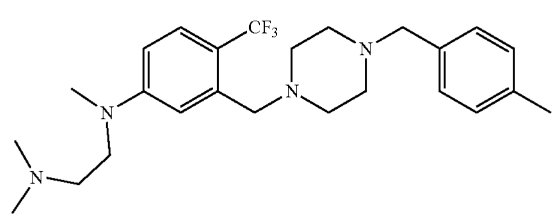 | ++ | 449 |

TABLE 1-continued

Activity of compounds against HCV

| Number | chemical name | structures | inhibitory activities* | molecular weight# |
|---|---|---|---|---|
| 11 | 2-((4-(4-chloro-3-methylbenzyl)piperazin-1-yl)methyl)-4-(4-ethylpiperazin-1-yl)benzonitrile | 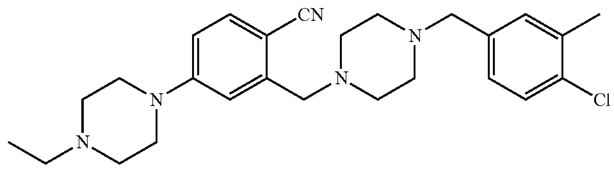 [SMILES: CCN1CCN(c2ccc(C#N)c(CN3CCN(Cc4ccc(Cl)c(C)c4)CC3)c2)CC1] | ++ | 452 |
| 12 | 2-((4-(4-chlorobenzyl)piperazin-1-yl)methyl)-4-(4-cyclopropylpiperazin-1-yl)benzonitrile | 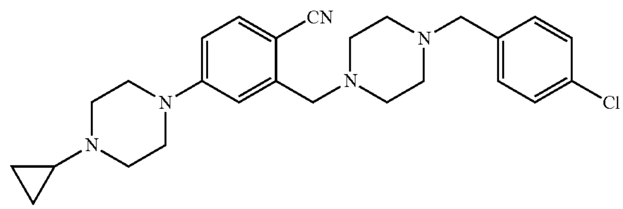 [SMILES: N#Cc1ccc(N2CCN(C3CC3)CC2)cc1CN1CCN(Cc2ccc(Cl)cc2)CC1] | ++ | 450 |
| 13 | 2-((4-(1-(4-chlorophenyl)ethyl)piperazin-1-yl)methyl)-4-((2-(ethyl(methyl)amino)ethyl)(methyl)amino)benzonitrile | 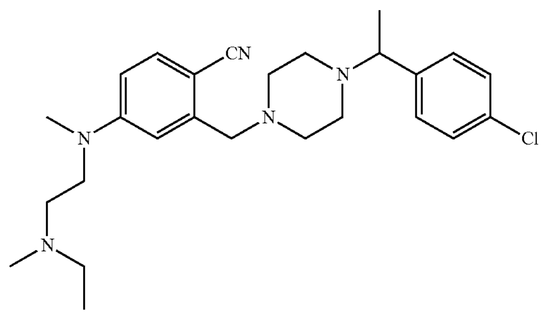 [SMILES: CCN(C)CCN(C)c1ccc(C#N)c(CN2CCN(C(C)c3ccc(Cl)cc3)CC2)c1] | +++ | 454 |
| 14 | 4-(3-(dimethylamino)piperidin-1-yl)-2-((4-(1-phenylethyl)piperazin-1-yl)methyl)benzonitrile | 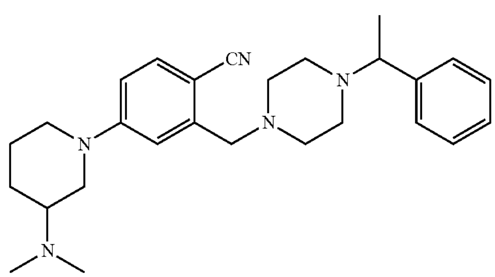 [SMILES: CC(c1ccccc1)N1CCN(Cc2cc(N3CCCC(N(C)C)C3)ccc2C#N)CC1] | ++ | 432 |
| 15 | 4-((2-(dimethylamino)ethyl)(methyl)amino)-2-((4-(1-(4-(trifluoromethyl)phenyl)ethyl)piperazin-1-yl)methyl)benzonitrile | 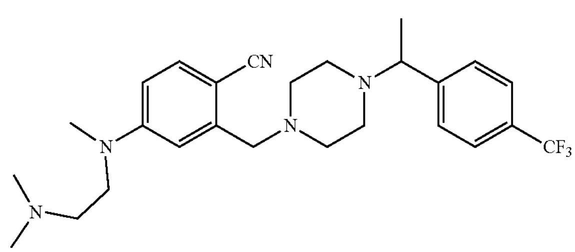 [SMILES: CC(c1ccc(C(F)(F)F)cc1)N1CCN(Cc2cc(N(C)CCN(C)C)ccc2C#N)CC1] | +++ | 474 |
| 16 | 2-((4-(1-(4-chlorophenyl)-2-methylpropyl)piperazin-1-yl)methyl)-4-(methyl(2-(pyrrolidin-1-yl)ethyl)amino)benzonitrile | 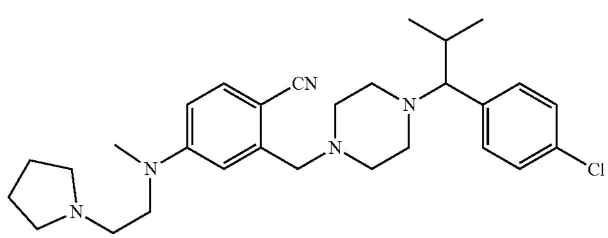 [SMILES: CC(C)C(c1ccc(Cl)cc1)N1CCN(Cc2cc(N(C)CCN3CCCC3)ccc2C#N)CC1] | +++ | 494 |

TABLE 1-continued

Activity of compounds against HCV

| Number | chemical name | structures | inhibitory activities* | molecular weight# |
|---|---|---|---|---|
| 17 | 2-((4-(3-chloro-4-fluorobenzyl)piperazin-1-yl)methyl)-4-((2-(diethylamino)ethyl)(methyl)amino)benzonitrile | 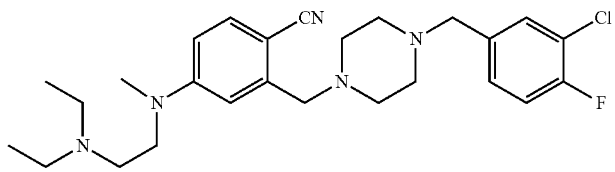 [SMILES: CCN(CC)CCN(C)c1ccc(C#N)c(CN2CCN(Cc3ccc(F)c(Cl)c3)CC2)c1] | +++ | 472 |
| 18 | 4-((3-(1H-pyrrol-1-yl)propyl)amino)-2-((4-(3,4-dichlorobenzyl)piperazin-1-yl)methyl)benzonitrile | 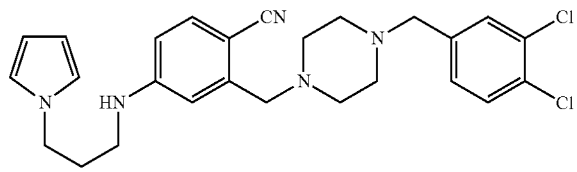 [SMILES: N#Cc1ccc(NCCCn2cccc2)cc1CN1CCN(Cc2ccc(Cl)c(Cl)c2)CC1] | +++ | 482 |
| 19 | $N^1$-(3-((4-(4-chlorophenyl)piperazin-1-yl)methyl)-4-(trifluoromethyl)phenyl)-$N^1,N^2,N^2$-trimethylethan-1,2-diamine | 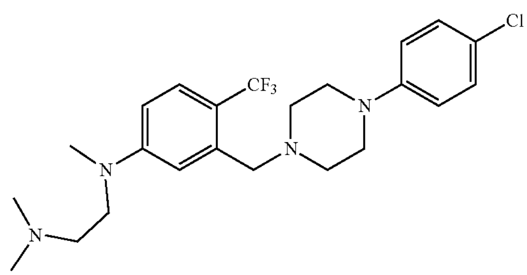 [SMILES: CN(C)CCN(C)c1ccc(C(F)(F)F)c(CN2CCN(c3ccc(Cl)cc3)CC2)c1] | +++ | 455 |
| 20 | $N^1$-(3-((4-(4-bromophenyl)piperazin-1-yl)methyl)-4-(trifluoromethyl)phenyl)-$N^1,N^2,N^2$-trimethylethan-1,2-diamine | 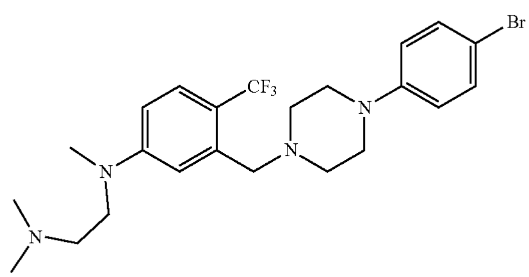 [SMILES: CN(C)CCN(C)c1ccc(C(F)(F)F)c(CN2CCN(c3ccc(Br)cc3)CC2)c1] | +++ | 499 |
| 21 | 3-((4-(4-chlorophenyl)piperazin-1-yl)methyl)-N-methyl-N-((1-methylpiperidin-2-yl)methyl)-4-(trifluoromethyl)aniline | 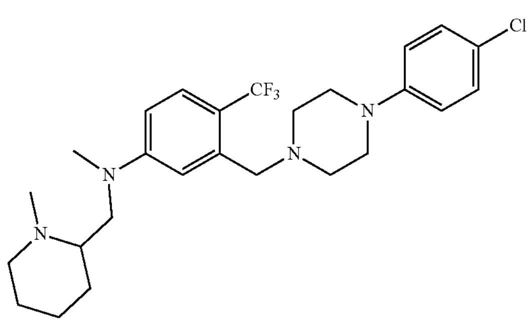 [SMILES: CN(CC1CCCCN1C)c1ccc(C(F)(F)F)c(CN2CCN(c3ccc(Cl)cc3)CC2)c1] | +++ | 495 |
| 22 | 1-(3-((4-(4-chlorophenyl)-2-methylpiperazin-1-yl)methyl)-4-(trifluoromethyl)phenyl)-4-methyl-1,4-diazepane | 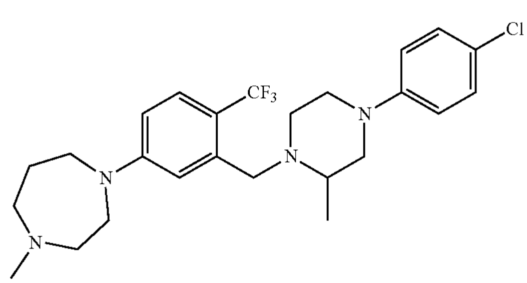 [SMILES: CC1CN(c2ccc(Cl)cc2)CCN1Cc1cc(N2CCCN(C)CC2)ccc1C(F)(F)F] | +++ | 481 |

TABLE 1-continued

Activity of compounds against HCV

| Number | chemical name | structures | inhibitory activities* | molecular weight# |
|---|---|---|---|---|
| 23 | 1-(3-((4-(4-chlorophenyl)piperazin-1-yl)methyl)-4-(trifluoromethyl)phenyl)-4-methyl-1,4-diazepane | 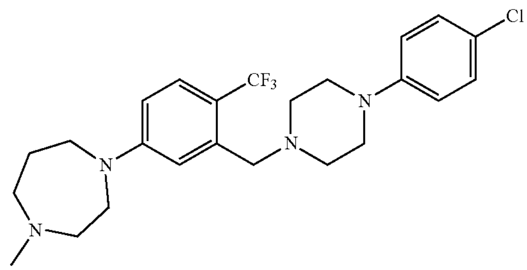 [SMILES: CN1CCCN(c2ccc(C(F)(F)F)c(CN3CCN(c4ccc(Cl)cc4)CC3)c2)CC1] | +++ | 467 |
| 24 | 3-((4-(4-bromophenyl)piperazin-1-yl)methyl)-N-methyl-N-((1-methylpyrrolidin-2-yl)methyl)-4-(trifluoromethyl)aniline | 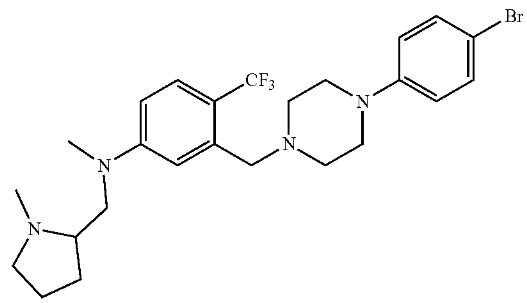 [SMILES: CN(CC1CCCN1C)c1ccc(C(F)(F)F)c(CN2CCN(c3ccc(Br)cc3)CC2)c1] | +++ | 525 |
| 25 | 3-((4-(4-chlorophenyl)piperazin-1-yl)methyl)-N-((1-ethylpyrrolidin-2-yl)methyl)-N-methyl-4-(trifluoromethyl)aniline | 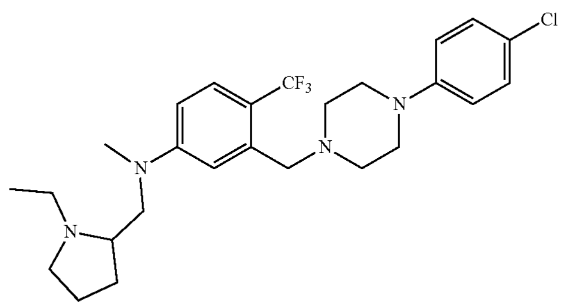 [SMILES: CCN1CCCC1CN(C)c1ccc(C(F)(F)F)c(CN2CCN(c3ccc(Cl)cc3)CC2)c1] | +++ | 495 |
| 26 | $N^1$-(3-((4-(4-bromo-3-chlorophenyl)piperazin-1-yl)methyl)-4-(trifluoromethyl)phenyl)-$N^1$,$N^2$,$N^2$-trimethylethan-1,2-diamine | 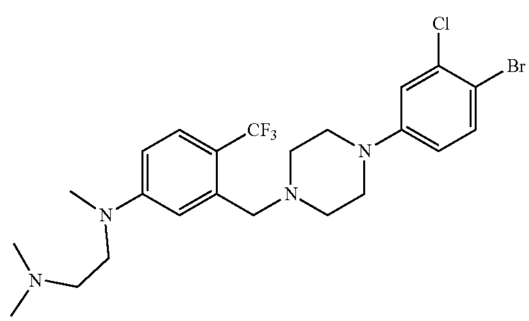 [SMILES: CN(C)CCN(C)c1ccc(C(F)(F)F)c(CN2CCN(c3ccc(Br)c(Cl)c3)CC2)c1] | +++ | 534 |
| 27 | 1-(3-((4-(4-chlorophenyl)piperazin-1-yl)methyl)-4-(trifluoromethyl)phenyl)-N,N-dimethylpiperidin-4-amine | 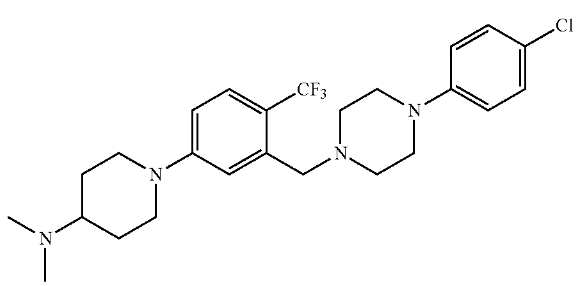 [SMILES: CN(C)C1CCN(c2ccc(C(F)(F)F)c(CN3CCN(c4ccc(Cl)cc4)CC3)c2)CC1] | +++ | 481 |

TABLE 1-continued

Activity of compounds against HCV

| Number | chemical name | structures | inhibitory activities* | molecular weight# |
|---|---|---|---|---|
| 28 | 1-(4-chlorophenyl)-4-(5-(4-(pyrrolidin-1-yl)piperidin-1-yl)-2-(trifluoromethyl)benzyl)piperazine | 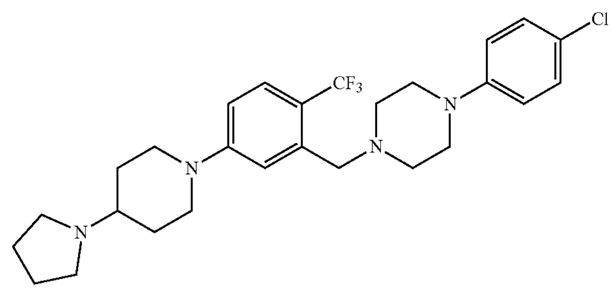 [SMILES: FC(F)(F)c1ccc(N2CCC(N3CCCC3)CC2)cc1CN1CCN(c2ccc(Cl)cc2)CC1] | +++ | 507 |
| 29 | 1-(3-((4-(4-chlorophenyl)piperazin-1-yl)methyl)-4-(trifluoromethyl)phenyl)-N,N-dimethylpyrrolidin-3-amine | 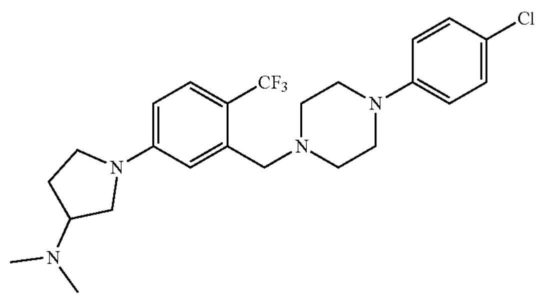 [SMILES: CN(C)C1CCN(c2ccc(C(F)(F)F)c(CN3CCN(c4ccc(Cl)cc4)CC3)c2)C1] | +++ | 467 |
| 30 | 1-(4-chlorophenyl)-4-(5-(4-methylpiperazin-1-yl)-2-(trifluoromethyl)benzyl)piperazine | 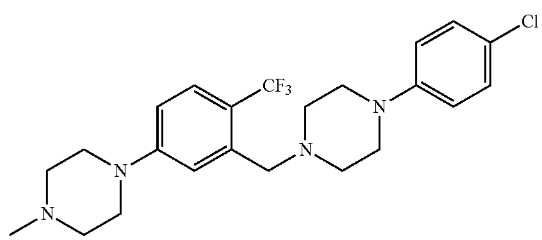 [SMILES: CN1CCN(c2ccc(C(F)(F)F)c(CN3CCN(c4ccc(Cl)cc4)CC3)c2)CC1] | +++ | 453 |
| 31 | 3-((4-(4-chlorophenyl)-2-methylpiperazin-1-yl)methyl)-N-methyl-N-(piperidin-1-ylmethyl)-4-(trifluoromethyl)aniline | 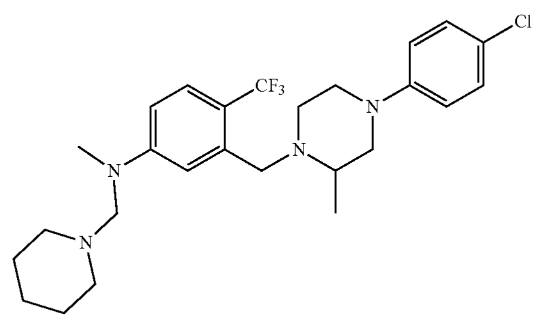 [SMILES: CC1CN(c2ccc(Cl)cc2)CCN1Cc1cc(N(C)CN2CCCCC2)ccc1C(F)(F)F] | +++ | 495 |
| 32 | 1-(3-((4-(4-chloro-3-(trifluoromethyl)phenyl)-2-methylpiperazin-1-yl)methyl)-4-(trifluoromethyl)phenyl)-4-methyl-1,4-diazepane | 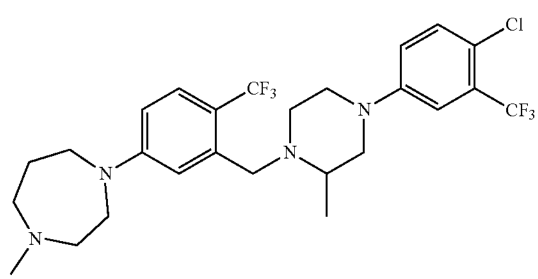 [SMILES: CC1CN(c2ccc(Cl)c(C(F)(F)F)c2)CCN1Cc1cc(N2CCCN(C)CC2)ccc1C(F)(F)F] | +++ | 549 |

TABLE 1-continued

Activity of compounds against HCV

| Number | chemical name | structures | inhibitory activities* | molecular weight# |
|---|---|---|---|---|
| 33 | $N^1$-(3-((4-(4-bromo-3-(trifluoromethyl)phenyl)-2-methylpiperazin-1-yl)methyl)-4-(trifluoromethyl)phenyl)-$N^1,N^2,N^2$-trimethylethan-1,2-diamine | 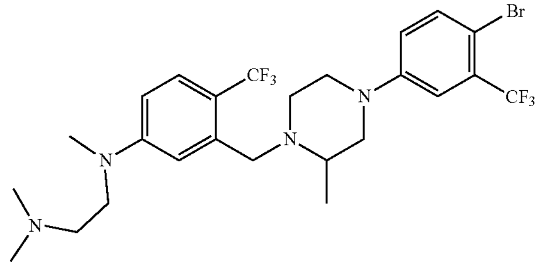 [SMILES: CC1CN(c2ccc(Br)c(C(F)(F)F)c2)CCN1Cc1cc(N(C)CCN(C)C)ccc1C(F)(F)F] | +++ | 581 |
| 34 | 1-methyl-4-(3-((2-propyl-4-(4-(trifluoromethyl)phenyl)piperazin-1-yl)methyl)-4-(trifluoromethyl)phenyl)-1,4-diazepane | 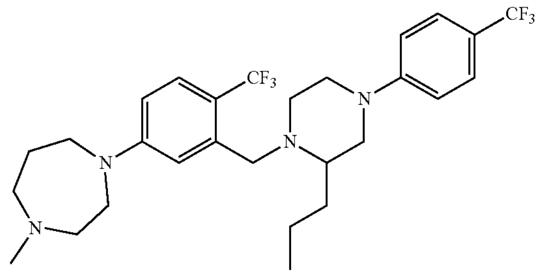 [SMILES: CCCC1CN(c2ccc(C(F)(F)F)cc2)CCN1Cc1cc(N2CCCN(C)CC2)ccc1C(F)(F)F] | +++ | 543 |
| 35 | 1-(3-((4-(3-chloro-4-methylphenyl)piperazin-1-yl)methyl)-4-(trifluoromethyl)phenyl)-4-ethyl-1,4-diazepane | 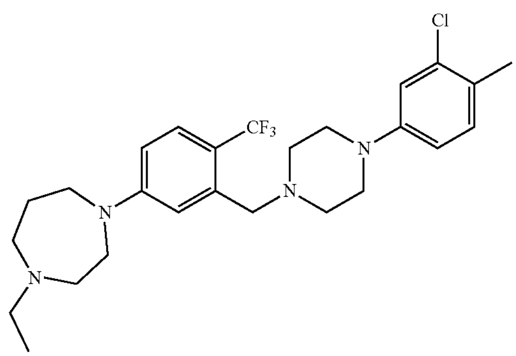 [SMILES: CCN1CCCN(c2ccc(C(F)(F)F)c(CN3CCN(c4ccc(C)c(Cl)c4)CC3)c2)CC1] | +++ | 495 |
| 36 | 1-(3-((4-(4-fluorophenyl)piperazin-1-yl)methyl)-4-(trifluoromethyl)phenyl)-4-methyl-1,4-diazepane | 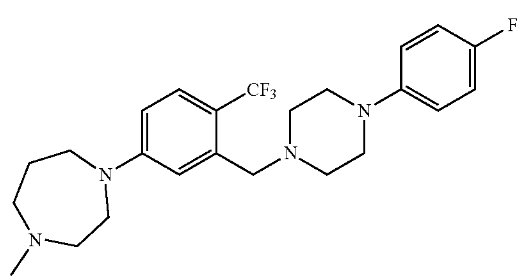 [SMILES: CN1CCCN(c2ccc(C(F)(F)F)c(CN3CCN(c4ccc(F)cc4)CC3)c2)CC1] | +++ | 451 |
| 37 | 1-(3-((4-(3-chloro-4-fluorophenyl)piperazin-1-yl)methyl)-4-(trifluoromethyl)phenyl)-4-methyl-1,4-diazepane | 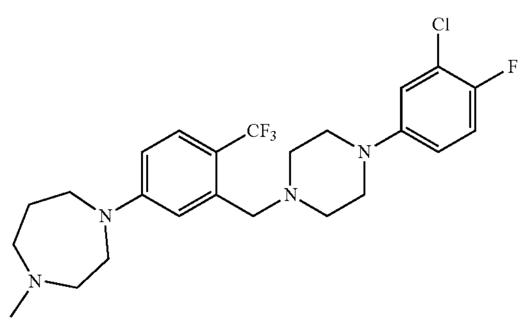 [SMILES: CN1CCCN(c2ccc(C(F)(F)F)c(CN3CCN(c4ccc(F)c(Cl)c4)CC3)c2)CC1] | +++ | 485 |

TABLE 1-continued

Activity of compounds against HCV

| Number | chemical name | structures | inhibitory activities* | molecular weight# |
|---|---|---|---|---|
| 38 | N¹-(3-((4-(4-bromo-3-chlorophenyl)piperazin-1-yl)methyl)-4-(trifluoromethyl)phenyl)-N¹,N²,N²-trimethylethan-1,2-diamine | 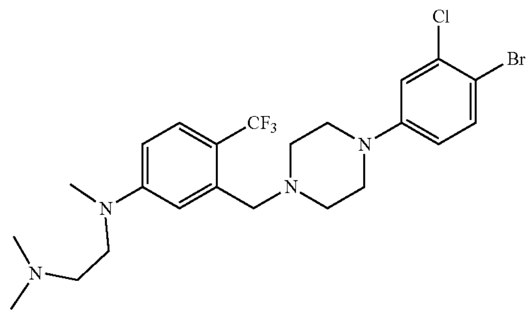 [SMILES: CN(C)CCN(C)c1ccc(C(F)(F)F)c(CN2CCN(c3ccc(Br)c(Cl)c3)CC2)c1] | +++ | 534 |
| 39 | 3-((4-(4-chlorophenyl)piperidin-1-yl)methyl)-N-methyl-N-(2-(pyrrolidin-1-yl)ethyl)-4-(trifluoromethyl)aniline | 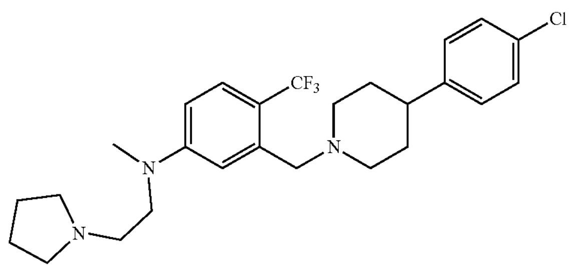 [SMILES: CN(CCN1CCCC1)c1ccc(C(F)(F)F)c(CN2CCC(c3ccc(Cl)cc3)CC2)c1] | +++ | 480 |
| 40 | 1-(3-((4-(4-chloro-3-methylphenyl)piperazin-1-yl)methyl)-4-(trifluoromethyl)phenyl)-4-methyl-1,4-diazepane | 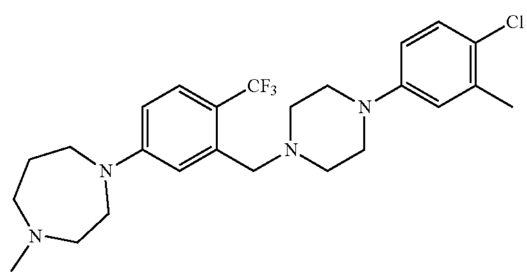 | +++ | 481 |
| 41 | N¹-(3-((4-(4-chloro-3-fluorophenyl)piperazin-1-yl)methyl)-4-(trifluoromethyl)phenyl)-N¹,N²,N²-trimethylethan-1,2-diamine | 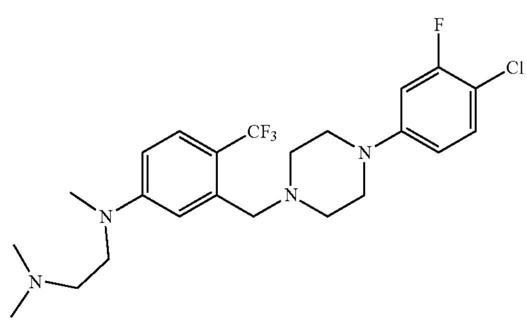 [SMILES: CN(C)CCN(C)c1ccc(C(F)(F)F)c(CN2CCN(c3ccc(Cl)c(F)c3)CC2)c1] | +++ | 473 |
| 42 | N¹-(3-((4-(3,4-dichlorophenyl)piperidin-1-yl)methyl)-4-(trifluoromethyl)phenyl)-N¹,N²,N²-trimethylethan-1,2-diamine | 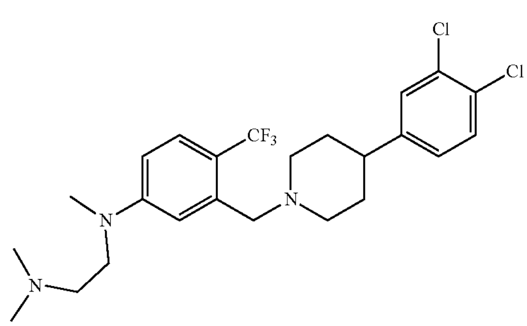 [SMILES: CN(C)CCN(C)c1ccc(C(F)(F)F)c(CN2CCC(c3ccc(Cl)c(Cl)c3)CC2)c1] | +++ | 488 |

TABLE 1-continued

Activity of compounds against HCV

| Number | chemical name | structures | inhibitory activities* | molecular weight# |
|---|---|---|---|---|
| 43 | 1-(3-((4-(4-chloro-3-methylphenyl)piperidin-1-yl)methyl)-4-(trifluoromethyl)phenyl)-4-methyl-1,4-diazepane | 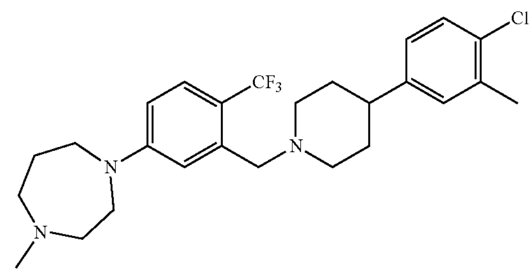 | +++ | 480 |
| 44 | 1-(3-((4-(bis(4-fluorophenyl)methyl)piperazin-1-yl)methyl)-4-(trifluoromethyl)phenyl)-4-methyl-1,4-diazepane | 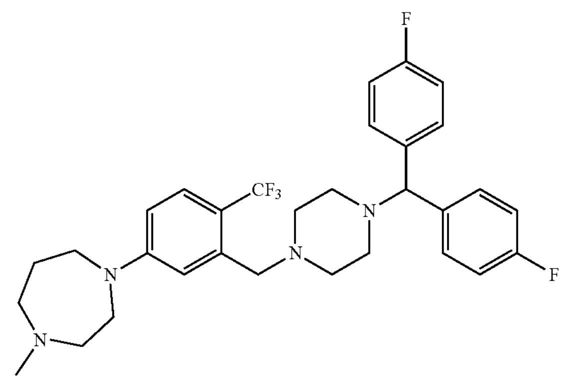 [SMILES: CN1CCCN(c2ccc(C(F)(F)F)c(CN3CCN(C(c4ccc(F)cc4)c4ccc(F)cc4)CC3)c2)CC1] | +++ | 559 |
| 45 | 1-(3-((4-(bis(4-methylphenyl)methyl)piperazin-1-yl)methyl)-4-(trifluoromethyl)phenyl)-4-methyl-1,4-diazepane | 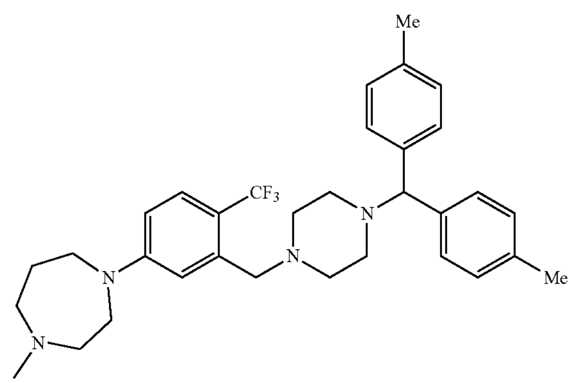 [SMILES: Cc1ccc(C(c2ccc(C)cc2)N2CCN(Cc3cc(N4CCCN(C)CC4)ccc3C(F)(F)F)CC2)cc1] | +++ | 551 |
| 46 | 1-(3-((4-(bis(4-chlorophenyl)methyl)piperazin-1-yl)methyl)-4-(trifluoromethyl)phenyl)-4-methyl-1,4-diazepane | 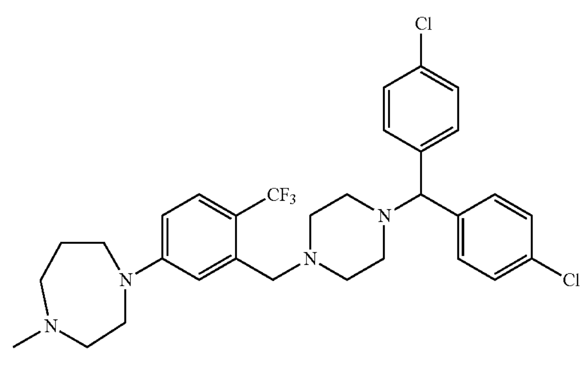 [SMILES: CN1CCCN(c2ccc(C(F)(F)F)c(CN3CCN(C(c4ccc(Cl)cc4)c4ccc(Cl)cc4)CC3)c2)CC1] | +++ | 592 |

TABLE 1-continued

Activity of compounds against HCV

| Number | chemical name | structures | inhibitory activities* | molecular weight# |
|---|---|---|---|---|
| 47 | 1-(3-((4-(bis(4-bromophenyl)methyl)piperazin-1-yl)methyl)-4-(trifluoromethyl)phenyl)-4-methyl-1,4-diazepane | 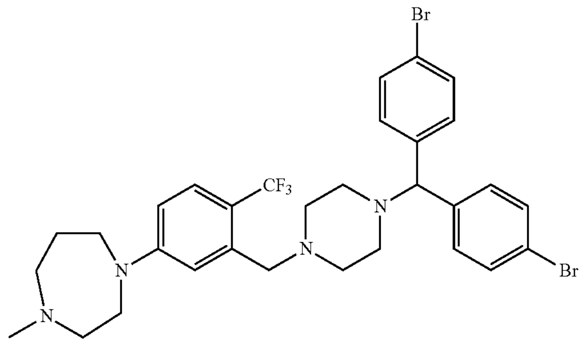 [SMILES: CN1CCCN(c2ccc(C(F)(F)F)c(CN3CCN(C(c4ccc(Br)cc4)c4ccc(Br)cc4)CC3)c2)CC1] | +++ | 680 |
| 48 | 1-(3-((4-(bis(4-isopropylphenyl)methyl)piperazin-1-yl)methyl)-4-(trifluoromethyl)phenyl)-4-methyl-1,4-diazepane | 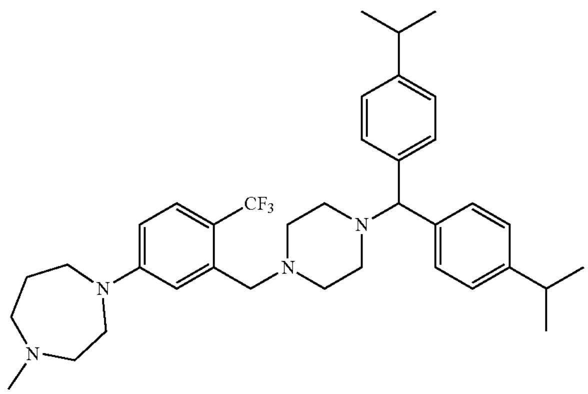 [SMILES: CC(C)c1ccc(C(c2ccc(C(C)C)cc2)N2CCN(Cc3cc(N4CCCN(C)CC4)ccc3C(F)(F)F)CC2)cc1] | +++ | 607 |
| 49 | $N^1$-(3-((4-(bis(4-cyclopropylphenyl)methyl)piperazin-1-yl)methyl)-4-(trifluoromethyl)phenyl)-$N^1,N^2,N^2$-trimethylethan-1,2-diamine | 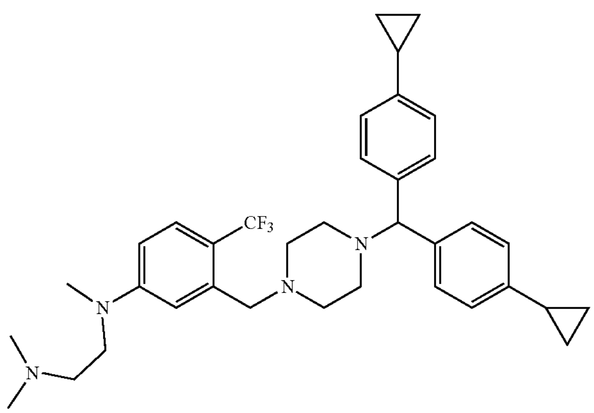 | +++ | 591 |
| 50 | N-(2-(azetidin-1-yl)ethyl)-3-((4-(bis(4-chlorophenyl)methyl)piperazin-1-yl)methyl)-N-methyl-4-(trifluoromethyl)aniline | 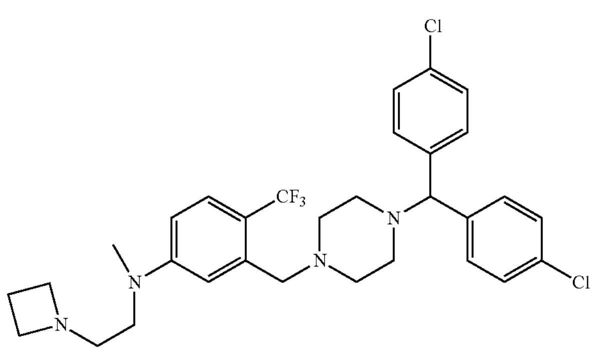 [SMILES: CN(CCN1CCC1)c1ccc(C(F)(F)F)c(CN2CCN(C(c3ccc(Cl)cc3)c3ccc(Cl)cc3)CC2)c1] | ++ | 592 |

TABLE 1-continued

Activity of compounds against HCV

| Number | chemical name | structures | inhibitory activities* | molecular weight# |
|---|---|---|---|---|
| 51 | 1-(3-((4-((4-fluorophenyl)(phenyl)methyl)piperazin-1-yl)methyl)-4-(trifluoromethyl)phenyl)-4-methyl-1,4-diazepane | 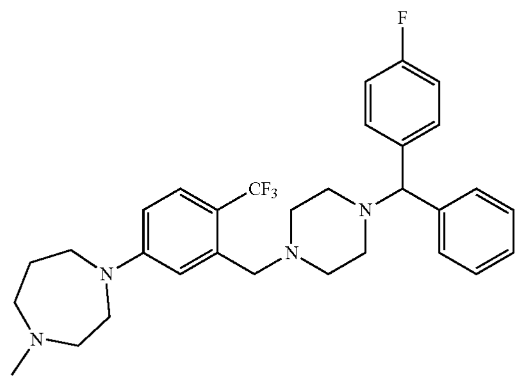 [SMILES: CN1CCCN(c2ccc(C(F)(F)F)c(CN3CCN(C(c4ccccc4)c4ccc(F)cc4)CC3)c2)CC1] | +++ | 541 |
| 52 | $N^1$-(3-((4-(bis(4-chlorophenyl)methyl)piperazin-1-yl)methyl)-4-(trifluoromethyl)phenyl)-$N^1,N^2,N^2$-trimethylethan-1,2-diamine | 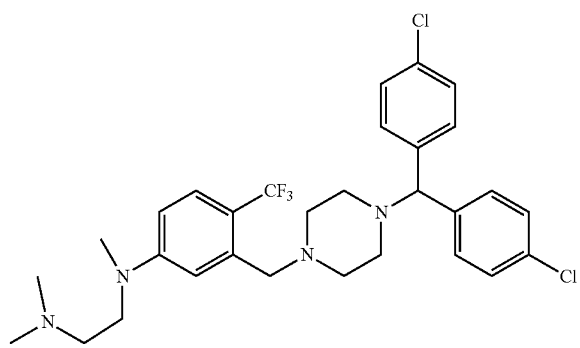 [SMILES: CN(C)CCN(C)c1ccc(C(F)(F)F)c(CN2CCN(C(c3ccc(Cl)cc3)c3ccc(Cl)cc3)CC2)c1] | +++ | 580 |
| 53 | $N^1$-(3-((4-(bis(4-(trifluoromethyl)phenyl)methyl)piperazin-1-yl)methyl)-4-(trifluoromethyl)phenyl)-$N^1,N^2,N^2$-trimethylethan-1,2-diamine | 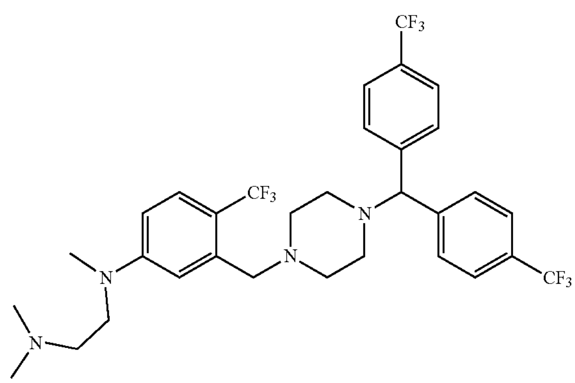 [SMILES: CN(C)CCN(C)c1ccc(C(F)(F)F)c(CN2CCN(C(c3ccc(C(F)(F)F)cc3)c3ccc(C(F)(F)F)cc3)CC2)c1] | +++ | 647 |
| 54 | $N^1$-(3-((4-((4-chlorophenyl)(phenyl)methyl)piperazin-1-yl)methyl)-4-(trifluoromethyl)phenyl)-$N^1,N^2,N^2$-trimethylethan-1,2-diamine | 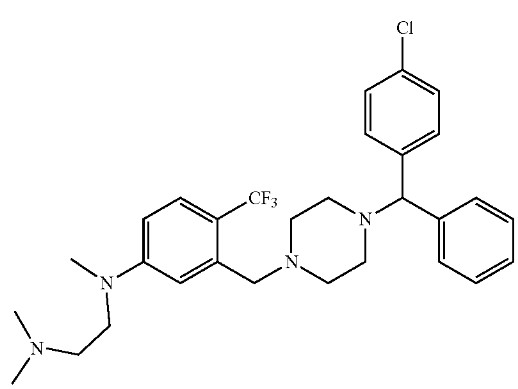 [SMILES: CN(C)CCN(C)c1ccc(C(F)(F)F)c(CN2CCN(C(c3ccccc3)c3ccc(Cl)cc3)CC2)c1] | +++ | 545 |

TABLE 1-continued

Activity of compounds against HCV

| Number | chemical name | structures | inhibitory activities* | molecular weight# |
|---|---|---|---|---|
| 55 | 1-(bis(4-chlorophenyl)methyl)-4-(5-(4-methylpiperazin-1-yl)-2-(trifluoromethyl)benzyl)piperazine | 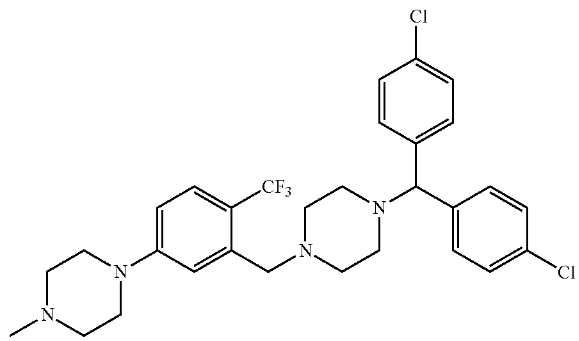 | +++ | 578 |
| 56 | 1-(3-((4-((4-chlorophenyl)(pyridin-2-yl)methyl)piperazin-1-yl)methyl)-4-(trifluoromethyl)phenyl)-4-methyl-1,4-diazepane | 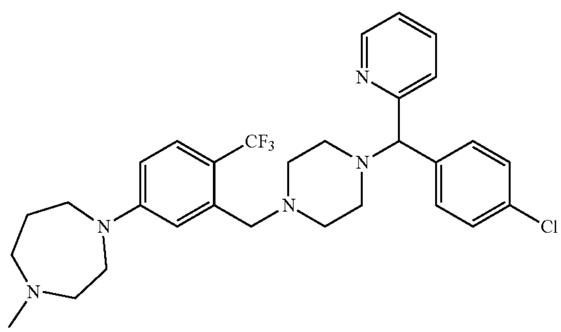 [SMILES: CN1CCCN(c2ccc(C(F)(F)F)c(CN3CCN(C(c4ccc(Cl)cc4)c4ccccn4)CC3)c2)CC1] | ++ | 558 |
| 57 | 1-methyl-4-(3-((4-(phenyl(pyridin-2-yl)methyl)piperazin-1-yl)methyl)-4-(trifluoromethyl)phenyl)-1,4-diazepane | 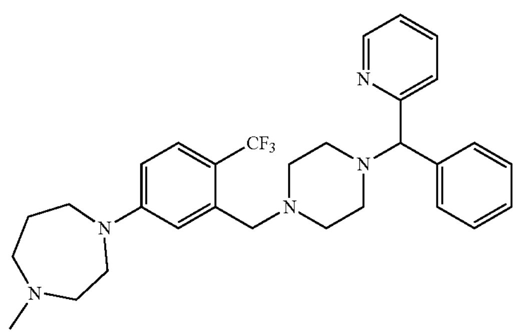 [SMILES: CN1CCCN(c2ccc(C(F)(F)F)c(CN3CCN(C(c4ccccc4)c4ccccn4)CC3)c2)CC1] | ++ | 524 |
| 58 | $N^1$-(3-((4-(bis(4-methoxyphenyl)methyl)piperazin-1-yl)methyl)-4-(trifluoromethyl)phenyl)-$N^1,N^2,N^2$-trimethylethan-1,2-diamine | 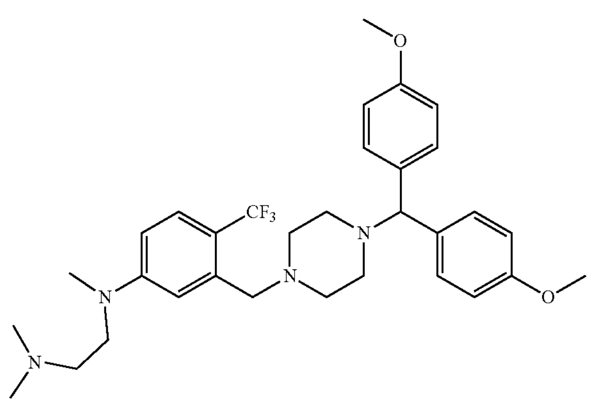 | +++ | 571 |

TABLE 1-continued

Activity of compounds against HCV

| Number | chemical name | structures | inhibitory activities* | molecular weight# |
|---|---|---|---|---|
| 59 | $N^1$-(3-((4-(bis(4-chlorophenyl)methyl)piperazin-1-yl)methyl)-4-(trifluoromethyl)phenyl)-$N^2$,$N^2$-dimethyl-$N^1$-propylethan-1,2-diamine | 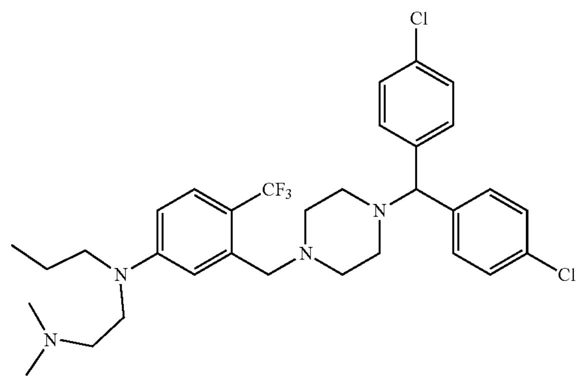 [SMILES: CCCN(CCN(C)C)c1ccc(C(F)(F)F)c(CN2CCN(C(c3ccc(Cl)cc3)c3ccc(Cl)cc3)CC2)c1] | +++ | 608 |
| 60 | 1-(3-((4-(bis(4-fluorophenyl)methyl)-2-methylpiperazin-1-yl)methyl)-4-(trifluoromethyl)phenyl)-4-methyl-1,4-diazepane | 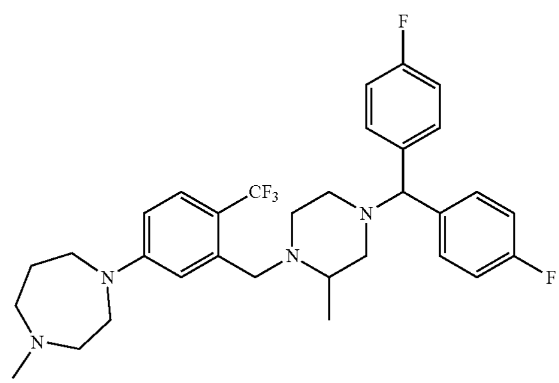 [SMILES: CC1CN(C(c2ccc(F)cc2)c2ccc(F)cc2)CCN1Cc1cc(N2CCCN(C)CC2)ccc1C(F)(F)F] | +++ | 573 |
| 61 | 1-(3-((4-(bis(4-chlorophenyl)methyl)-2-methylpiperazin-1-yl)methyl)-4-(trifluoromethyl)phenyl)-4-methyl-1,4-diazepane | 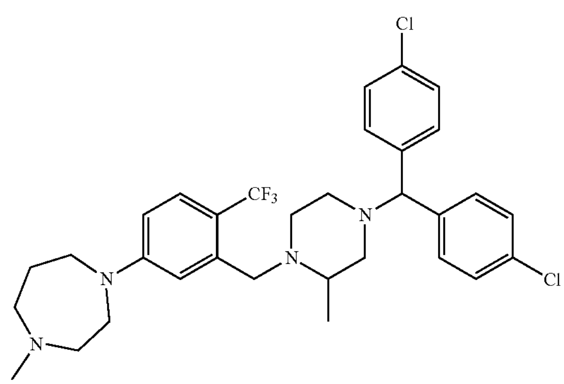 [SMILES: CC1CN(C(c2ccc(Cl)cc2)c2ccc(Cl)cc2)CCN1Cc1cc(N2CCCN(C)CC2)ccc1C(F)(F)F] | +++ | 606 |

TABLE 1-continued

Activity of compounds against HCV

| Number | chemical name | structures | inhibitory activities* | molecular weight# |
|---|---|---|---|---|
| 62 | 3-((4-(bis(4-chlorophenyl)methyl)piperazin-1-yl)methyl)-N-methyl-N-((1-methylpyrrolidin-2-yl)methyl)-4-(trifluoromethyl)aniline | 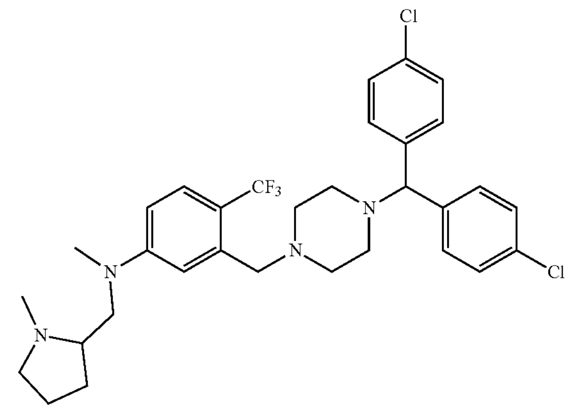 [SMILES: CN(CC1CCCN1C)c1ccc(C(F)(F)F)c(CN2CCN(C(c3ccc(Cl)cc3)c3ccc(Cl)cc3)CC2)c1] | +++ | 606 |
| 63 | 3-((4-(bis(4-chlorophenyl)methyl)piperazin-1-yl)methyl)-N-methyl-N-(2-(pyrrolidin-1-yl)ethyl)-4-(trifluoromethyl)aniline | 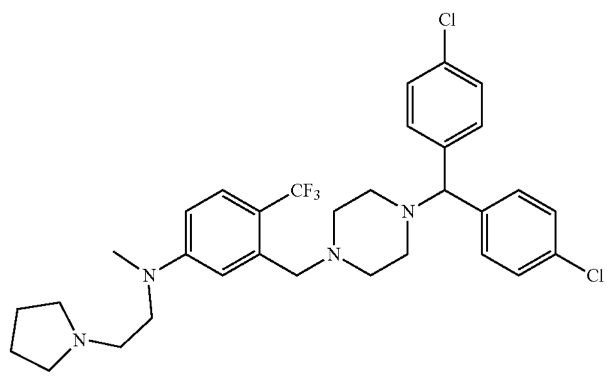 | +++ | 606 |
| 64 | N-(2-(aziridin-1-yl)ethyl)-3-((4-(bis(4-chlorophenyl)methyl)piperazin-1-yl)methyl)-N-methyl-4-(trifluoromethyl)aniline | 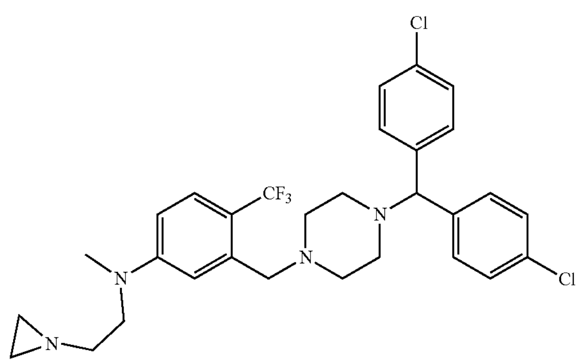 [SMILES: CN(CCN1CC1)c1ccc(C(F)(F)F)c(CN2CCN(C(c3ccc(Cl)cc3)c3ccc(Cl)cc3)CC2)c1] | +++ | 578 |
| 65 | 1-(3-((4-(di(pyridin-2-yl)methyl)piperazin-1-yl)methyl)-4-(trifluoromethyl)phenyl)-4-ethyl-1,4-diazepane | 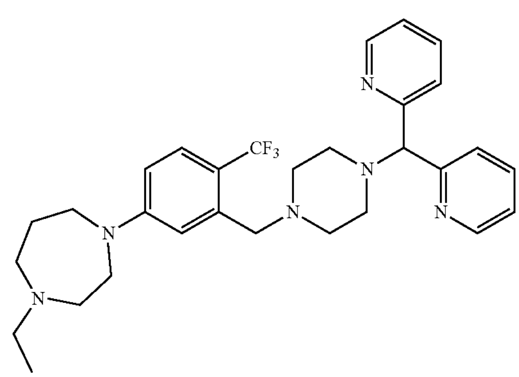 [SMILES: CCN1CCCN(c2ccc(C(F)(F)F)c(CN3CCN(C(c4ccccn4)c4ccccn4)CC3)c2)CC1] | ++ | 539 |

TABLE 1-continued

Activity of compounds against HCV

| Number | chemical name | structures | inhibitory activities* | molecular weight# |
|---|---|---|---|---|
| 66 | N¹-(3-((4-(bis(4-fluorophenyl)methyl)piperazin-1-yl)methyl)-4-(trifluoromethyl)phenyl)-N¹,N²,N²-trimethylethan-1,2-diamine | 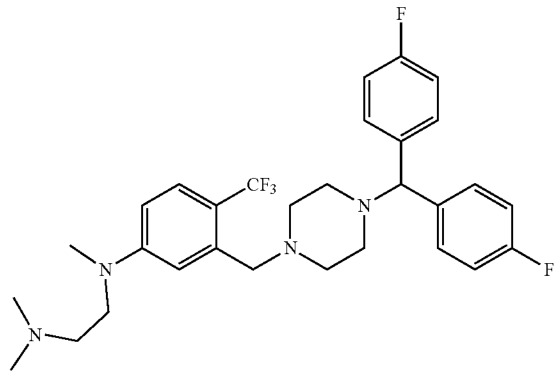 [SMILES: CN(C)CCN(C)c1ccc(C(F)(F)F)c(CN2CCN(C(c3ccc(F)cc3)c3ccc(F)cc3)CC2)c1] | +++ | 547 |
| 67 | 1-(3-((4-(bis(4-chlorophenyl)methyl)piperazin-1-yl)methyl)-4-(trifluoromethyl)phenyl)-N,N-dimethylpiperidin-3-amine | 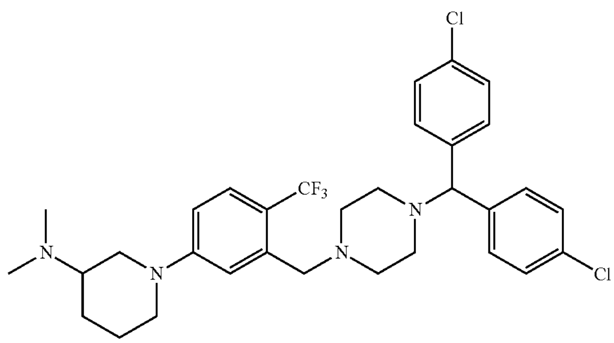 [SMILES: CN(C)C1CCCN(c2ccc(C(F)(F)F)c(CN3CCN(C(c4ccc(Cl)cc4)c4ccc(Cl)cc4)CC3)c2)C1] | +++ | 606 |
| 68 | 1-(bis(4-bromophenyl)methyl)-4-(5-(4-methylpiperazin-1-yl)-2-(trifluoromethyl)benzyl)piperazine | 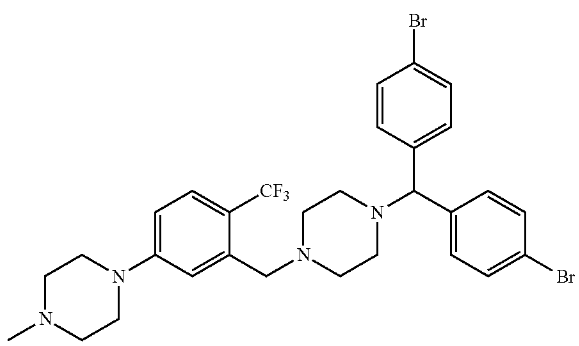 [SMILES: CN1CCN(c2ccc(C(F)(F)F)c(CN3CCN(C(c4ccc(Br)cc4)c4ccc(Br)cc4)CC3)c2)CC1] | +++ | 666 |
| 69 | 1-(3-((4-(bis(4-fluorophenyl)methyl)piperazin-1-yl)methyl)-4-(trifluoromethyl)phenyl)-N,N-dimethylpiperidin-4-amine | 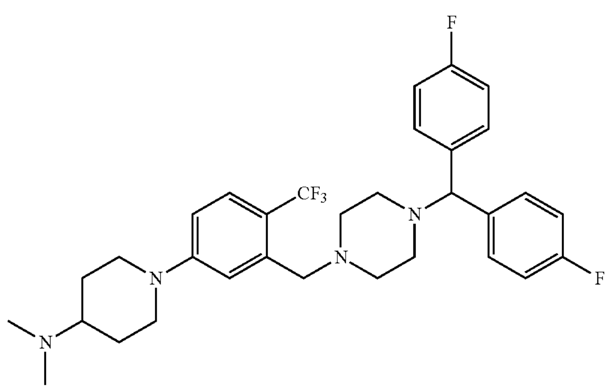 [SMILES: CN(C)C1CCN(c2ccc(C(F)(F)F)c(CN3CCN(C(c4ccc(F)cc4)c4ccc(F)cc4)CC3)c2)CC1] | +++ | 573 |

TABLE 1-continued

Activity of compounds against HCV

| Number | chemical name | structures | inhibitory activities* | molecular weight# |
|---|---|---|---|---|
| 70 | $N^1$-(3-((4-(bis(4-chlorophenyl)methyl)piperazin-1-yl)methyl)-4-(trifluoromethyl)phenyl)-$N^1,N^2$-dimethyl-$N^2$-propylethan-1,2-diamine | 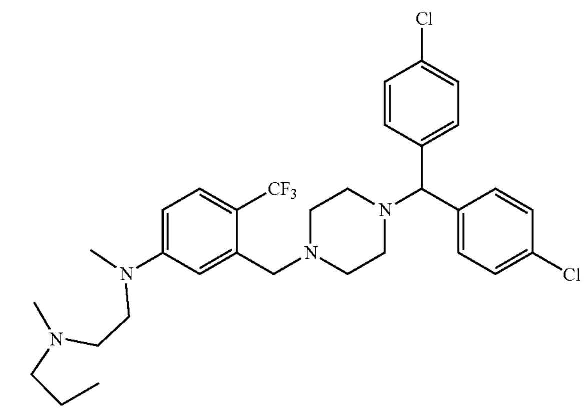 [SMILES: CCCN(C)CCN(C)c1ccc(C(F)(F)F)c(CN2CCN(C(c3ccc(Cl)cc3)c3ccc(Cl)cc3)CC2)c1] | +++ | 608 |
| 71 | $N^1$-(3-((4-(bis(4-fluorophenyl)methyl)piperazin-1-yl)methyl)-4-(trifluoromethyl)phenyl)-$N^2$-(2-(dimethylamino)ethyl)-$N^1,N^2$-dimethylethan-1,2-diamine | 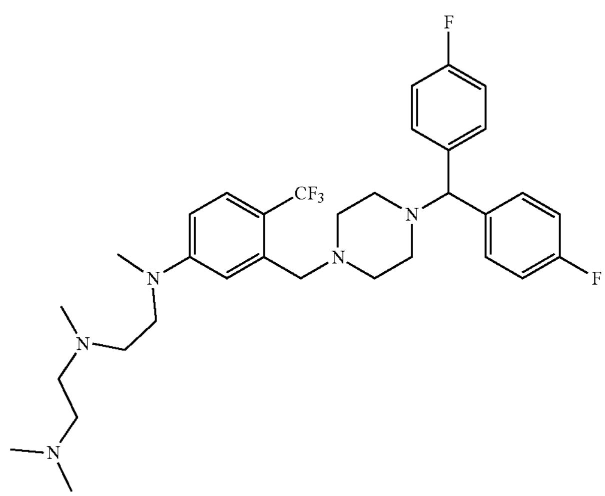 [SMILES: CN(C)CCN(C)CCN(C)c1ccc(C(F)(F)F)c(CN2CCN(C(c3ccc(F)cc3)c3ccc(F)cc3)CC2)c1] | +++ | 604 |
| 72 | $N^1$-(3-((4-(bis(4-chlorophenyl)methyl)piperidin-1-yl)methyl)-4-(trifluoromethyl)phenyl)-$N^1,N^2,N^2$-trimethylethan-1,2-diamine | 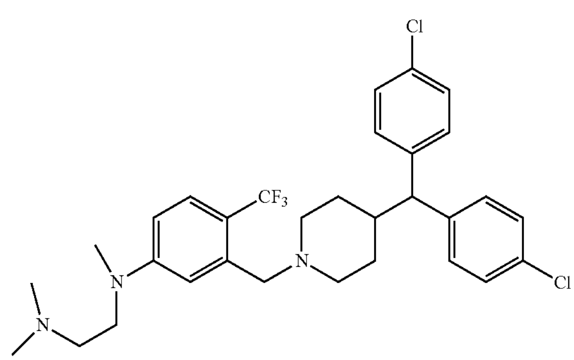 [SMILES: CN(C)CCN(C)c1ccc(C(F)(F)F)c(CN2CCC(C(c3ccc(Cl)cc3)c3ccc(Cl)cc3)CC2)c1] | +++ | 579 |

TABLE 1-continued

Activity of compounds against HCV

| Number | chemical name | structures | inhibitory activities* | molecular weight# |
|---|---|---|---|---|
| 73 | N$^1$-(3-((4-(bis(4-bromophenyl)methyl)piperidin-1-yl)methyl)-4-(trifluoromethyl)phenyl)-N$^1$,N$^2$,N$^2$-trimethylethan-1,2-diamine | 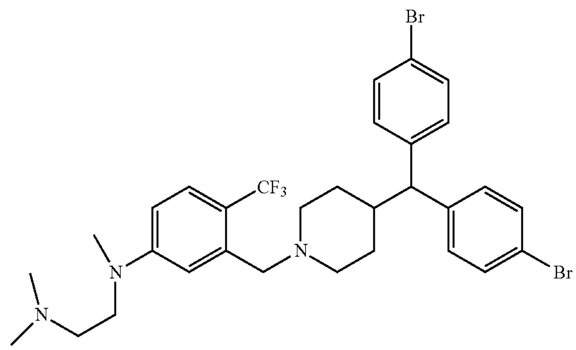 [SMILES: CN(C)CCN(C)c1ccc(C(F)(F)F)c(CN2CCC(C(c3ccc(Br)cc3)c3ccc(Br)cc3)CC2)c1] | +++ | 667 |
| 74 | 2-((4-(bis(4-chlorophenyl)methyl)piperazin-1-yl)methyl)-4-((2-(dimethylamino)ethyl)(methyl)amino)benzonitrile | 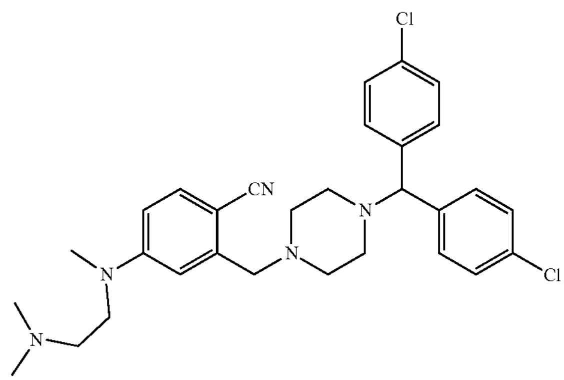 [SMILES: CN(C)CCN(C)c1ccc(C#N)c(CN2CCN(C(c3ccc(Cl)cc3)c3ccc(Cl)cc3)CC2)c1] | +++ | 537 |
| 75 | 2-((4-(bis(4-methoxyphenyl)methyl)piperazin-1-yl)methyl)-4-(4-methyl-1,4-diazepan-1-yl)benzonitrile | 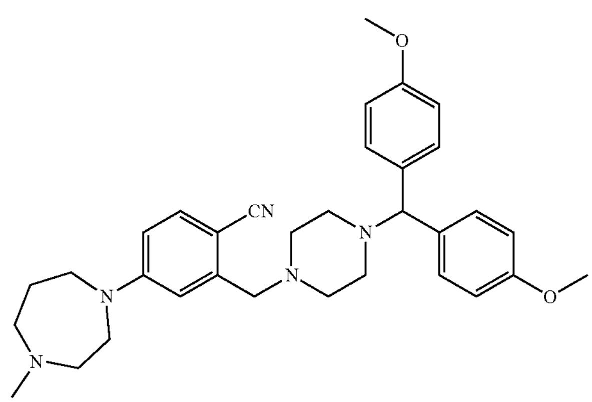 | +++ | 540 |
| 76 | 2-((4-(bis(4-fluorophenyl)methyl)piperazin-1-yl)methyl)-4-(4-methyl-1,4-diazepan-1-yl)benzonitrile | 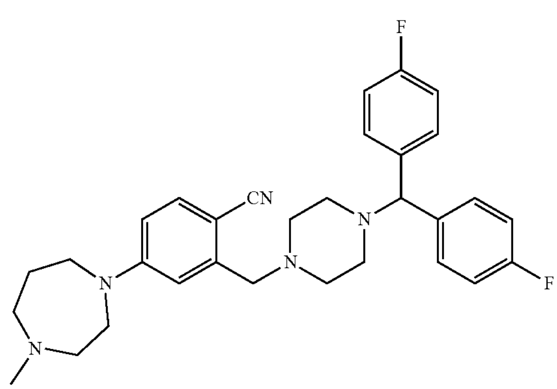 | +++ | 516 |

TABLE 1-continued

Activity of compounds against HCV

| Number | chemical name | structures | inhibitory activities* | molecular weight# |
|---|---|---|---|---|
| 77 | 2-((4-(bis(4-chlorophenyl)methyl)piperazin-1-yl)methyl)-4-(4-methyl-1,4-diazepan-1-yl)benzonitrile | 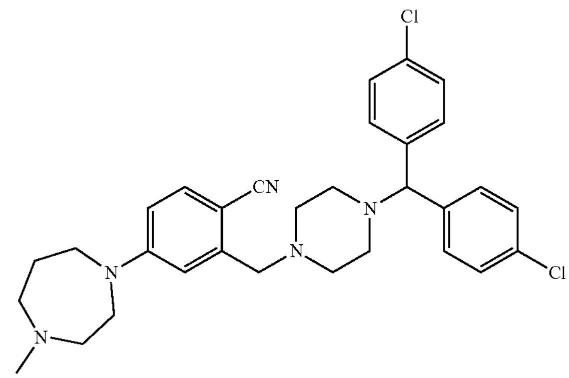 [SMILES: CN1CCCN(c2ccc(C#N)c(CN3CCN(C(c4ccc(Cl)cc4)c4ccc(Cl)cc4)CC3)c2)CC1] | +++ | 549 |
| 78 | 4-((2-(1H-imidazol-1-yl)ethyl)(methyl)amino)-2-((4-(bis(4-chlorophenyl)methyl)piperazin-1-yl)methyl)benzonitrile | 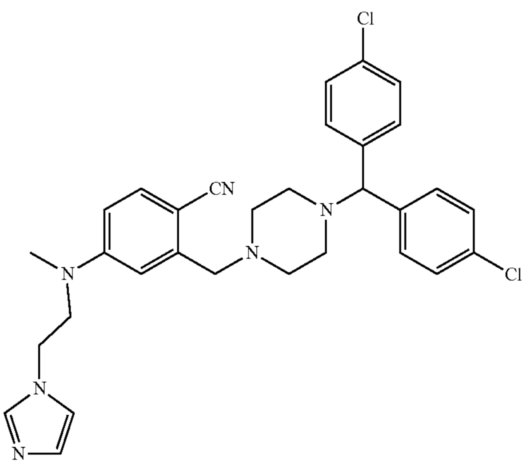 [SMILES: CN(CCn1ccnc1)c1ccc(C#N)c(CN2CCN(C(c3ccc(Cl)cc3)c3ccc(Cl)cc3)CC2)c1] | +++ | 560 |
| 79 | 2-((4-(di(pyridin-4-yl)methyl)piperazin-1-yl)methyl)-4-((2-(dimethylamino)ethyl)(methyl)amino)benzonitrile | 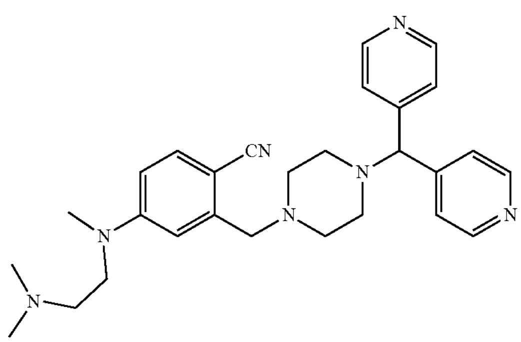 [SMILES: CN(C)CCN(C)c1ccc(C#N)c(CN2CCN(C(c3ccncc3)c3ccncc3)CC2)c1] | ++ | 470 |
| 80 | 2-((4-(bis(4-chlorophenyl)methyl)piperazin-1-yl)methyl)-4-(4-methylpiperazin-1-yl)benzonitrile | 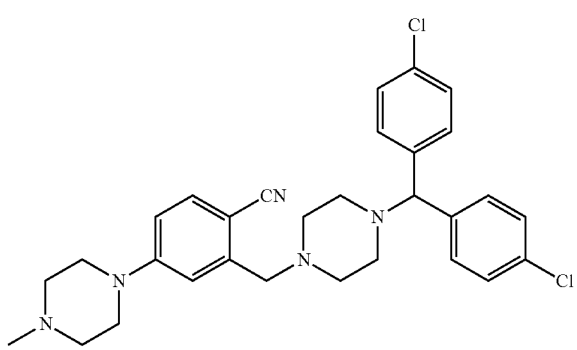 [SMILES: CN1CCN(c2ccc(C#N)c(CN3CCN(C(c4ccc(Cl)cc4)c4ccc(Cl)cc4)CC3)c2)CC1] | +++ | 535 |

TABLE 1-continued

Activity of compounds against HCV

| Number | chemical name | structures | inhibitory activities* | molecular weight# |
|---|---|---|---|---|
| 81 | 2-((4-(bis(4-isopropylphenyl)methyl)piperazin-1-yl)methyl)-4-((2-(dimethylamino)ethyl)(methyl)amino)benzonitrile | 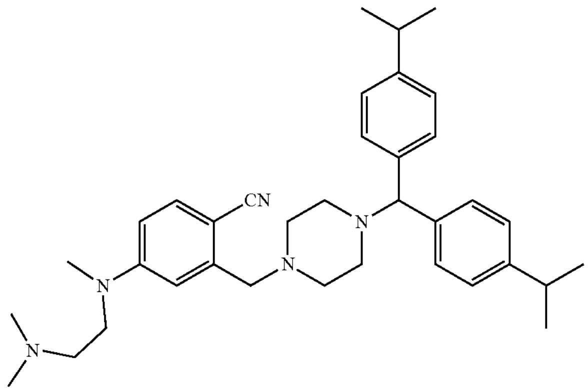 [SMILES: CC(C)c1ccc(C(c2ccc(C(C)C)cc2)N2CCN(Cc3cc(N(C)CCN(C)C)ccc3C#N)CC2)cc1] | +++ | 552 |
| 82 | 2-((4-(bis(4-tert-butylphenyl)methyl)piperazin-1-yl)methyl)-4-((2-(dimethylamino)ethyl)(methyl)amino)benzonitrile | 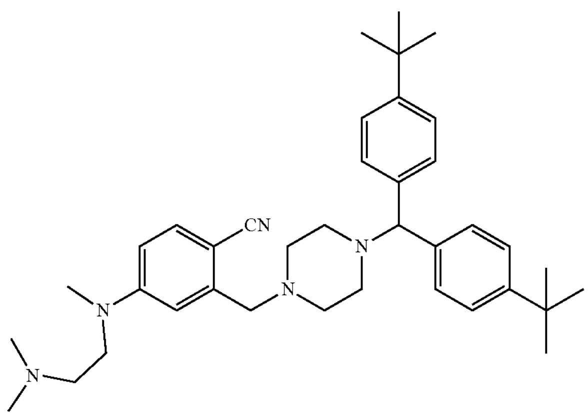 [SMILES: CN(C)CCN(C)c1ccc(C#N)c(CN2CCN(C(c3ccc(C(C)(C)C)cc3)c3ccc(C(C)(C)C)cc3)CC2)c1] | +++ | 580 |
| 83 | 2-((4-(bis(4-bromophenyl)methyl)piperazin-1-yl)methyl)-4-((2-(dimethylamino)ethyl)(methyl)amino)benzonitrile | 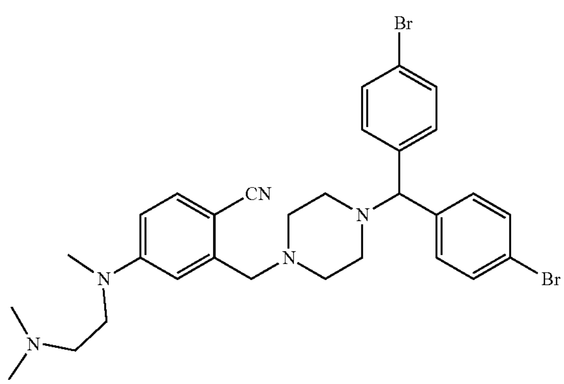 [SMILES: CN(C)CCN(C)c1ccc(C#N)c(CN2CCN(C(c3ccc(Br)cc3)c3ccc(Br)cc3)CC2)c1] | +++ | 625 |

TABLE 1-continued

Activity of compounds against HCV

| Number | chemical name | structures | inhibitory activities* | molecular weight# |
|---|---|---|---|---|
| 84 | 2-((4-(bis(4-cyclopropylphenyl)methyl)piperazin-1-yl)methyl)-4-((2-(dimethylamino)ethyl)(methyl)amino)benzonitrile | 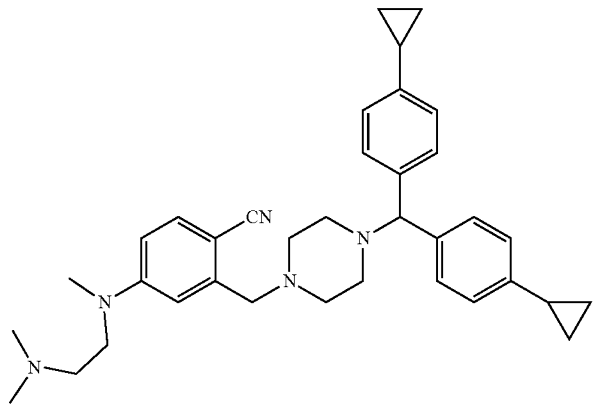 [SMILES: CN(C)CCN(C)c1ccc(C#N)c(CN2CCN(C(c3ccc(C4CC4)cc3)c3ccc(C4CC4)cc3)CC2)c1] | +++ | 548 |
| 85 | 2-((4-(bis(4-chlorophenyl)methyl)piperazin-1-yl)methyl)-4-(3-(dimethylamino)pyrrolidin-1-yl)benzonitrile | 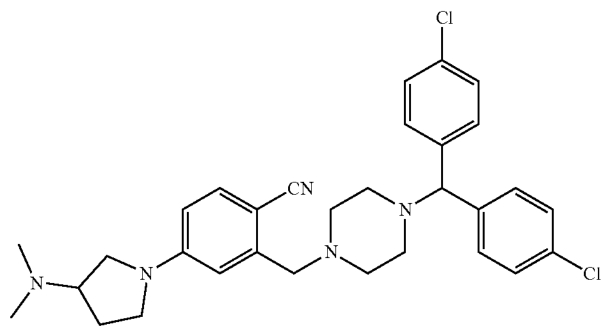 [SMILES: CN(C)C1CCN(c2ccc(C#N)c(CN3CCN(C(c4ccc(Cl)cc4)c4ccc(Cl)cc4)CC3)c2)C1] | +++ | 549 |
| 86 | 2-((4-(bis(4-chlorophenyl)methyl)piperazin-1-yl)methyl)-4-(methyl(2-(pyrrolidin-1-yl)ethyl)amino)benzonitrile | 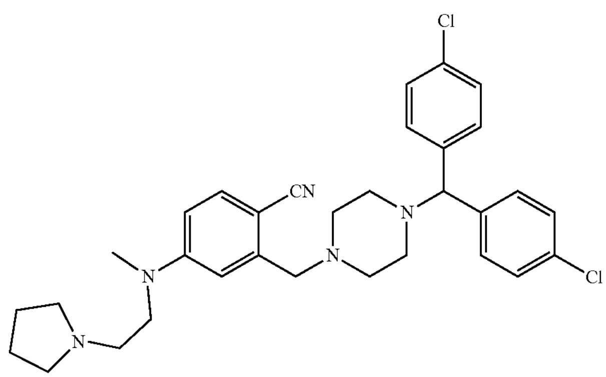 [SMILES: CN(CCN1CCCC1)c1ccc(C#N)c(CN2CCN(C(c3ccc(Cl)cc3)c3ccc(Cl)cc3)CC2)c1] | +++ | 563 |
| 87 | 4-((2-(aziridin-1-yl)ethyl)(methyl)amino)-2-((4-(bis(4-chlorophenyl)methyl)piperazin-1-yl)methyl)benzonitrile | 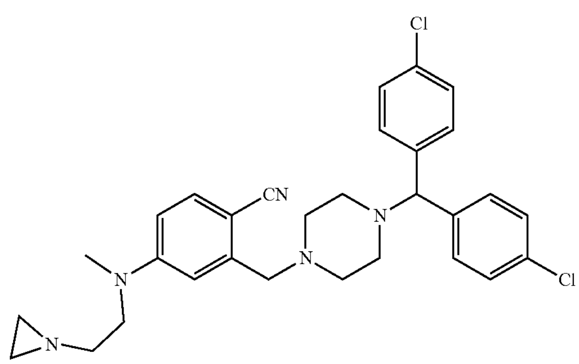 [SMILES: CN(CCN1CC1)c1ccc(C#N)c(CN2CCN(C(c3ccc(Cl)cc3)c3ccc(Cl)cc3)CC2)c1] | ++ | 535 |

TABLE 1-continued

Activity of compounds against HCV

| Number | chemical name | structures | inhibitory activities* | molecular weight# |
|---|---|---|---|---|
| 88 | 2-((4-((4-chlorophenyl)(phenyl)methyl)piperazin-1-yl)methyl)-4-(4-methyl-1,4-diazepan-1-yl)benzonitrile | 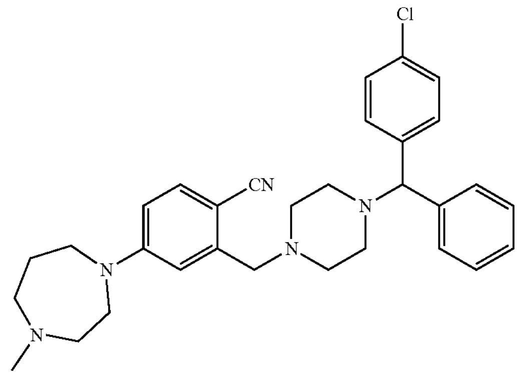 [SMILES: CN1CCCN(c2ccc(C#N)c(CN3CCN(C(c4ccccc4)c4ccc(Cl)cc4)CC3)c2)CC1] | +++ | 514 |
| 89 | 2-((4-((4-chlorophenyl)(pyridin-4-yl)methyl)piperazin-1-yl)methyl)-4-(4-methyl-1,4-diazepan-1-yl)benzonitrile | 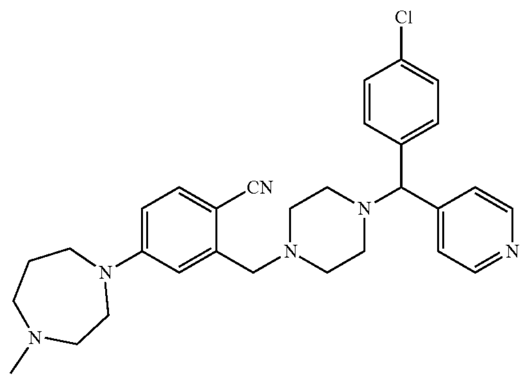 [SMILES: CN1CCCN(c2ccc(C#N)c(CN3CCN(C(c4ccncc4)c4ccc(Cl)cc4)CC3)c2)CC1] | +++ | 515 |
| 90 | 2-((4-(bis(4-chlorophenyl)methyl)piperidin-1-yl)methyl)-4-((2-(dimethylamino)ethyl)(methyl)amino)benzonitrile | 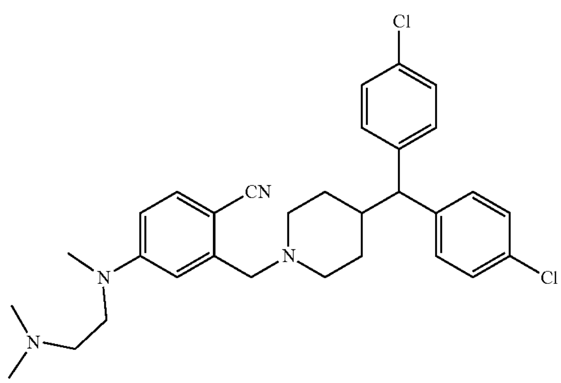 | +++ | 536 |
| 91 | 2-((4-(bis(4-fluorophenyl)methyl)piperidin-1-yl)methyl)-4-(4-methyl-1,4-diazepan-1-yl)benzonitrile | 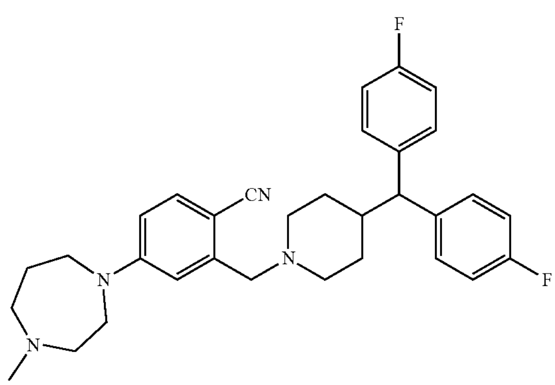 [SMILES: CN1CCCN(c2ccc(C#N)c(CN3CCC(C(c4ccc(F)cc4)c4ccc(F)cc4)CC3)c2)CC1] | +++ | 515 |

TABLE 1-continued

Activity of compounds against HCV

| Number | chemical name | structures | inhibitory activities* | molecular weight# |
|---|---|---|---|---|
| 92 | N-{3-[4-(4-chlorophenyl)piperazin-1-yl]methyl)-4-(trifluoromethyl)phenyl}-N,1-dimethylpyrrolidin-3-amine | 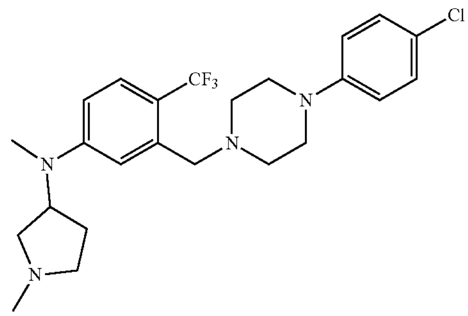 [SMILES: CN1CCC(N(C)c2ccc(C(F)(F)F)c(CN3CCN(c4ccc(Cl)cc4)CC3)c2)C1] | +++ | 467 |
| 93 | 4-[{2-[ethyl(methyl)amino]ethyl}(methyl)amino)-2-({4-[1-(pyrazin-2-yl)ethyl]piperazin-1-yl}methyl)benzonitrile | 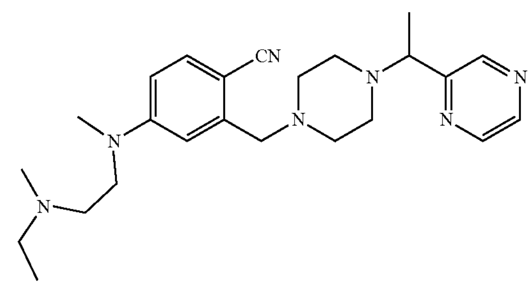 [SMILES: CCN(C)CCN(C)c1ccc(C#N)c(CN2CCN(C(C)c3cnccn3)CC2)c1] | ++ | 422 |
| 94 | N1-(3-[{4-[bis(3,4-dichlorophenyl)methyl]piperazin-1-yl}methyl]-4-(trifluoromethyl)phenyl)-N2,N2-diethyl-N1-methylethan-1,2-diamine | 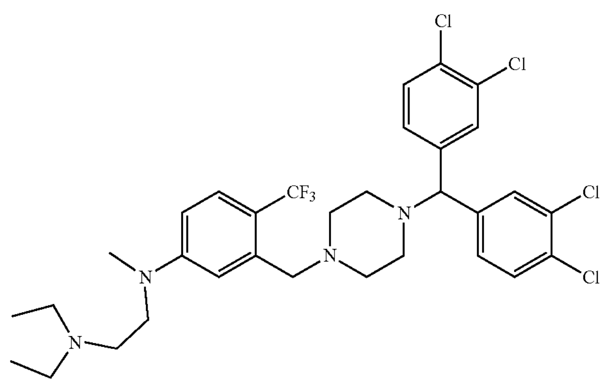 [SMILES: CCN(CC)CCN(C)c1ccc(C(F)(F)F)c(CN2CCN(C(c3ccc(Cl)c(Cl)c3)c3ccc(Cl)c(Cl)c3)CC2)c1] | +++ | 676 |
| 95 | 2-({4-[bis(4-chloro-3-methylphenyl)methyl]piperazin-1-yl}methyl)-4-{[2-(dimethylamino)ethyl](methyl)amino)benzonitrile | 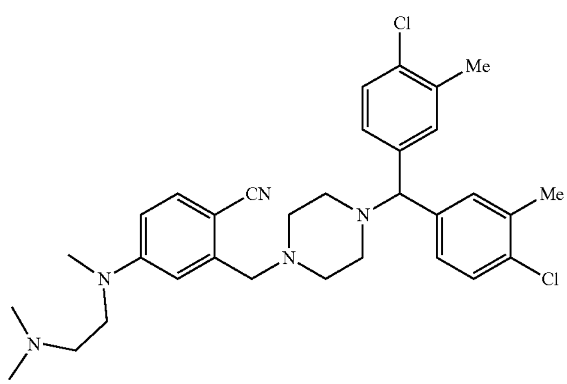 [SMILES: Cc1cc(C(c2ccc(Cl)c(C)c2)N2CCN(Cc3cc(N(C)CCN(C)C)ccc3C#N)CC2)ccc1Cl] | +++ | 565 |

TABLE 1-continued

Activity of compounds against HCV

| Number | chemical name | structures | inhibitory activities* | molecular weight# |
|---|---|---|---|---|
| 96 | 1-[3-({4-[cyclohexyl(3,4-dichlorophenyl)methyl]piperazin-1-yl}methyl)-4-(trifluoromethyl)phenyl]-4-methyl-1,4-diazepane | 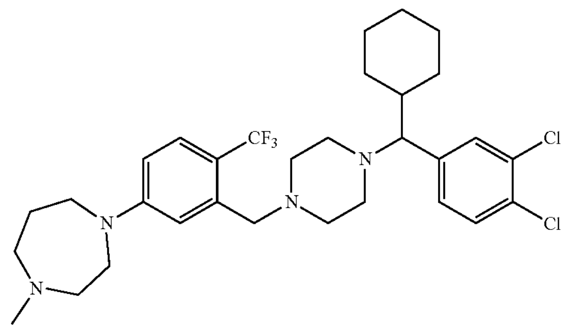 [SMILES: CN1CCCN(c2ccc(C(F)(F)F)c(CN3CCN(C(c4ccc(Cl)c(Cl)c4)C4CCCCC4)CC3)c2)CC1] | +++ | 598 |
| 97 | 2-({4-[(4-chlorophenyl)(cyclobutyl)methyl]piperazin-1-yl}methyl)-4-(4-methyl-1,4-diazepan-1-yl)benzonitrile | 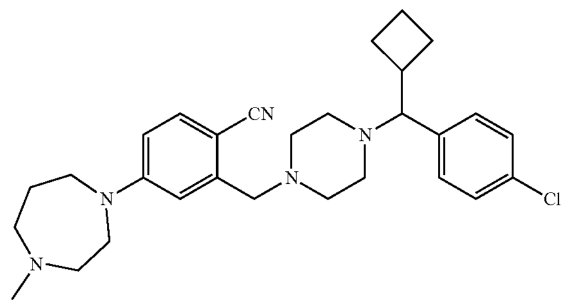 [SMILES: CN1CCCN(c2ccc(C#N)c(CN3CCN(C(c4ccc(Cl)cc4)C4CCC4)CC3)c2)CC1] | +++ | 492 |
| 98 | 2-[(4-chlorophenyl){4-[(5-(4-methylpiperazin-1-yl)-2-(trifluoromethyl)benzyl]piperazin-1-yl}methyl]pyrazine | 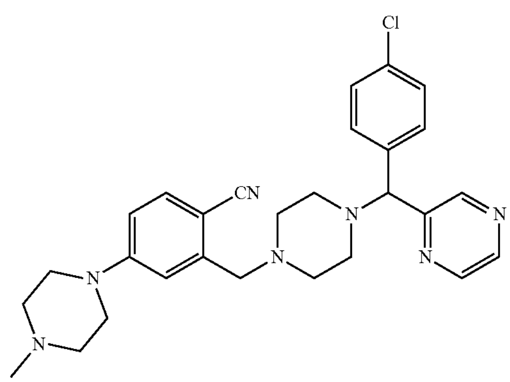 | ++ | 545 |
| 99 | 4-(4-methylpiperazin-1-yl)-2-[(4-{(pyrazin-2-yl)[(4-(trifluoromethyl)phenyl]methyl}piperazin-1-yl)methyl]benzonitrile | 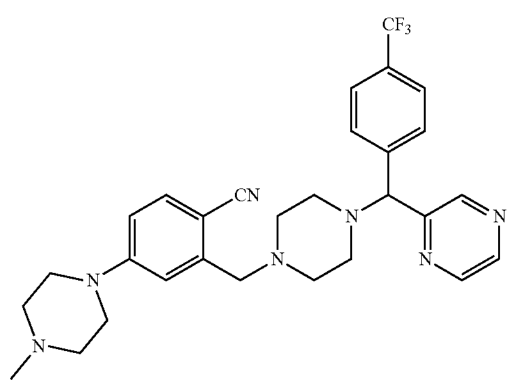 [SMILES: CN1CCN(c2ccc(C#N)c(CN3CCN(C(c4ccc(C(F)(F)F)cc4)c4cnccn4)CC3)c2)CC1] | ++ | 536 |

TABLE 1-continued

Activity of compounds against HCV

| Number | chemical name | structures | inhibitory activities* | molecular weight# |
|---|---|---|---|---|
| 100 | 1-methyl-4-[3-({4-[(4-phenoxyphenyl)(pyridin-2-yl)methyl]piperazin-1-yl}methyl)-4-(trifluoromethyl)phenyl]-1,4-diazepane | 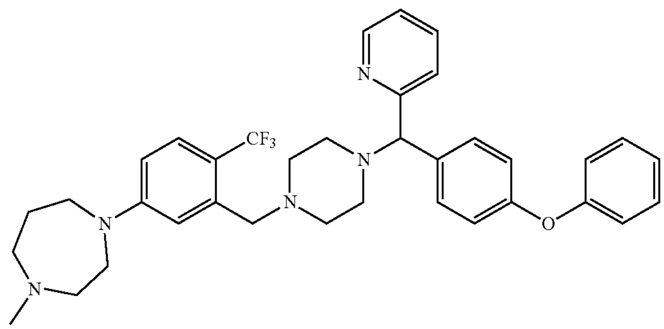 [SMILES: CN1CCCN(c2ccc(C(F)(F)F)c(CN3CCN(C(c4ccc(Oc5ccccc5)cc4)c4ccccn4)CC3)c2)CC1] | ++ | 616 |
| 101 | N-{3-([4-{bis[4-(phenylthio)phenyl]methyl}piperazin-1-yl]methyl)-4-(trifluoromethyl)phenyl}-1-ethyl-N-methylpyrrolidin-3-amine | 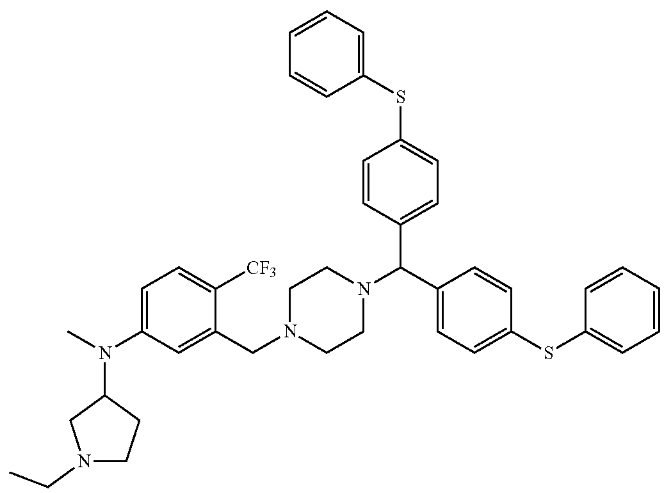 [SMILES: CCN1CCC(N(C)c2ccc(C(F)(F)F)c(CN3CCN(C(c4ccc(Sc5ccccc5)cc4)c4ccc(Sc5ccccc5)cc4)CC3)c2)C1] | +++ | 753 |
| 102 | 2-({4-(bis(4-(methylthio)phenyl]methyl}piperazin-1-yl)methyl)-4-{[2-(dimethylamino)ethyl](methyl)amino}benzonitrile | 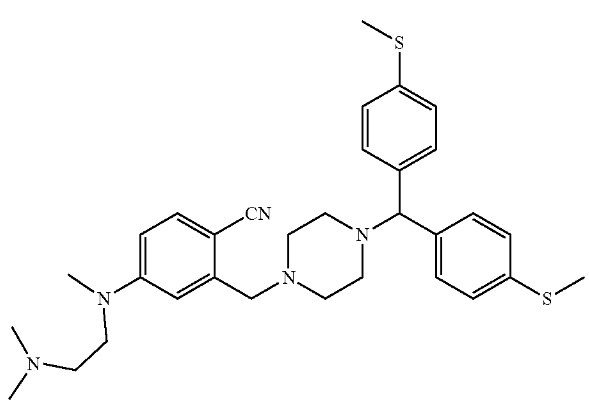 | +++ | 560 |

TABLE 1-continued

Activity of compounds against HCV

| Number | chemical name | structures | inhibitory activities* | molecular weight# |
|---|---|---|---|---|
| 103 | 3-([4-{bis[4-(trifluoromethyl)phenyl]methyl}piperazin-1-yl]methyl)-N-methyl-N-[2-(pyrrolidin-1-yl)ethyl]-4-(trifluoromethyl)aniline | 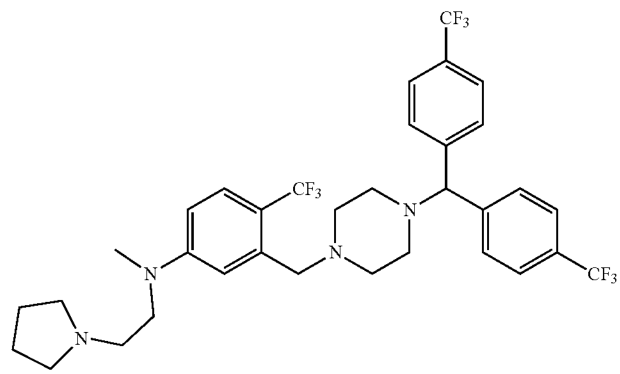 [SMILES: CN(CCN1CCCC1)c1ccc(C(F)(F)F)c(CN2CCN(C(c3ccc(C(F)(F)F)cc3)c3ccc(C(F)(F)F)cc3)CC2)c1] | +++ | 673 |
| 104 | 2-({4-[(4-cyanophenyl)(cyclopentyl)methyl]piperazin-1-yl}methyl)-4-{[2-(dimethylamino)ethyl](methyl)amino}benzonitrile | 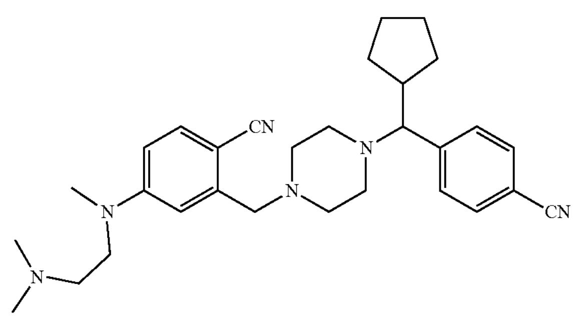 [SMILES: CN(C)CCN(C)c1ccc(C#N)c(CN2CCN(C(c3ccc(C#N)cc3)C3CCCC3)CC2)c1] | +++ | 485 |
| 105 | 4-{1-(4-[5-{[2-(dimethylamino)ethyl](methyl)amino}-2-(trifluoromethyl)benzyl]piperazin-1-yl)ethyl}benzonitrile | 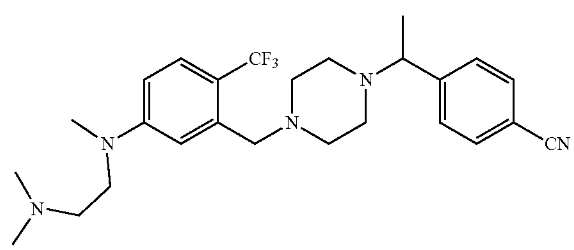 [SMILES: CC(c1ccc(C#N)cc1)N1CCN(Cc2cc(N(C)CCN(C)C)ccc2C(F)(F)F)CC1] | +++ | 474 |
| 106 | 4-([3-(1H-imidazol-1-yl)propyl]amino)-2-({4-[bis(4-chlorophenyl)methyl]piperazin-1-yl}methyl)benzonitrile | 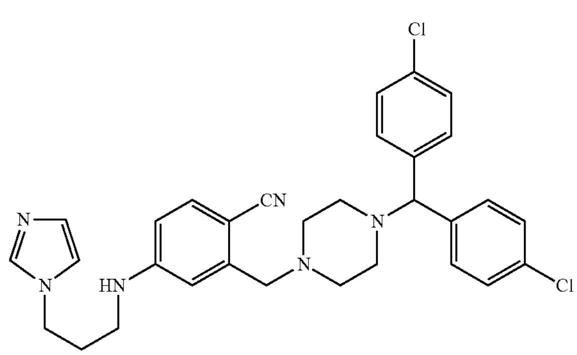 [SMILES: N#Cc1ccc(NCCCn2ccnc2)cc1CN1CCN(C(c2ccc(Cl)cc2)c2ccc(Cl)cc2)CC1] | +++ | 560 |

TABLE 1-continued

Activity of compounds against HCV

| Number | chemical name | structures | inhibitory activities* | molecular weight# |
|---|---|---|---|---|
| 107 | $N^1$-(3-((4-(3,4-dichlorophenyl)piperazin-1-yl)methyl)-4-(trifluoromethyl)phenyl)-$N^1,N^2,N^2$-trimethylethan-1,2-diamine | 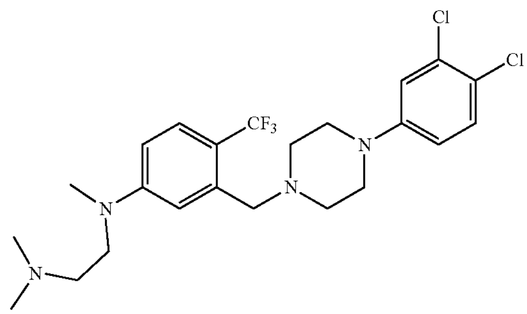 | +++ | 489 |
| 108 | $N^1$-(3-((4-(4-chloro-3-methylphenyl)piperazin-1-yl)methyl)-4-(trifluoromethyl)phenyl)-$N^1,N^2,N^2$-trimethylethan-1,2-diamine | 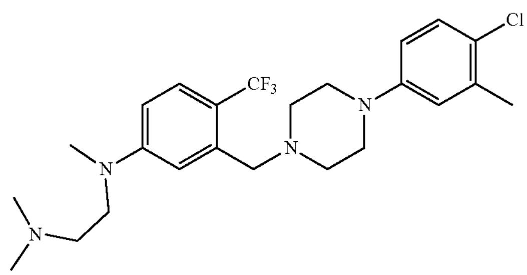 | +++ | 469 |
| 109 | 1-(3-((4-(3,4-dichlorophenyl)piperazin-1-yl)methyl)-4-(trifluoromethyl)phenyl)-4-methyl-1,4-diazepane | 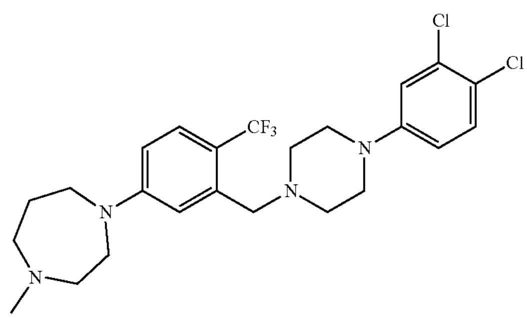 [SMILES: CN1CCCN(c2ccc(C(F)(F)F)c(CN3CCN(c4ccc(Cl)c(Cl)c4)CC3)c2)CC1] | +++ | 501 |

*Inhibitory levels of the compounds against HCV replication at an administered concentration of 1 μM, + indicates inhibition rates in the range of 25%-50%, ++ indicates inhibition rates in the range of 50%-75% and +++ indicates inhibition rates above 75%.
The effective digits of molecular weights of all compounds in the table are retained to three digits and rounded off.

The invention claimed is:

1. A compound having the structure as shown in the formula I or a pharmaceutically acceptable salt thereof:

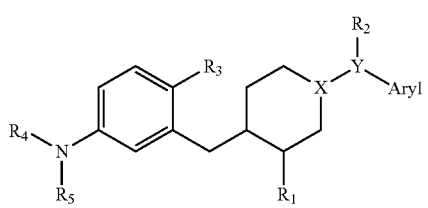

I wherein $R_1$ is alkyl containing 1 to 4 carbons or H;
$R_2$ is H, alkyl, cycloalkyl, aryl, heteroaryl, or, aryl or heteroaryl substituted with 1, 2 or 3 substituents, wherein, the substituent is selected from the group consisting of alkyl, cycloalkyl, alkoxy, phenoxy, alkylthio, phenylthio, halogen, cyano, and haloalkyl; when being alkyl or cycloalkyl, $R_2$ is alkyl containing 1 to 6 carbon atoms, or cycloalkyl containing 3 to 6 carbon atoms, and the alkyl and cycloalkyl are optionally substituted with halogen;
$R_3$ is cyano or trifluoromethyl;
X is N or CH;
Y is CH;
Aryl is a benzene or aza-aromatic ring, or a benzene or aza-aromatic ring containing 1-3 substituents selected from the group consisting of alkyl, cycloalkyl, alkyloxy, phenoxy or substituted phenoxy, alkylthio, phenylthio or substituted phenylthio, haloalkyl, cyano, and halogen;
$R_4$ is substituted alkyl or substituted heterocycloalkyl, and when $R_4$ is substituted alkyl, the substituent is selected from the group consisting of alkylamino, dialkylamino, and saturated or unsaturated heterocyclyl containing one nitrogen or two nitrogens; when $R_4$ is substituted heterocycloalkyl, the heterocycloalkyl contains at least one nitrogen atom, and the substituent is selected from the group consisting of alkyl, alkylamino and dialkylamino;

$R_5$ is hydrogen or alkyl containing 1-4 carbons;

alternatively, $R_4$, $R_5$, and the nitrogen atom to which they are attached jointly form a cyclic structure containing 1 or 2 nitrogen atoms or cyclic structure substituted with a substituent selected from the group consisting of alkyl containing 1 to 6 carbons, alkylamino, dialkylamino, cycloalkyl, and heterocyclic groups.

2. The compound as claimed in claim 1 or a pharmaceutically acceptable salt thereof having the structure shown in the formula II:

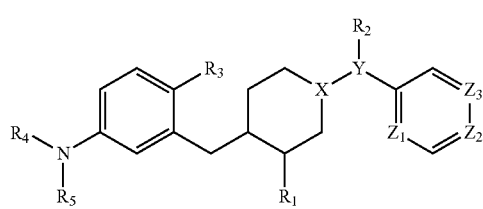

wherein $R_1$ is alkyl containing 1 to 4 carbons or H;

$R_2$ is H, alkyl, cycloalkyl, aryl, heteroaryl, or, aryl or heteroaryl substituted with 1, 2 or 3 substituents, wherein, the substituent is selected from the group consisting of alkyl, cycloalkyl, alkoxy, phenoxy, alkylthio, phenylthio, halogen, cyano, and haloalkyl; when being alkyl or cycloalkyl, $R_2$ is alkyl containing 1 to 6 carbon atoms, or cycloalkyl containing 3 to 6 carbon atoms, or optionally substituted with halogen;

$R_3$ is cyano or trifluoromethyl;

X is N or CH;

Y is CH;

$Z_1$, $Z_2$, $Z_3$ are the same or different, $Z_1$, $Z_2$, $Z_3$ are each $C(R_6)$ or N, respectively, $R_6$ is H, alkyl, cycloalkyl, alkyloxy, phenoxy or substituted phenoxy, alkylthio, phenylthio or substituted phenylthio, haloalkyl, cyano, or halogen;

$R_4$ is

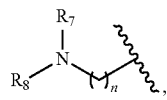

wherein, n=1-3, $R_7$, $R_8$ are each H, alkyl, or substituted alkyl, respectively, or $R_7$ and $R_8$, together with the nitrogen atom to which they are bonded, form a cyclic group or a substituted cyclic group substituted with 1, 2 or 3 substituents selected from the group consisting of alkyl, alkylamino, dialkylamino, and heterocyclyl, the cyclic group is a three-, four-, five-, six-, or seven-membered saturated or unsaturated cyclic group containing 1 or 2 nitrogen atoms;

or $R_4$ is

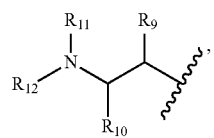

wherein $R_{12}$ is alkyl containing 1-4 carbon atoms;

$R_{11}$, the nitrogen to which $R_{11}$ is bound, the carbon to which $R_{10}$ is bound, the carbon to which $R_9$ is bound, and $R_9$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, alkylamino, and dialkylamino, and akyl in the alkylamino and dialkylamino contains 1 to 4 carbon atoms, $R_{10}$ is H;

or $R_{11}$ with the nitrogen to which it is bound, the carbon to which $R_{10}$ is bound, and $R_{10}$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, C1-C4 alkylamino, and di-C1-C4 alkylamino, $R_9$ is H;

alternatively, $R_4$ is alkyl which contains 1-4 carbons and is substituted by amino, alkylamino, dialkylamino, or four-, five-, or six membered saturated heterocycles containing one or two nitrogens;

alternatively, $R_5$, $R_4$ and the nitrogen atom to which they are bonded together form a saturated heterocycle or a saturated heterocycle substituted by a substituent, and the heterocycle is a five-, six- or seven-membered heterocycle containing one or two nitrogen atoms, the substituents are selected from the group consisting of alkyl containing 1 to 6 carbon atoms, C1-C4 alkylamino groups, di-C1-C4 alkylamino groups, cycloalkyl groups containing 3 to 5 carbon atoms or saturated heterocyclic groups containing one nitrogen.

3. The compound or the pharmaceutically acceptable salt thereof as claimed in claim 1, when $R_4$ is

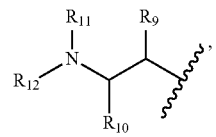

$R_4$ is

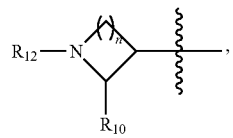

n=2 or 3, $R_{10}$ is H; or $R_4$ is

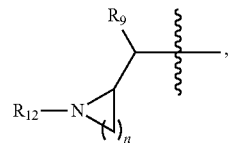

n=2, 3 or 4, and $R_9$ is H.

4. The compound or the pharmaceutically acceptable salt thereof as claimed in claim 1, wherein $R_5$, $R_4$ and the nitrogen atom to which they are bonded together form a saturated heterocycle or a saturated heterocycle substituted by a substituent, and the heterocycle is a five-, six- or seven-membered heterocycle containing one or two heteroatoms, the five-membered heterocycle is selected from the group consisting of pyrrolidinyl, pyrrolyl, imidazolyl, imidazolidinyl, and oxazolyl, the six-membered heterocycle is selected from the group consisting of morpholine, piperazine, and piperidine, and the seven-membered heterocycle is selected from 1,4-diazepane; the substituents are selected from the group consisting of alkyl containing 1 to 4 carbon atoms, di-C1-C4 alkylamino groups, cycloalkyl groups containing 3 to 5 carbon atoms, and heterocyclic groups containing 3 to 5 carbon atoms and one nitrogen.

5. The compound or the pharmaceutically acceptable salt thereof as claimed in claim 4, wherein $R_5$, $R_4$ together with the nitrogen atom to which they are bonded form

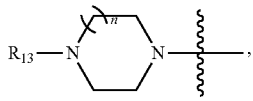

wherein n=1 or 2, $R_{13}$ is alkyl containing 1-4 carbons or cycloalkyl containing 3 to 5 carbons, and the alkyl containing 1-4 carbon is methyl or ethyl;

or $R_5$, $R_4$ together with the nitrogen atom to which they are bonded form

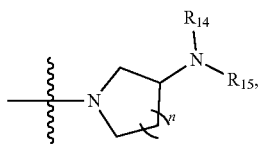

wherein n=1 or 2, $R_{14}$ and $R_{15}$ are alkyl groups containing 1 to 4 carbons;

or $R_5$, $R_4$ together with the nitrogen atom to which they are bonded form

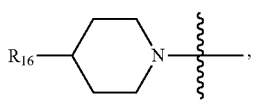

wherein $R_{16}$ is a diC1-C4 alkylamino group, pyrrolidinyl;

or $R_5$, $R_4$ together with the nitrogen atom to which they are bonded form

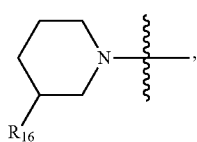

$R_{16}$ is a diC1-C4 alkylamino.

6. The compound as claimed in claim 1 having the structure shown in the formula III or a pharmaceutically acceptable salt thereof:

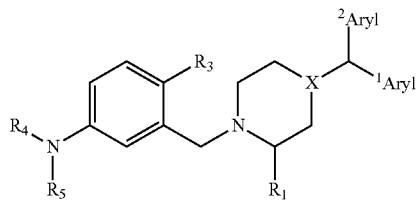

$^1$Aryl is the same as or different from $^2$Aryl, $^1$Aryl and $^2$Aryl are each a benzene ring or aza aromatic ring, or a substituted benzene ring or aza aromatic ring, the aza aromatic ring is a heteroaromatic ring containing 1 to 2 nitrogen atoms, rings, the substitution is that 1 to 2 substituents are at any position on the ring, and the substituents are selected from the group consisting of hydrogen, alkyl, cycloalkyl, alkoxy, phenoxy or substituted phenoxy, alkylthio, phenylthio, phenylthio or substituted phenylthio, haloalkyl, cyano and halogen;

$R_1$ is alkyl containing 1 to 4 carbons or H;
$R_3$ is cyano or trifluoromethyl;
X is N or CH;
$R_4$ is substituted alkyl or substituted heterocycloalkyl, and when $R_4$ is substituted alkyl, the substituent is selected from the group consisting of alkylamino, dialkylamino, and saturated or unsaturated heterocyclyl containing one nitrogen or two nitrogens; when $R_4$ is a substituted heterocycloalkyl, the heterocycloalkyl contains at least one nitrogen atom, and the substituent is selected from the group consisting of alkyl, alkylamino and dialkylamino;

$R_5$ is hydrogen or an alkyl containing 1-4 carbons;
or, $R_5$, $R_4$ and the nitrogen atom to which they are bonded together form a saturated heterocycle or a saturated heterocycle substituted by a substituent, and the heterocycle is a five-, six- or seven-membered heterocycle containing one or two nitrogen atoms, the substituents are selected from the group consisting of alkyl containing 1 to 6 carbon atoms, alkylamino, di-C1-C4 alkylamino, cycloalkyl containing 3 to 5 carbon atoms or saturated heterocyclic groups containing one nitrogen.

7. The compound or the pharmaceutically acceptable salt thereof as claimed in claim 6, wherein $R_4$ is

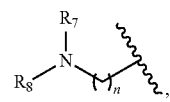

wherein, n=1-3, $R_7$ and $R_8$ are H or alkyl or substituted alkyl, or $R_7$ and $R_8$ together with the nitrogen atom to which they are bonded form a cyclic group or substituted cyclic group, the substituent is selected from the group consisting of alkyl, alkylamino, dialkylamino and heterocyclic group, the cyclic group is three-, four-, five-, six- or seven-membered saturated or unsaturated cyclic group containing 1 or 2 nitrogen atoms, the three-membered cyclic group is selected from aziridinyl, and the four-membered cyclic group is selected from azetidinyl, the five-membered cyclic group is selected from the group consisting of pyrrolyl, pyrrolidinyl, imidazolyl and oxazolyl, and the six-membered cyclic group is selected from the group consisting of morpholinyl, piperazinyl, piperidinyl, pyridinyl, and pyrimidinyl, the seven-membered cyclic group is 1,4-diazepanyl;

or $R_4$ is

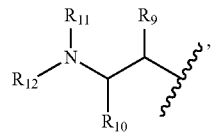

wherein $R_{12}$ is alkyl containing 1-4 carbon atoms;

$R_{11}$ the nitrogen to which $R_{11}$ is bound, the carbon to which $R_{10}$ is bound, the carbon to which $R_9$ is bound, and $R_9$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, alkylamino, and dialkylamino, $R_{10}$ is H; or $R_{11}$, the nitrogen to which $R_{11}$ is bound, the carbon to which $R_{10}$ is bound, and $R_{10}$ together form a saturated five-, six-, or seven-membered heterocyclic ring or a saturated five-, six-, or seven-membered heterocyclic ring substituted by 1 or 2 substituents selected from the group consisting of alkyl containing 1 to 4 carbon atoms, alkylamino, and di-C1-C4 alkylamino, $R_9$ is H;

or, $R_4$ is a substituted alkyl, the substituent is selected from the group consisting of amino, alkylamino, dialkylamino, and four-, five-, or six-membered saturated heterocycles containing one or two nitrogens.

8. The compound or the pharmaceutically acceptable salt thereof as claimed in claim 7, when $R_4$ is

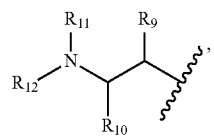

$R_4$ is

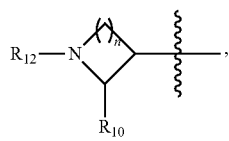

n=2 or 3, $R_{10}$ is H; or $R_4$ is

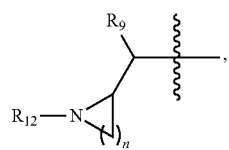

n=2, 3 or 4, and $R_9$ is H.

9. The compound or the pharmaceutically acceptable salt thereof as claimed in claim 6, wherein $R_5$, $R_4$ and the nitrogen atom to which they are bonded together form a saturated heterocycle or a saturated heterocycle substituted by a substituent, and the heterocycle is a five-, six- or seven-membered heterocycle containing one or two heteroatoms, the five-membered heterocycle is selected from the group consisting of pyrrolidinyl, pyrrolyl, imidazolyl, imidazolidinyl, and oxazolyl, the six-membered heterocycle is selected from the group consisting of morpholine, piperazine, and piperidine, and the seven-membered heterocycle is selected from 1,4-diazepane; the substituents are selected from the group consisting of alkyl containing 1 to 4 carbon atoms, di-C1-C4 alkylamino, cycloalkyl containing 3 to 5 carbon atoms, and heterocyclic groups containing 3 to 5 carbon atoms and one nitrogens.

10. The compound or the pharmaceutically acceptable salt thereof as claimed in claim 9, wherein $R_5$, $R_4$ together with the nitrogen atom to which they are bonded form

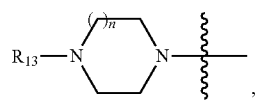

wherein n=1 or 2, $R_{13}$ is alkyl containing 1-4 carbons or cycloalkyl containing 3 to 5 carbons;

or $R_5$, $R_4$ together with the nitrogen atom to which they are bonded form

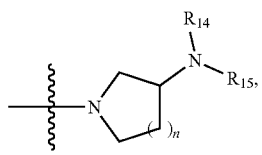

wherein n=1 or 2, $R_{14}$ and $R_{15}$ are alkyl groups containing 1 to 4 carbons;

or $R_5$, $R_4$ together with the nitrogen atom to which they are bonded form

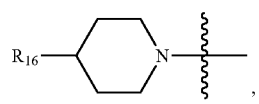

wherein $R_{16}$ is a diC1-C4 alkylamino group or a saturated five-membered heterocyclic ring containing one nitrogen;

or, $R_5$, $R_4$ together with the nitrogen atom to which they are bonded form

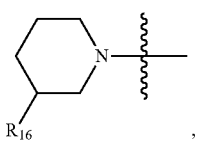

$R_{16}$ is a diC1-C4 alkylamino.

11. The compound or the pharmaceutically acceptable salt thereof as claimed in claim 1, which is:

1-(3-((4-(1-(4-bromophenyl)ethyl)piperazin-1-yl)methyl)-4-(trifluoromethyl)phenyl)-4-methyl-1,4-diazepane 1-(3-((4-(4-chlorobenzyl)piperazin-1-yl)methyl)-4-(trifluoromethyl)phenyl)-4-methyl-1,4-diazepane 1-(3-((4-(1-(3-chloro-4-fluorophenyl)ethyl)piperazin-1-yl)methyl)-4-(trifluoromethyl)phenyl)-4-methyl-1,4-diazepane 1-(3-((4-(4-chloro-3-methylbenzyl)piperazin-1-yl)methyl)-4-(trifluoromethyl)phenyl)-4-methyl-1,4-diazepane 1-(3-((4-(1-(4-methoxyphenyl)butyl)piperazin-1-yl)methyl)-4-(trifluoromethyl)phenyl)-4-methyl-1,4-diazepane 1-(3,4-dichlorobenzyl)-4-(5-(4-methylpiperazin-1-yl)-2-(trifluoromethyl)benzyl)piperazine 1-(3-((4-(4-chlorobenzyl)piperidin-1-yl)methyl)-4-(trifluoromethyl)phenyl)-4-methyl-1,4-diazepane N1-(3-((4-(1-(4-bromophenyl)propyl)piperazin-1-yl)methyl)-4-(trifluoromethyl)phenyl)-$N^1,N^2,N^2$-trimethylethan-1,2-diamine N1-(3-((4-(1-(4-chlorophenyl)ethyl)piperazin-1-yl)methyl)-4-(trifluoromethyl)phenyl)-$N^1,N^2,N^2$-trimethylethan-1,2-diamine $N^1,N^1,N^2$-trimethyl-$N^2$-(3-((4-(4-methylbenzyl)piperazin-1-yl)methyl)-4-(trifluoromethyl)phenyl)ethan-1,2-diamine 2-((4-(4-chloro-3-methylbenzyl)piperazin-1-yl)methyl)-4-(4-ethylpiperazin-1-yl)benzonitrile 2-((4-(4-chlorobenzyl)piperazin-1-yl)methyl)-4-(4-cyclopropylpiperazin-1-yl)benzonitrile 2-((4-(1-(4-chlorophenyl)ethyl)piperazin-1-yl)methyl)-4-((2-(ethyl(methyl)amino)ethyl)(methyl)amino)benzonitrile 4-(3-(dimethylamino)piperidin-1-yl)-2-((4-(1-phenylethyl)piperazin-1-yl)methyl)benzonitrile 4-((2-(dimethylamino)ethyl)(methyl)amino)-2-((4-(1-(4-(trifluoromethyl)phenyl)ethyl)piperazin-1-yl)methyl)benzonitrile 2-((4-(1-(4-chlorophenyl)-2-methylpropyl)piperazin-1-yl)methyl)-4-(methyl(2-(pyrrolidin-1-yl)ethyl)amino)benzonitrile 2-((4-(3-chloro-4-fluorobenzyl)piperazin-1-yl)methyl)-4-((2-(diethylamino)ethyl)(methyl)amino)benzonitrile 4-((3-(1H-pyrrol-1-yl)propyl)amino)-2-((4-(3,4-dichlorobenzyl)piperazin-1-yl)methyl)benzonitrile 1-(3-((4-(bis(4-methylphenyl)methyl)piperazin-1-yl)methyl)-4-(trifluoromethyl) phenyl)-4methyl-1,4-diazepane 1-(3-((4-(bis(4-methylphenyl)methyl)piperazin-1-yl)methyl)-4-(trifluoromethyl) phenyl)-4-methyl-1,4-diazepane 1-(3-((4-(bis(4-chlorophenyl)methyl)piperazin-1-yl)methyl)-4-(trifluoromethyl)phenyl)-4-methyl-1,4-diazepane 1-(3-((4-(bis(4-bromophenyl)methyl)piperazin-1-yl)methyl)-4-(trifluoromethyl)phenyl)-4-methyl-1,4-diazepane 1-(3-((4-(bis(4-isopropylphenyl)methyl)piperazin-1-yl)methyl)-4-(trifluoromethyl)phenyl)-4-methyl-1,4-diazepane $N^1$-(3-((4-(bis(4-cyclopropylphenyl)methyl)piperazin-1-yl)methyl)-4-(trifluoromethyl)phenyl)-$N^1,N^2,N^2$-trimethylethan-1,2-diamine N-(2-(azetidin-1-yl)ethyl)-3-((4-(bis(4-chlorophenyl)methyl)piperazin-1-yl)methyl)-N-methyl-4-(trifluoromethyl)aniline 1-(3-((4-((4-fluorophenyl)(phenyl)methyl)piperazin-1-yl)methyl)-4-(trifluoromethyl)phenyl)-4-methyl-1,4-diazepane $N^1$-(3-((4-(bis(4-chlorophenyl)methyl)piperazin-1-yl)methyl)-4-(trifluoromethyl)phenyl)-$N^1,N^2,N^2$-trimethylethan-1,2-diamine $N^1$-(3-((4-(bis(4-(trifluoromethyl)phenyl)methyl)piperazin-1-yl)methyl)-4-(trifluoromethyl)phenyl)-$N^1,N^2,N^2$-trimethylethan-1,2-diamine $N^1$-(3-((4-((4-chlorophenyl)(phenyl)methyl)piperazin-1-yl)methyl)-4-(trifluoromethyl)phenyl)-$N^1,N^2,N^2$-trimethylethan-1,2-diamine 1-(bis(4-chlorophenyl)methyl)-4-(5-(4-methylpiperazin-1-yl)-2-(trifluoromethyl)benzyl)piperazine 1-(3-((4-((4-chlorophenyl)(pyridin-2-yl)methyl)piperazin-1-yl)methyl)-4-(trifluoromethyl)phenyl)-4-methyl-1,4-diazepane 1-methyl-4-(3-((4-(phenyl(pyridin-2-yl)methyl)piperazin-1-yl)methyl)-4-(trifluoromethyl)phenyl)-1,4-diazepane $N^1$-(3-((4-(bis(4-methoxyphenyl)methyl)piperazin-1-yl)methyl)-4-(trifluoromethyl)phenyl)-$N^1,N^2,N^2$-trimethylethan-1,2-diamine $N^1$-(3-((4-(bis(4-chlorophenyl)methyl)piperazin-1-yl)methyl)-4-(trifluoromethyl)phenyl)-$N^2,N^2$-dimethyl-$N^1$-propylethan-1,2-diamine 1-(3-((4-(bis(4-fluorophenyl)methyl)-2-methylpiperazin-1-yl)methyl)-4-(trifluoromethyl)phenyl)-4-methyl-1,4-diazepane 1-(3-((4-(bis(4-chlorophenyl)methyl)-2-methylpiperazin-1-yl)methyl)-4-(trifluoromethyl)phenyl)-4-methyl-1,4-diazepane 3-((4-(bis(4-chlorophenyl)methyl)piperazin-1-yl)methyl)-N-methyl-N-((1-methylpyrrolidin-2-yl)methyl)-4-(trifluoromethyl)aniline 3-((4-(bis(4-chlorophenyl)methyl)piperazin-1-yl)methyl)-N-methyl-N-(2-(pyrrolidin-1-yl)ethyl)-4-(trifluoromethyl)aniline N-(2-(aziridin-1-yl)ethyl)-3-((4-(bis(4-chlorophenyl)methyl)piperazin-1-yl)methyl)-N-methyl-4-(trifluoromethyl)aniline 1-(3-((4-(di(pyridin-2-yl)methyl)piperazin-1-yl)methyl)-4-(trifluoromethyl)phenyl)-4-ethyl-1,4-diazepane $N^1$-(3-((4-(bis(4-fluorophenyl)methyl)piperazin-1-yl)methyl)-4-(trifluoromethyl)phenyl)-$N^1,N^2,N^2$-trimethylethan-1,2-diamine 1-(3-((4-(bis(4-chlorophenyl)methyl)piperazin-1-yl)methyl)-4-(trifluoromethyl)phenyl)-N, N-dimethylpiperidin-3-amine 1-(bis(4-bromophenyl)methyl)-4-(5-(4-methylpiperazin-1-yl)-2-(trifluoromethyl)benzyl)piperazine 1-(3-((4-(bis(4-fluorophenyl)methyl)piperazin-1-yl)methyl)-4-(trifluoromethyl)phenyl)-N, N-dimethylpiperidin-4-amine $N^1$-(3-((4-(bis(4-chlorophenyl)methyl)piperazin-1-yl)methyl)-4-(trifluoromethyl)phenyl)-$N^1,N^2$-dimethyl-$N^2$-propylethan-1,2-diamine $N^1$-(3-((4-(bis(4-fluorophenyl)methyl)piperazin-1-yl)methyl)-4-(trifluoromethyl)phenyl)-$N^2$-(2-(dimethylamino)ethyl)-$N^1,N^2$-dimethylethan-1,2-diamine $N^1$-(3-((4-(bis(4-chlorophenyl)methyl)piperidin-1-yl)methyl)-4-(trifluoromethyl)phenyl)-$N^1,N^2,N^2$-trimethylethan-1,2-diamine $N^1$-(3-((4-(bis(4-bromophenyl)methyl)piperidin-1-yl)methyl)-4-(trifluoromethyl)phenyl)-$N^1,N^2,N^2$-trimethylethan-1,2-diamine 2-((4-(bis(4-chlorophenyl)methyl)piperazin-1-yl)methyl)-4-((2-(dimethylamino)ethyl)(methyl)amino)benzonitrile 2-((4-(bis(4-methoxyphenyl)methyl)piperazin-1-yl)
methyl)-4-(4-methyl-1,4-diazepan-1-yl)benzonitrile
2-((4-(bis(4-fluorophenyl)methyl)piperazin-1-yl)
methyl)-4-(4-methyl-1,4-diazepan-1-yl)benzonitrile
2-((4-(bis(4-chlorophenyl)methyl)piperazin-1-yl)
methyl)-4-(4-methyl-1,4-diazepan-1-yl)benzonitrile
4-((2-(1H-imidazol-1-yl)ethyl)(methyl)amino)-2-((4-(bis
(4-chlorophenyl)methyl)piperazin-1-yl)methyl)benzo-
nitrile
2-((4-(di(pyridin-4-yl)methyl)piperazin-1-yl)methyl)-4-
((2-(dimethylamino)ethyl)(methyl)amino)benzonitrile
2-((4-(bis(4-chlorophenyl)methyl)piperazin-1-yl)
methyl)-4-(4-methylpiperazin-1-yl)benzonitrile
2-((4-(bis(4-isopropylphenyl)methyl)piperazin-1-yl)
methyl)-4-((2-(dimethylamino)ethyl)(methyl)amino)
benzonitrile
2-((4-(bis(4-tert-butylphenyl)methyl)piperazin-1-yl)
methyl)-4-((2-(dimethylamino)ethyl)(methyl)amino)
benzonitrile
2-((4-(bis(4-bromophenyl)methyl)piperazin-1-yl)
methyl)-4-((2-(dimethylamino)ethyl)(methyl)amino)
benzonitrile
2-((4-(bis(4-cyclopropylphenyl)methyl)piperazin-1-yl)
methyl)-4-((2-(dimethylamino)ethyl)(methyl)amino)
benzonitrile
2-((4-(bis(4-chlorophenyl)methyl)piperazin-1-yl)
methyl)-4-(3-(dimethylamino)pyrrolidin-1-yl)benzoni-
trile
2-((4-(bis(4-chlorophenyl)methyl)piperazin-1-yl)
methyl)-4-(methyl(2-(pyrrolidin-1-yl)ethyl)amino)
benzonitrile
4-((2-(aziridin-1-yl)ethyl)(methyl)amino)-2-((4-(bis(4-
chlorophenyl)methyl)piperazin-1-yl)methyl)benzoni-
trile
2-((4-((4-chlorophenyl)(phenyl)methyl)piperazin-1-yl)
methyl)-4-(4-methyl-1,4-diazepan-1-yl)benzonitrile
2-((4-((4-chlorophenyl)(pyridin-4-yl)methyl)piperazin-1-
yl)methyl)-4-(4-methyl-1,4-diazepan-1-yl)benzonitrile
2-((4-(bis(4-chlorophenyl)methyl)piperidin-1-yl)
methyl)-4-((2-(dimethylamino)ethyl)(methyl)amino)
benzonitrile
2-((4-(bis(4-fluorophenyl)methyl)piperidin-1-yl)methyl)-
4-(4-methyl-1,4-diazepan-1-yl)benzonitrile
N-{3-[4-(4-chlorophenyl)piperazin-1-yl]methyl)-4-(trif-
luoromethyl)phenyl}-N,1-dimethylpyrrolidin-3-amine
4-[{2-[ethyl(methyl)amino]ethyl}(methyl)amino)-2-({4-
[1-(pyrazin-2-yl)ethyl]piperazin-1-yl}methyl)benzoni-
trile
N1-(3-[{4-[bis(3,4-dichlorophenyl)methyl]piperazin-1-
yl}methyl]-4-(trifluoromethyl)phenyl)-N2,N2-diethyl-
N1-methylethan-1,2-diamine
2-({4-[bis(4-chloro-3-methylphenyl)methyl]piperazin-1-
yl}methyl)-4-{[2-(dimethylamino)ethyl](methyl)
amino}benzonitrile
1-[3-({4-[cyclohexyl(3,4-dichlorophenyl)methyl]piper-
azin-1-yl}methyl)-4-(trifluoromethyl)phenyl]-4-
methyl-1,4-diazepane
2-({4-[(4-chlorophenyl)(cyclobutyl)methyl]piperazin-1-
yl}methyl)-4-(4-methyl-1,4-diazepan-1-yl)benzonitrile
2-[(4-chlorophenyl){4-(5-(4-methylpiperazin-1-yl)-2-
(trifluoromethyl)benzyl]piperazin-1-yl}methyl]pyra-
zine
4-(4-methylpiperazin-1-yl)-2-[(4-{(pyrazin-2-yl)[(4-(trif-
luoromethyl)phenyl]methyl}piperazin-1-yl)methyl]
benzonitrile
1-methyl-4-[3-({4-[(4-phenoxyphenyl)(pyridin-2-yl)
methyl]piperazin-1-yl}methyl)-4-(trifluoromethyl)
phenyl]-1,4-diazepane
N-{3-([4-{bis[4-(phenylthio)phenyl]methyl}piperazin-1-
yl]methyl)-4-(trifluoromethyl)phenyl}-1-ethyl-N-
methylpyrrolidin-3-amine
2-({4-{bis(4-(methylthio)phenyl]methyl}piperazin-1-yl)
methyl)-4-{[2-(dimethylamino)ethyl](methyl)
amino}benzonitrile
3-([4-{bis[4-(trifluoromethyl)phenyl]methyl}piperazin-
1-yl]methyl)-N-methyl-N-[2-(pyrrolidin-1-yl)ethyl]-4-
(trifluoromethyl)aniline
2-({4-[(4-cyanophenyl)(cyclopentyl)methyl]piperazin-1-
yl}methyl)-4-{[2-(dimethylamino)ethyl](methyl)
amino}benzonitrile
4-{1-(4-[5-{[2-(dimethylamino)ethyl](methyl)amino}-2-
(trifluoromethyl)benzyl]piperazin-1-yl)
ethyl}benzonitrile
4-([3-(1H-imidazol-1-yl)propyl]amino)-2-({4-[bis(4-
chlorophenyl)methyl]piperazin-1-yl}methyl)benzoni-
trile.

12. The compound or the pharmaceutically acceptable salt thereof as claimed in claim 2, wherein the heterocyclyl is pyrrolidinyl; wherein the three-membered cyclic group is aziridinyl, the four-membered cyclic group is azetidinyl, the five membered cyclic group is selected from the group consisting of pyrrolyl, pyrrolidinyl, imidazolyl, and oxazolyl, the six-membered cyclic group is selected from the group consisting of morpholinyl, piperazinyl, piperidinyl, pyridinyl, and pyrimidinyl, and the seven-membered cyclic group is 1,4-diazepanyl; the alkyl containing 1-4 carbon is methyl or ethyl; wherein the di-C1-C4 alkylamino is dimethylamino or diethylamino; and saturated heterocyclic groups containing one nitrogen are selected from the group consisting of cyclopropanyl and pyrrolidinyl.

13. The compound or the pharmaceutically acceptable salt thereof as claimed in claim 6, wherein alkyl containing 1 to 4 carbon atoms are selected from methyl or ethyl, di-C1-C4 alkylamino group is dimethylamino or diethylamino, cycloalkyl groups containing 3 to 5 carbon atoms is cyclopropyl, heterocyclic groups containing 3 to 5 carbon atoms and one nitrogen is pyrrolidinyl; the heteroaromatic ring containing 1 to 2 nitrogen atoms is pyridine rings or pyrimidine rings.

14. The compound or the pharmaceutically acceptable salt thereof as claimed in claim 10, wherein the alkyl containing 1-4 carbon atoms is methyl or ethyl; and wherein the di-C1-C4 alkylamino is dimethylamino or diethylamino; and wherein the cycloalkyl containing 3 to 5 carbon atoms is cyclopropyl; and wherein a saturated five-membered heterocyclic ring containing one nitrogen is pyrrolidinyl.

15. A pharmaceutical composition comprising a therapeutically effective amount of one or more compounds as claimed in claim 1 and one or more pharmaceutically acceptable excipients.

16. The pharmaceutical composition as claimed in claim 15, wherein the pharmaceutically acceptable salt refers to the product from salt forming reaction with an acid, including inorganic acid salts and organic acid salts.

17. The pharmaceutical composition comprising the therapeutically effective amount of the pharmaceutically acceptable salt of one compound as claimed in claim 1 and one or more pharmaceutically acceptable excipients.

18. The pharmaceutical composition as claimed in claim 16, wherein the inorganic acid salts is hydrochloride, hydrobromide or sulfate; the organic acid salts is acetate, lactate, succinate, fumarate, maleate, citrate, benzoate, methanesulfonate, or 4-methylbenzoate salt.

19. A method for treating viral infections, which comprises administering to the patient a therapeutically effective amount of the compound or one pharmaceutically acceptable salt thereof as claimed in claim 1, wherein the virus is the DNA virus and/or RNA virus.

20. The method as claimed in claim 19, wherein the DNA viruses are herpes viruses, hepatotropic viruses, adenoviruses, or papilloma viruses; and the RNA viruses are mumps viruses, influenza viruses, coronaviruses, retroviruses, enterovirus or flaviviruses, or, the viruses are hepatitis C viruses.

\* \* \* \* \*